United States Patent
Kang et al.

(10) Patent No.: US 10,385,374 B2
(45) Date of Patent: *Aug. 20, 2019

(54) PROCESSES FOR PRODUCING FERMENTATION PRODUCTS

(71) Applicant: NOVOZYMES A/S, Bagsvaerd (DK)

(72) Inventors: Zhengfang Kang, Raleigh, NC (US);
Christie Strahler, Raleigh, NC (US);
Suzanne Clark, Youngsville, NC (US);
Kristian Bertel Rømer M. Krogh,
Bagsvaerd (DK); Tang Lan, Beijing (CN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/913,092

(22) Filed: Mar. 6, 2018

(65) Prior Publication Data

US 2018/0273998 A1    Sep. 27, 2018

Related U.S. Application Data

(63) Continuation of application No. 15/021,180, filed as application No. PCT/CN2014/086235 on Sep. 10, 2014, now Pat. No. 9,951,364.

(30) Foreign Application Priority Data

Sep. 11, 2013    (WO) ............... PCT/CN2013/083313

(51) Int. Cl.

| | | |
|---|---|---|
| *C12P 19/14* | (2006.01) | |
| *C12N 9/42* | (2006.01) | |
| *C12N 9/34* | (2006.01) | |
| *C12N 9/52* | (2006.01) | |
| *C12P 7/14* | (2006.01) | |
| *C12N 9/28* | (2006.01) | |
| *C12P 19/02* | (2006.01) | |
| *C12P 7/06* | (2006.01) | |

(52) U.S. Cl.
CPC ............. *C12P 19/14* (2013.01); *C12N 9/244* (2013.01); *C12N 9/2417* (2013.01); *C12N 9/2428* (2013.01); *C12N 9/2437* (2013.01); *C12N 9/52* (2013.01); *C12P 7/06* (2013.01); *C12P 7/14* (2013.01); *C12P 19/02* (2013.01); *C12P 2203/00* (2013.01); *C12Y 302/01001* (2013.01); *C12Y 302/01003* (2013.01); *C12Y 302/01006* (2013.01); *C12Y 304/24* (2013.01); *Y02E 50/17* (2013.01)

(58) Field of Classification Search
CPC ........... C12P 7/06; C12P 2203/00; C12P 7/14; C12P 19/02; C12P 19/14; C12N 9/2417; C12N 9/2437; C12N 9/52; C12N 9/2428; C12N 9/244; Y02E 50/17; C12Y 302/01001; C12Y 304/24; C12Y 302/01006; C12Y 302/01003

See application file for complete search history.

(56) References Cited

FOREIGN PATENT DOCUMENTS

| WO | 98/028410 A1 | 7/1998 | |
|---|---|---|---|
| WO | 2009/020459 A2 | 2/2009 | |
| WO | 2011/079158 A2 | 6/2011 | |
| WO | WO 2011/072191 A2 * | 6/2011 | ........... C07K 14/435 |
| WO | 2012/088303 A2 | 6/2012 | |
| WO | 2012/149275 A1 | 11/2012 | |
| WO | 2013/019780 A2 | 2/2013 | |

OTHER PUBLICATIONS

Yennamalli et al, 2011, BMC Structural Biology 11(1), 10.
Broun et al, 1998, Science 282, 1315-1317.
Chica et al, 2005, Curr Op Biotechnol 16, 378-384.
Devos et al, 2000, Proteins Struc, Func, Genet 41, 98-107.
Seffernick et al, 2001, J Bacteriol 183(8), 2405-2410.
Sen et al, 2007, Appl Biochem Biotechnol 143, 212-223.
Witkowski et al, 1999, Biochemistry 38, 11643-11650.
Whisstock et al, 2003, Quart Rev Biophys 36(3), 307-340.

* cited by examiner

*Primary Examiner* — Ganapathirama Raghu
(74) *Attorney, Agent, or Firm* — David Fazzolare

(57) ABSTRACT

The present invention relates to processes for producing fermentation products from starch-containing material, wherein an alpha-amylase and a thermostable endoglucanase is present and/or added during liquefaction. The invention also relates to compositions suitable for use in processes of the invention.

20 Claims, No Drawings
Specification includes a Sequence Listing.

PROCESSES FOR PRODUCING FERMENTATION PRODUCTS

CROSS-REFERENCE TO RELATED APPLICATIONS

This application is a continuation of U.S. application Ser. No. 15/021,180 filed Mar. 10, 2016, now U.S. Pat. No. 9,951,364, which is a 35 U.S.C. 371 national application of PCT/CN2014/086235 filed Sep. 10, 2014, which claims priority or the benefit under 35 U.S.C. 119 of International application no. PCT/CN2013/083313 filed Sep. 11, 2013, the contents of which are fully incorporated herein by reference.

FIELD OF THE INVENTION

The present invention relates to processes for producing fermentation products from starch-containing material. The invention also relates to a composition suitable for use in a process of the invention.

REFERENCE TO A SEQUENCE LISTING

This application contains a Sequence Listing in computer readable form. The computer readable form is incorporated herein by reference.

BACKGROUND OF THE INVENTION

Production of fermentation products, such as ethanol, from starch-containing material is well-known in the art. Industrially two different kinds of processes are used today. The most commonly used process, often referred to as a "conventional process", includes liquefying gelatinized starch at high temperature using typically a bacterial alpha-amylase, followed by simultaneous saccharification and fermentation carried out in the presence of a glucoamylase and a fermentation organism. Another well-known process, often referred to as a "raw starch hydrolysis"-process (RSH process), includes simultaneously saccharifying and fermenting granular starch below the initial gelatinization temperature typically in the presence of at least a glucoamylase.

Despite significant improvement of fermentation product production processes over the past decade a significant amount of residual starch material is not converted into the desired fermentation product, such as ethanol.

Therefore, there is still a desire and need for providing processes for producing fermentation products, such as ethanol, from starch-containing material that can provide a higher fermentation product yield, or other advantages, compared to a conventional process.

SUMMARY OF THE INVENTION

The present invention relates to processes of producing fermentation products, such as ethanol, from starch-containing material using a fermenting organism. The invention also relates to compositions for use in a process of the invention.

In the first aspect the invention relates to processes for producing fermentation products, such as ethanol, from starch-containing material comprising the steps of:

i) liquefying the starch-containing material at a temperature above the initial gelatinization temperature using:
   an alpha-amylase;
   an endoglucanase having a Melting Point (DSC) above 70° C.;
ii) saccharifying using a carbohydrate-source generating enzyme;
iii) fermenting using a fermenting organism.

In an embodiment a cellulase or cellulolytic enzyme composition is present or adding during fermentation or simultaneous saccharification and fermentation (SSF).

In a second aspect the invention relates to compositions comprising: i) an alpha-amylase;
ii) an endoglucanase having a Melting Point (DSC) above 70° C.;
iii) optionally a protease having a thermostability value of more than 20% determined as Relative Activity at 80° C./70° C.; and
iv) optionally a carbohydrate-source generating enzyme.

The invention also relates to the use of a composition of the invention for liquefying a starch-containing material.

Finally the invention relates to methods of producing liquefied starch comprising liquefying a starch-containing material with a composition of the invention.

DETAILED DESCRIPTION OF THE INVENTION

The present invention relates to processes of producing fermentation products, such as ethanol, from starch-containing material using a fermenting organism. The invention also relates to compositions for use in a process of the invention.

The inventors have found that an increased ethanol yield is obtained when liquefying starch-containing material using an alpha-amylase in the presence of a thermostable endoglucanase and when a cellulase is present in fermentation (e.g., SSF).

In the first aspect the invention relates to processes for producing fermentation products, preferably ethanol, comprising the steps of:

i) liquefying the starch-containing material at a temperature above the initial gelatinization temperature using:
   an alpha-amylase;
   an endoglucanase having a Melting Point (DSC) above 70° C.;
ii) saccharifying using a carbohydrate-source generating enzyme;
iii) fermenting using a fermenting organism.

Steps ii) and iii) may be carried out either sequentially or simultaneously. In a preferred embodiment steps ii) and iii) are carried out simultaneously. The alpha-amylase, the thermostable endoglucanase having a Melting Point (DSC) above 70° C., such as between 70° C. and 95° C., may be added before and/or during liquefaction step i). Optionally a protease, a carbohydrate-source generating enzyme, preferably a glucoamylase, a pullulanase, and/or phytase may be present or added as well. In a preferred embodiment a composition of the invention defined below may suitably be used in liquefaction in a process of the invention. The enzymes may be added individually or as a blend composition comprising an alpha-amylase and thermostable endoglucanase having a Melting Point (DSC) above 70° C. and optionally a protease, a carbohydrate-source generating enzyme, a pullulanase and/or phytase.

Examples of alpha-amylases can be found in the "Alpha-Amylase Present and/or Added During Liquefaction"-section below.

In a preferred embodiment the alpha-amylase is a variant of the one shown in SEQ ID NO: 1 herein, such as one derived from a strain Bacillus stearomthermphilus, with mutations selected from the group of:

I181*+G182*+N193F+E129V+K177L+R179E;
I181*+G182*+N193F+V59A+Q89R+E129V+K177L+R179E+H208Y+K220P+N224L+Q254S;
I181*+G*+182*+N193F+V59A+Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

Bacillus stearothermophilus alpha-amylases are typically naturally truncated when produced to be around 491 amino acids long (compared to SEQ ID NO: 3 in WO 99/19467 or SEQ ID NO: 1 herein), such as from 480-495 amino acids long.

In an embodiment the bacterial alpha-amylase, e.g., Bacillus alpha-amylase, such as especially Bacillus stearothermophilus alpha-amylase is dosed in liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS.

In an embodiment the bacterial alpha-amylase, e.g., Bacillus alpha-amylase, such as especially Bacillus stearothermophilus alpha-amylases is dosed in liquefaction in a concentration of between 0.0001-1 mg EP (Enzyme Protein)/g DS, e.g., 0.0005-0.5 mg EP/g DS, such as 0.001-0.1 mg EP/g DS.

Examples of endoglucanases having a Melting Point (DSC) above 70° C. can be found in the "Thermostable Endoglucanase Present and/or Added During Liquefaction"-section below.

In a preferred embodiment the endoglucanase is the one shown in SEQ ID NO: 3 herein, such as one derived from a strain of Talaromyces leycettanus (WO2013/019780), or an endoglucanase having at least 80% identity to SEQ ID NO: 3 herein.

In a preferred embodiment the endoglucanase is the one shown in SEQ ID NO: 3 herein, such as one derived from a strain of Talaromyces leycettanus (WO2013/019780—hereby incorporated by reference), or an endoglucanase having at least 90% identity to SEQ ID NO: 3 herein having a Melting Point (DSC) above 70° C.

Examples of optional proteases can be found in the "Protease Present and/or Added During Liquefaction"-section below.

Examples of suitable optional carbohydrate-source generating enzymes, preferably thermostable carbohydrate-source generating enzymes, in particular glucoamylases, can be found in the "Carbohydrate-Source Generating Enzymes Present and/or Added During Liquefaction"-section below.

A suitable optional pullulanase can be found in the "Pullulanase Present and/or Added During Liquefaction"-section below.

In a preferred embodiment the pullulanase is derived from Bacillus sp.

Examples of phytases can be found in the "Phytase Present and/or Added During Liquefaction"-section below.

In a preferred embodiment the phytase is derived from a strain of Buttiauxella.

A suitable cellulase or cellulolytic enzyme composition present and/or added during saccharification and/or fermentation or simultaneous saccharification and fermentation (SSF) can be found in the "Cellulase or Cellulolytic Enzyme Composition Present and/or Added During Saccharification and/or Fermentation or SSF"-section below.

In an embodiment the cellulase or cellulolytic enzyme composition is derived from Trichoderma reesei.

In a preferred embodiment the cellulolytic enzyme composition is a Trichoderma reesei cellulolytic enzyme composition, further comprising Thermoascus aurantiacus GH61A polypeptide having cellulolytic enhancing activity (SEQ ID NO: 2 in WO 2005/074656 or SEQ ID NO: 30 herein) and Aspergillus fumigatus beta-glucosidase (SEQ ID NO: 2 of WO 2005/047499 or SEQ ID NO: 29 herein).

In an embodiment the cellulolytic enzyme composition is a Trichoderma reesei cellulolytic enzyme composition further comprising Penicillium emersonii GH61A polypeptide disclosed as SEQ ID NO: 2 in WO 2011/041397 or SEQ ID NO: 31 herein, and Aspergillus fumigatus beta-glucosidase disclosed as SEQ ID NO: 2 in WO 2005/047499 or SEQ ID NO: 29 herein, or a variant thereof, which variant has one of, preferably all of, the following substitutions: F100D, S283G, N456E, F512Y (using SEQ ID NO: 29 for numbering).

According to the process of the invention the pH during liquefaction may be between 4.0-6.5, such as 4.5-6.2, such as above 4.8-6.0, such as between 5.0-5.8.

According to the invention the temperature is above the initial gelatinization temperature. The term "initial gelatinization temperature" refers to the lowest temperature at which solubilization of starch, typically by heating, begins. The temperature can vary for different starches. The initial gelanitization temperature may be from 50-70° C.

In an embodiment the temperature during liquefaction step i) is in the range from 70-100° C., such as between 70-95° C., such as between 75-90° C., preferably between 80-90° C., such as around 85° C.

In an embodiment, the process of the invention further comprises, prior to the step i), the steps of:

a) reducing the particle size of the starch-containing material, preferably by dry milling;
b) forming a slurry comprising the starch-containing material and water.

The starch-containing starting material, such as whole grains, may be reduced in particle size, e.g., by milling, in order to open up the structure, to increase the surface area and allowing for further processing. Generally there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry and wet millings are well known in the art of starch processing. According to the present invention dry milling is preferred. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

The aqueous slurry may contain from 10-55 w/w-% dry solids (DS), preferably 25-45 w/w-% dry solids (DS), more preferably 30-40 w/w-% dry solids (DS) of starch-containing material.

The slurry may be heated to above the initial gelatinization temperature, preferably to between 70-95° C., such as between 80-90° C., between pH 5.0-7.0, preferably between 5.0 and 6.0, for 30 minutes to 5 hours, such as around 2 hours.

In an embodiment liquefaction step i) is carried out for 0.5-5 hours at a temperature from 70-95° C. at a pH from 4-6.

In a preferred embodiment liquefaction step i) is carried out for 0.5-3 hours at a temperature from 80-90° C. at a pH from 4-6.

The alpha-amylase and thermostable endoglucanase, and optional protease, optional carbohydrate-source generating enzyme, in particular glucoamylase, optional pullulanase, and/or optional phytase, may initially be added to the aqueous slurry to initiate liquefaction (thinning). In an embodiment only a portion of the enzymes is added to the aqueous slurry, while the rest of the enzymes are added during liquefaction step i).

The aqueous slurry may in an embodiment be jet-cooked to further gelatinize the slurry before being subjected to liquefaction in step i). The jet-cooking may be carried out at a temperature between 95-160° C., such as between 110-145° C., preferably 120-140° C., such as 125-135° C., preferably around 130° C. for about 1-15 minutes, preferably for about 3-10 minutes, especially around about 5 minutes.

Saccharification and Fermentation

According to the process of the invention one or more carbohydrate-source generating enzymes, in particular glucoamylase, may be present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase. The carbohydrate-source generating enzyme added during saccharification step ii) and/or fermentation step iii) is typically different from the optional carbohydrate-source generating enzyme, in particular glucoamylase, optionally added during liquefaction step i). In an embodiment the carbohydrate-source generating enzymes, in particular glucoamylase, is added together with a fungal alpha-amylase.

Examples of carbohydrate-source generating enzymes, including glucoamylases, can be found in the "Carbohydrate-Source Generating Enzyme Present and/or Added During Saccharification and/or Fermentation"-section below.

When doing sequential saccharification and fermentation, saccharification step ii) may be carried out at conditions well-known in the art. For instance, the saccharification step ii) may last up to from about 24 to about 72 hours.

In an embodiment a pre-saccharification step is done. In an embodiment a carbohydrate-source generating enzyme is added during pre-saccharification carried out before saccharification step ii) and/or fermentation step iii). The carbohydrate-source generating enzyme may also be added during pre-saccharification carried out before simultaneous saccharification and fermentation (SSF).

In an embodiment a carbohydrate-source generating enzyme, preferably glucoamylase, and/or the cellulolytic enzymes composition are added during pre-saccharification carried out before saccharification step (b) and/or fermentation step (c). The carbohydrate-source generating enzyme, preferably glucoamylase, and the cellulolytic enzyme composition may also be added during pre-saccharification carried out before simultaneous saccharification and fermentation (SSF).

Pre-saccharification is typically done for 40-90 minutes at a temperature between 30-65° C., typically about 60° C. Pre-saccharification may be followed by saccharification during fermentation in simultaneous saccharification and fermentation ("SSF"). Saccharification is typically carried out at temperatures from 20-75° C., preferably from 40-70° C., typically around 60° C., and at a pH between 4 and 5, such as around pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There may be no holding stage for the saccharification, meaning that a fermenting organism, such as yeast, and enzyme(s), in a preferred embodiment according to the invention a glucoamylase and a cellulolytic enzyme composition, may be added together. However, it is also contemplated to add the fermenting organism and enzyme(s) separately. Fermentation or SSF may, according to the invention, typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Fermentation Medium

"Fermentation media" or "fermentation medium" refers to the environment in which fermentation is carried out. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "Fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley.

In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

Alpha-Amylase Present and/or Added During Liquefaction

According to the invention an alpha-amylase is present and/or added during liquefaction together with an endoglucanase having a Melting Point (DSC) above 70° C., such as between 70° C. and 95° C., and an optional protease, an optional carbohydrate-source generating enzyme, in particular a glucoamylase, an optional a pullulanase, and/or an optional phytase.

The alpha-amylase added during liquefaction step i) may be any alpha-amylase. Preferred are bacterial alpha-amylases, such as especially *Bacillus* alpha-amylases, such as *Bacillus stearothermophilus* alpha-amylases, which are stable at temperature used during liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus, Bacillus* sp. TS-23, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 and the *Bacillus* sp. TS-23 alpha-amylase disclosed as SEQ ID NO: 1 in WO 2009/061380 (all sequences are hereby incorporated by reference).

In an embodiment the bacterial alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467 and SEQ ID NO: 1 in WO 2009/061380.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 1 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases, or variant thereof, may be naturally truncated during recombinant production. For instance, the mature *Bacillus stearothermophilus* alpha-amylase may be a truncated so it has around 491 amino acids (compared to SEQ ID NO: 3 in WO 99/19467), such as from 480-495 amino acids.

The *Bacillus* alpha-amylase may also be a variant and/or hybrid. Examples of such a variant can be found in any of WO 96/23873, WO 96/23874, WO 97/41213, WO 99/19467, WO 00/60059, WO 02/10355 and WO 2009/061380 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 1 herein. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467 or SEQ ID NO: 1 herein.

In an embodiment the variant is a S242A, E or Q variant, preferably a S242Q variant, of the *Bacillus stearothermophilus* alpha-amylase (using SEQ ID NO: 1 herein for numbering).

In an embodiment the variant is a position E188 variant, preferably E188P variant of the *Bacillus stearothermophilus* alpha-amylase (using SEQ ID NO: 1 herein for numbering).

Other contemplated variant are *Bacillus* sp. TS-23 variant disclosed in WO2009/061380, especially variants defined in claim 1 of WO2009/061380.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions:

G48A+T491+G107A+H156Y+A181T+N190F+I201F+ A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al., 2002, The Journal of Biological Chemistry 277(29): 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

According to the invention the alpha-amylase used in a process of the invention or comprised in a composition of the invention in combination with an endoglucanase having a Melting Point (DSC) above 70° C., may be a thermostable alpha-amylase, such as a thermostable bacterial alpha-amylase, preferably from *Bacillus stearothermophilus* or *Bacillus* sp. TS-23. In an embodiment the alpha-amylase used according to the invention has a T½ (min) at pH 4.5, 85° C., 0.12 mM $CaCl_2$ of at least 10.

In an embodiment the thermostable alpha-amylase has a T½ (min) at pH 4.5, 85° C., 0.12 mM $CaCl_2$, of at least 15.

In an embodiment the thermostable alpha-amylase has a T½ (min) at pH 4.5, 85° C., 0.12 mM $CaCl_2$, of at least 20.

In an embodiment the thermostable alpha-amylase has a T½ (min) at pH 4.5, 85° C., 0.12 mM $CaCl_2$, of at least 25.

In an embodiment the thermostable alpha-amylase has a T½ (min) at pH 4.5, 85° C., 0.12 mM $CaCl_2$, of at least 30.

In an embodiment the thermostable alpha-amylase has a T½ (min) at pH 4.5, 85° C., 0.12 mM $CaCl_2$, of at least 40.

In an embodiment the thermostable alpha-amylase has a T½ (min) at pH 4.5, 85° C., 0.12 mM $CaCl_2$, of at least 50.

In an embodiment the thermostable alpha-amylase has a T½ (min) at pH 4.5, 85° C., 0.12 mM $CaCl_2$, of at least 60.

In an embodiment the thermostable alpha-amylase has a T½ (min) at pH 4.5, 85° C., 0.12 mM $CaCl_2$, between 10-70.

In an embodiment the thermostable alpha-amylase has a T½ (min) at pH 4.5, 85° C., 0.12 mM $CaCl_2$, between 15-70.

In an embodiment the thermostable alpha-amylase has a T½ (min) at pH 4.5, 85° C., 0.12 mM $CaCl_2$, between 20-70.

In an embodiment the thermostable alpha-amylase has a T½ (min) at pH 4.5, 85° C., 0.12 mM $CaCl_2$, between 25-70.

In an embodiment the thermostable alpha-amylase has a T½ (min) at pH 4.5, 85° C., 0.12 mM $CaCl_2$, between 30-70.

In an embodiment the thermostable alpha-amylase has a T½ (min) at pH 4.5, 85° C., 0.12 mM $CaCl_2$, between 40-70.

In an embodiment the thermostable alpha-amylase has a T½ (min) at pH 4.5, 85° C., 0.12 mM $CaCl_2$, between 50-70.

In an embodiment the thermostable alpha-amylase has a T½ (min) at pH 4.5, 85° C., 0.12 mM $CaCl_2$, between 60-70.

In an embodiment the alpha-amylase is an bacterial alpha-amylase, preferably derived from the genus *Bacillus*, especially a strain of *Bacillus stearothermophilus*, in particular the *Bacillus stearothermophilus* as disclosed in WO 99/19467 as SEQ ID NO: 3 or SEQ ID NO: 1 herein with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optional substitution N193F, further comprising mutations selected from below list:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;

K220P + N224L + S242Q + Q254S;
M284V;
V59A + Q89R + E129V + K177L + R179E + Q254S + M284V.

In a preferred embodiment the alpha-amylase is selected from the group of *Bacillus stearomthermphilus* alpha-amylase variants:

I181*+G182*+N193F+E129V+K177L+R179E;

I181*+G182*+N193F+V59A+Q89R+E129V+K177L+ R179E+H208Y+K220P+N224L+Q254S;

I181*+G182*+N193F+V59A+Q89R+E129V+K177L+ R179E+Q254S+M284V; and

I181*+G182*+N193F+E129V+K177L+R179E+K220P+ N224L+S242Q+Q254S (using SEQ ID NO: 1 herein for numbering).

In an embodiment the bacterial alpha-amylase, such as *Bacillus* alpha-amylase, such as as *Bacillus stearomthermphilus* alpha-amylase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 1 herein.

In an embodiment the bacterial alpha-amylase variant, such as *Bacillus* alpha-amylase variant, such as *Bacillus stearomthermphilus* alpha-amylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 1 herein.

It should be understood that when referring to *Bacillus stearothermophilus* alpha-amylase and variants thereof they are normally produced naturally in truncated form. In particular, the truncation may be so that the *Bacillus stearothermophilus* alpha-amylase shown in SEQ ID NO: 3 in WO 99/19467 or SEQ ID NO: 1 herein, or variants thereof, are truncated in the C-terminal and are typically around 491 amino acids long, such as from 480-495 amino acids long.

Thermostable Endoglucanase Present and/or Added During Liquefaction

According to the invention an endoglucanase ("EG") having a Melting Point (DSC) above 70° C., such as between 70° C. and 95° C. is present and/or added to the liquefaction step i) in combination with an alpha-amylase, such as a thermostable bacterial alpha-amylase. The endoglucanase and the alpha-amylase may be added individually or as an enzyme blend composition. In a preferred embodiment the enzyme blend is a composition of the invention comprising an alpha-amylase and an endoglucanase having a Melting Point (DSC) above 70° C., such as between 70° C. and 95° C.

The thermostability of an endoglucanase may be determined as described in the "Materials & Methods"-section under "Determination of Td by Differential Scanning calorimetry for Endoglucanases".

In an embodiment the endoglucanase has a Melting Point (DSC) above 72° C., such as above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In a preferred embodiment the endogluconase used in a process of the invention comprised in a composition opf the invention is a Glycoside Hydrolase Family 5 endoglucanase or GH5 endoglucanase (see the CAZy database on the "www.cazy.org" webpage. In an embodiment the GH5 endoglucanase is from family EG II, such as the *Talaromyces leycettanus* endoglucanase shown in SEQ ID NO: 3 herein; *Penicillium capsulatum* endoglucanase shown in SEQ ID NO: 4 herein, and *Trichophaea saccata* endoglucnase shown in SEQ ID NO: 5 herein.

In an embodiment the endoglucanase is a family GH45 endoglucanase. In an embodiment the GH45 endoglucanase is from family EG V, such as the *Sordaria fimicola* shown in SEQ ID NO: 7 herein or the *Thielavia terrestris* endoglucanase shown in SEQ ID NO: 6 herein. In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3 herein. In an embodiment the endoglucanase is derived from a strain of the genus *Talaromyces*, such as a strain of *Talaromyces leycettanus*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 4 herein, preferably derived from a strain of the genus *Penicillium*, such as a strain of *Penicillium capsulatum*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 5 herein, preferably derived from a strain of the genus *Trichophaea*, such as a strain of *Trichophaea saccata*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 6 herein, preferably derived from a strain of the genus *Thielavia*, such as a strain of *Thielavia terrestris*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 7 herein, preferably derived from a strain of the genus *Sordaria*, such as a strain of *Sordaria fimicola*.

In an embodiment the thermostable endoglucanase is added in liquefaction step i) at a dose of 1-10,000 µg EP (Enzymes Protein)/g DS), such as 10-1,000 µg EP/g DS.

Protease Present and/or Added During Liquefaction

In an embodiment of the invention a protease, such as a thermostable protease, is present and/or added during liquefaction together with an alpha-amylase, such as a thermostable alpha-amylase, and an endoglucanase having a Melting Point (DSC) above 70° C., and optionally a carbohydrate-source generating enzyme, in particular a glucoamylase, optionally a pullulanase and/or optionally a phytase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods"-section.

There are no limitations on the origin of the thermostable protease used in a process or composition of the invention as long as it fulfills the thermostability properties defined below.

In one embodiment the protease is of fungal origin.

The thermostable protease may be a variant of, e.g., a wild-type protease as long as the protease has the thermostability properties defined herein. In a preferred embodiment the thermostable protease is a variant of a metallo protease as defined above. In an embodiment the thermostable protease used in a process or composition of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 2 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+A126V+D142L;
D79L+S87P+D142L.

In a preferred embodiment the thermostable protease is a variant of the mature metallo protease disclosed as the mature part of SEQ ID NO: 2 disclosed in WO 2003/048353 or the mature part of SEQ ID NO: 1 in WO 2010/008841 or SEQ ID NO: 2 herein with the following mutations:

D79L+S87P+A112P+D142L;
D79L+S87P+D142L; or

A27K+D79L+Y82F+S87G+D104P+A112P+A126V+ D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 2 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 13 herein.

In another embodiment the thermostable protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Bio, Japan.

The *Pyrococcus furiosus* protease is a thermostable protease according to the invention. The commercial product *Pyrococcus furiosus* protease (Pfu S) was found to have a thermostability of 110% (80° C./70° C.) and 103% (90° C./70° C.) at pH 4.5 determined as described in Example 2 herein.

In one embodiment a thermostable protease used in a process of the invention has a thermostability value of more than 20% determined as Relative Activity at 80° C./70° C. determined as described in Example 2.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C.

In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C. determined as described in Example 2.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2.

In an embodiment the protease may have a themostability for above 90, such as above 100 at 85° C. as determined using the Zein-BCA assay as disclosed in Example 3.

In an embodiment the protease has a themostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay.

Carbohydrate-Source Generating Enzyme Present and/or Added During Liquefaction

According to the invention a carbohydrate-source generating enzyme, in particular a glucoamylase, preferably a thermostable glucoamylase, may be present and/or added during liquefaction together with an alpha-amylase, as a thermostable alpha-amylase, and an endoglucanase having a Melting Point (DSC) above 70° C., and optionally a pullulanase and/or optionally a phytase.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In an embodiment the carbohydrate-source generating enzyme, preferably a thermostable glucoamylase, has a Relative Activity heat stability at 85° C. of at least 20%, at least 30%, preferably at least 35% determined as described in Example 4 (heat stability).

In an embodiment the carbohydrate-source generating enzyme is a glucoamylase having a relative activity pH optimum at pH 5.0 of at least 90%, preferably at least 95%, preferably at least 97%, such as 100% determined as described in Example 4 (pH optimum).

In an embodiment the carbohydrate-source generating enzyme is a glucoamylase having a pH stability at pH 5.0 of at least at least 80%, at least 85%, at least 90% determined as described in Example 4 (pH stability).

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 14 herein.

In an embodiment the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 14 herein.

In an embodiment the carbohydrate-source generating enzyme, in particular thermostable glucoamylase, is the *Penicillium oxalicum* glucoamylase shown in SEQ ID NO: 14 herein.

In a preferred embodiment the carbohydrate-source generating enzyme is a variant of the *Penicillium oxalicum* glucoamylase disclosed as SEQ ID NO: 2 in WO 2011/127802 and shown in SEQ ID NO: 9 or 14 herein, having a K79V substitution (referred to as "PE001") (using the mature sequence shown in SEQ ID NO: 14 for numbering). The K79V glucoamylase variant has reduced sensitivity to protease degradation relative to the parent as disclosed in WO 2013/036526 (which is hereby incorporated by reference).

In an embodiment the thermostable glucoamylase is a variant of the *Penicillium oxalicum* glucoamylase disclosed as SEQ ID NO: 2 in WO 2011/127802 and shown as the mature sequence in SEQ ID NO: 9 or 14 herein. In a preferred embodiment the *Penicillium oxalicum* glucoamylase is the one disclosed as SEQ ID NO: 2 in WO 2011/127802 and shown in SEQ ID NO: 9 or 14 herein having Val (V) in position 79 (using SEQ ID NO: 14 herein for numbering).

Contemplated *Penicillium oxalicum* glucoamylase variants are disclosed in WO 2013/053801 (which is hereby incorporated by reference).

In an embodiment these variants have reduced sensitivity to protease degradation.

In an embodiment these variant have improved thermostability compared to the parent.

More specifically, in an embodiment the glucoamylase has a K79V substitution (using SEQ ID NO: 14 herein for numbering), corresponding to the PE001 variant, and further comprises at least one of the following substitutions or combination of substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or

P2N+P4S+P11F+T65A+Q327F+E501V+Y504T+ K524T+G526A; or
P2N+P4S+P11F+K34Y+T65A+Q327F+D445N+ V447S+E501V+Y504T; or
P2N+P4S+P11F+R31S+K33V+T65A+Q327F+D445N+ V447S+E501V+Y504T; or
P2N+P4S+P11F+D26N+K34Y+T65A+Q327F+E501V+ Y504T; or
P2N+P4S+P11F+T65A+F80*+Q327F+E501V+Y504T; or
P2N+P4S+P11F+T65A+K112S+Q327F+E501V+ Y504T; or
P2N+P4S+P11F+T65A+Q327F+E501V+Y504T+ T516P+K524T+G526A; or
P2N+P4S+P11F+T65A+Q327F+E501V+N502T+ Y504*; or
P2N+P4S+P11F+T65A+Q327F+E501V+Y504T; or
P2N+P4S+P11F+T65A+S103N+Q327F+E501V+ Y504T; or
K5A+P11F+T65A+Q327F+E501V+Y504T; or
P2N+P4S+P11F+T65A+Q327F+E501V+Y504T+ T516P+K524T+G526A; or
P2N+P4S+P11F+T65A+V79A+Q327F+E501V+Y504T; or
P2N+P4S+P11F+T65A+V79G+Q327F+E501V+Y504T; or
P2N+P4S+P11F+T65A+V79I+Q327F+E501V+Y504T; or
P2N+P4S+P11F+T65A+V79L+Q327F+E501V+Y504T; or
P2N+P4S+P11F+T65A+V79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+Q327F+E501V+Y504T; or
P2N+P4S+P11F+T65A+G220N+Q327F+E501V+ Y504T; or
P2N+P4S+P11F+T65A+Y245N+Q327F+E501V+ Y504T; or
P2N+P4S+P11F+T65A+Q253N+Q327F+E501V+ Y504T; or
P2N+P4S+P11F+T65A+D279N+Q327F+E501V+ Y504T; or
P2N+P4S+P11F+T65A+Q327F+S359N+E501V+ Y504T; or
P2N+P4S+P11F+T65A+Q327F+D370N+E501V+ Y504T; or
P2N+P4S+P11F+T65A+Q327F+V460S+E501V+ Y504T; or
P2N+P4S+P11F+T65A+Q327F+V460T+P468T+ E501V+Y504T; or
P2N+P4S+P11F+T65A+Q327F+T463N+E501V+ Y504T; or
P2N+P4S+P11F+T65A+Q327F+S465N+E501V+ Y504T; or
P2N+P4S+P11F+T65A+Q327F+T477N+E501V+ Y504T.

In a preferred embodiment the *Penicillium oxalicum* glucoamylase variant has a K79V substitution using SEQ ID NO: 14 herein for numbering (PE001 variant), and further comprises one of the following mutations:
P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or P2N+P4S+P11F+T65A+Q327F+E501V+Y504T; or
P11F+T65A+Q327W+E501V+Y504T.

In an embodiment the glucoamylase variant, such as *Penicillium oxalicum* glucoamylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature polypeptide of SEQ ID NO: 14 herein.

The carbohydrate-source generating enzyme, in particular, may be added in amounts from 0.1-100 micrograms EP/g, such as 0.5-50 micrograms EP/g, such as 1-25 micrograms EP/g, such as 2-12 micrograms EP/g DS.

Pullulanase Present and/or Added During Liquefaction

Optionally a pullulanase may be present and/or added during liquefaction step i) together with an alpha-amylase and a protease. As mentioned above a carbohydrate-source generating enzyme, preferably a thermostable glucoamylase, may also be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO 92/02614.

In an embodiment the pullulanase is a family GH57 pullulanase. In an embodiment the pullulanase includes an X47 domain as disclosed in WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown WO 2011/087836 truncated at the X4 site right after the X47 domain. The pullulanase may also be a hybrid of the *Thermococcus litoralis* and *Thermococcus hydrothermalis* pullulanases or a *T. hydrothermalis/ T. litoralis* hybrid enzyme with truncation site X4 disclosed in WO 2011/087836 (which is hereby incorporated by reference).

In another embodiment the pullulanase is one comprising an X46 domain disclosed in WO 2011/076123 (Novozymes).

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME 400L, PROMOZYME™ D2 (Novozymes A/S, Denmark), OPTIMAX L-300 (Genencor Int., USA), and AMANO 8 (Amano, Japan).

Phytase Present and/or Added During Liquefaction

Optionally a phytase may be present and/or added during liquefaction in combination with an alpha-amylase and an endoglucanase having a melting point (DSC) above 70° C.

A phytase used according to the invention may be any enzyme capable of effecting the liberation of inorganic phosphate from phytic acid (myo-inositol hexakisphosphate) or from any salt thereof (phytates). Phytases can be classified according to their specificity in the initial hydrolysis step, viz. according to which phosphate-ester group is hydrolyzed first. The phytase to be used in the invention may have any specificity, e.g., be a 3-phytase (EC 3.1.3.8), a 6-phytase (EC 3.1.3.26) or a 5-phytase (no EC number). In an embodiment the phytase has a temperature optimum above 50° C., such as in the range from 50-90° C.

The phytase may be derived from plants or microorganisms, such as bacteria or fungi, e.g., yeast or filamentous fungi.

A plant phytase may be from wheat-bran, maize, soy bean or lily pollen. Suitable plant phytases are described in Thomlinson et al, Biochemistry, 1 (1962), 166-171; Barrientos et al, Plant. Physiol., 106 (1994), 1489-1495; WO 98/05785; WO 98/20139.

A bacterial phytase may be from genus *Bacillus, Citrobacter, Hafnia, Pseudomonas, Buttiauxella* or *Escherichia*, specifically the species *Bacillus subtilis, Citrobacter braakii, Citrobacter freundii, Hafnia alvei, Buttiauxella gaviniae, Buttiauxella agrestis, Buttiauxella noackies* and *E. coli*. Suitable bacterial phytases are described in Paver and Jagannathan, 1982, Journal of Bacteriology 151:1102-1108; Cosgrove, 1970, Australian Journal of Biological Sciences 23:1207-1220; Greiner et al, Arch. Biochem. Biophys., 303, 107-113, 1993; WO 1997/33976; WO 1997/48812, WO 1998/06856, WO 1998/028408, WO 2004/085638, WO 2006/037327, WO 2006/038062, WO 2006/063588, WO 2008/092901, WO 2008/116878, and WO 2010/034835.

A yeast phytase may be derived from genus *Saccharomyces* or *Schwanniomyces*, specifically species *Saccharomyces cerevisiae* or *Schwanniomyces occidentalis*. The former enzyme has been described as a Suitable yeast phytases are described in Nayini et al, 1984, Lebensmittel Wissenschaft and Technologie 17:24-26; Wodzinski et al, Adv. Appl. Microbiol., 42, 263-303; AU-A-24840/95;

Phytases from filamentous fungi may be derived from the fungal phylum of Ascomycota (ascomycetes) or the phylum Basidiomycota, e.g., the genus *Aspergillus, Thermomyces* (also called *Humicola*), *Myceliophthora, Manascus, Penicillium, Peniophora*, Agrocybe, *Paxillus*, or *Trametes*, specifically the species *Aspergillus terreus, Aspergillus niger, Aspergillus niger* var. *awamori, Aspergillus ficuum, Aspergillus fumigatus, Aspergillus oryzae, T. lanuginosus* (also known as *H. lanuginosa*), *Myceliophthora thermophila, Peniophora lycii, Agrocybe pediades, Manascus anka, Paxillus involtus*, or *Trametes pubescens*. Suitable fungal phytases are described in Yamada et al., 1986, Agric. Biol. Chem. 322:1275-1282; Piddington et al., 1993, Gene 133: 55-62; EP 684,313; EP 0 420 358; EP 0 684 313; WO 1998/28408; WO 1998/28409; JP 7-67635; WO 1998/44125; WO 1997/38096; WO 1998/13480.

In a preferred embodiment the phytase is derived from *Buttiauxella*, such as *Buttiauxella gaviniae, Buttiauxella agrestis*, or *Buttiauxella noackies*, such as the ones disclosed as SEQ ID NO: 2, SEQ ID NO: 4 and SEQ ID NO: 6, respectively, in WO 2008/092901.

In a preferred embodiment the phytase is derived from *Citrobacter*, such as *Citrobacter braakii*, such as one disclosed in WO 2006/037328.

Modified phytases or phytase variants are obtainable by methods known in the art, in particular by the methods disclosed in EP 897010; EP 897985; WO 99/49022; WO 99/48330, WO 2003/066847, WO 2007/112739, WO 2009/129489, and WO 2010/034835.

Commercially available phytase containing products include BIO-FEED PHYTASE™, PHYTASE NOVO™ CT or L (all from Novozymes), LIQMAX (DuPont) or RONOZYME™ NP, RONOZYME® HiPhos, RONOZYME® P5000 (CT), NATUPHOS™ NG 5000 (from DSM).

Carbohydrate-Source Generating Enzyme present and/or added during Saccharification and/or Fermentation According to the invention a carbohydrate-source generating enzyme, preferably a glucoamylase, is present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, Glucoamylase According to the invention the glucoamylase present and/or added during saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and 5436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In a preferred embodiment the glucoamylase used during saccharification and/or fermentation is the Talaromyces *emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulata, Pachykytospora papyracea*; and *Leucopaxillus giganteus* all disclosed in WO 2006/069289; and *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (SEQ ID NOs 2, 4 or 6), or from a strain of the genus *Gloephyllum*, in particular a strain of *Gloephyllum* as described in WO 2011/068803 (SEQ ID NO: 2, 4, 6, 8, 10, 12, 14 or 16) or a strain of the genus *Nigrofomes*, in particular a strain of *Nigrofomes* sp. disclosed in WO 2012/064351 (SEQ ID NO: 2) (all references hereby incorporated by reference). Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Genencor Int.).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NUB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

Cellulase or Cellulolytic Enzyme Composition Present and/or Added During Saccharification and/or Fermentation or SSF In a preferred embodiment of the invention a cellulase or cellulolytic enzyme composition is present and/or added during saccharification in step ii) and/or fermentation in step iii) or SSF.

The cellulase or cellulolytic enzyme composition may comprise one or more cellulolytic enzymes. The cellulase or cellulolytic enzyme composition may be of any origin. In a preferred embodiment the cellulase or cellulolytic enzyme composition comprises cellulolytic enzymes of fungal origin.

In an embodiment the cellulase or cellulolytic enzyme composition is derived from a strain of *Trichoderma*, such as *Trichoderma reesei*; or a strain of *Humicola*, such as *Humicola insolens*; or a strain of *Chrysosporium*, such as *Chrysosporium lucknowense*; or a strain of *Penicillium*, such as *Penicillium decumbens*. In a preferred embodiment the cellulolytic enzyme composition is derived from a strain of *Trichoderma reesei*.

The cellulase may be a beta-glucosidase, a cellobiohydrolase, and an endoglucanase or a combination thereof.

The cellulolytic enzyme composition may comprise a beta-glucosidase, a cellobiohydrolase, and an endoglucanase.

In an embodiment the cellulase or cellulolytic enzyme composition comprising one or more polypeptides selected from the group consisting of:

beta-glucosidase;
cellobiohydrolase I;
cellobiohydrolase II;
or a mixture thereof.

In a preferred embodiment the cellulase or cellulolytic enzyme composition further comprises a GH61 polypeptide having cellulolytic enhancing activity. Cellulolytic enhancing activity is defined and determined as described in WO 2011/041397 (incorporated by reference).

The term "GH61 polypeptide having cellulolytic enhancing activity" means a GH61 polypeptide that enhances the hydrolysis of a cellulosic material by enzymes having cellulolytic activity. For purposes of the present invention, cellulolytic enhancing activity may be determined by measuring the increase in reducing sugars or the increase of the total of cellobiose and glucose from hydrolysis of a cellulosic material by cellulolytic enzyme under the following conditions: 1-50 mg of total protein/g of cellulose in PCS (Pretreated Corn Stover), wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST™1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The cellulolytic enzyme composition may comprise a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (see SEQ ID NOs: 74 or 76), or *Aspergillus fumigatus*, such as one disclosed in SEQ ID NO: 2 in WO 2005/047499 or SEQ ID NO: 29 herein; or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*.

In an embodiment the beta-glucosidase is from a strain of *Aspergillus*, such as a strain of *Aspergillus fumigatus*, such as *Aspergillus fumigatus* beta-glucosidase (SEQ ID NO: 29 herein), or a variant thereof, which variant comprises one or more substitutions selected from the group consisting of L89M, G91L, F100D, I140V, I186V, S283G, N456E, and F512Y; such as a variant thereof with the following substitutions:

F100D+S283G+N456E+F512Y;
L89M+G91L+I186V+I140V;
I186V+L89M+G91L+I140V+F100D+S283G+N456E+F512Y.

The parent beta-glucosidase has at least 60% identity, such as at least 70%, such as at least 80%, such as at least 90%, such as at least 95%, such as at least 96%, such as at least 97%, such as at least 98%, such as at least 99%, such as 100% identity to the mature polypeptide of SEQ ID NO: 29 herein.

In case the beta-glucosidase is a beta-glucosidase variant it has at least 60% identity, such as at least 70%, such as at least 80%, such as at least 90%, such as at least 95%, such as at least 96%, such as at least 97%, such as at least 98%, such as at least 99%, but less than 100% identity to the mature polypeptide of SEQ ID NO: 29 herein.

In case the cellulolytic enzyme composition may comprise a GH61 polypeptide, it may be one derived from the genus *Thermoascus*, such as a strain of *Thermoascus aurantiacus*, such as the one described in WO 2005/074656 as SEQ ID NO: 2 or SEQ ID NO: 30 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 31 herein.

In a preferred embodiment the GH61 polypeptide, such as one derived from a strain of *Penicillium emersonii*, is selected from the group consisting of:
 (i) a GH61 polypeptide comprising the mature polypeptide of SEQ ID NO: 31 herein;
 (ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 31 herein.

In an embodiment the cellulolytic enzyme composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 6 in WO 2011/057140 or SEQ ID NO: 32 herein, or a strain of the genus *Trichoderma*, such as a strain of *Trichoderma reesei*.

In a preferred embodiment the cellobiohydrolase I, such as one derived from a strain of *Aspergillus fumigatus*, is selected from the group consisting of:
 (i) a cellobiohydrolase I comprising the mature polypeptide of SEQ ID NO: 32 herein;
 (ii) a cellobiohydrolase I comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 32 herein.

In an embodiment the cellulolytic enzyme composition comprises a cellobiohydrolase II (CBH II), such as one derived from a strain of the genus *Aspergillus*, such as a strain of *Aspergillus fumigatus*; such as the one disclosed as SEQ ID NO: 33 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In a preferred embodiment cellobiohydrolase II, such as one derived from a strain of *Aspergillus fumigatus*, is selected from the group consisting of:
 (i) a cellobiohydrolase II comprising the mature polypeptide of SEQ ID NO: 33 herein;
 (ii) a cellobiohydrolase II comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 33 herein.

In an embodiment the cellulolytic enzyme composition comprises a GH61 polypeptide having cellulolytic enhancing activity and a beta-glucosidase.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, and a beta-glucosidase.

In an embodiment the cellulolytic enzyme composition comprises a GH61 polypeptide having cellulolytic enhancing activity, a beta-glucosidase, and a CBH I.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, a beta-glucosidase, and a CBHI.

In an embodiment the cellulolytic enzyme composition comprises a GH61 polypeptide having cellulolytic enhancing activity, a beta-glucosidase, a CBHI, and a CBHII.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, a beta-glucosidase, a CBHI, and a CBHII.

In an embodiment the cellulolytic enzyme composition is a *Trichoderma reesei* cellulolytic enzyme composition, further comprising *Thermoascus aurantiacus* GH61A polypeptide (SEQ ID NO: 2 in WO 2005/074656 or SEQ ID NO: 30 herein), and *Aspergillus oryzae* beta-glucosidase fusion protein (WO 2008/057637).

In an embodiment the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein).

In an embodiment the cellulolytic enzyme composition is a *Trichoderma reesei* cellulolytic enzyme composition further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 29 herein, or a variant thereof, which variant has one of, preferably all of, the following substitutions: F100D, S283G, N456E, F512Y.

In an embodiment the cellulolytic enzyme composition comprises one or more of the following components:
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof.

In an embodiment the *Aspergillus fumigatus* beta-glucosidase (SEQ ID NO: 29 herein), comprises one or more substitutions selected from the group consisting of L89M, G91L, F100D, I140V, I186V, S283G, N456E, and F512Y; such as a variant thereof, with the following substitutions:
F100D+S283G+N456E+F512Y;
L89M+G91L+I186V+I140V; or
I186V+L89M+G91L+I140V+F100D+S283G+N456E+F512Y.

In an embodiment the cellulolytic enzyme composition further comprises the *Penicillium* sp. GH61 polypeptide shown in SEQ ID NO: 31 herein; or a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99%, such as 100% identity to the mature polypeptide of SEQ ID NO: 31 herein.

In an embodiment the cellulolytic enzyme composition comprising the following components:
(i) *Aspergillus fumigatus* cellobiohydrolase I shown in SEQ ID NO: 32 herein;
(ii) *Aspergillus fumigatus* cellobiohydrolase II shown in SEQ ID NO: 33 herein;
(iii) variant of *Aspergillus fumigatus* beta-glucosidase shown in SEQ ID NO: 29 with the following substitutions: F100D+S283G+N456E+F512Y; and
(iv) *Penicillium* sp. GH61 polypeptide shown in SEQ ID NO: 31 herein.

In an embodiment cellulolytic enzyme composition is dosed (i.e. during saccharification in step ii) and/or fermentation in step iii) or SSF) from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

Examples of Preferred Processes of the Invention

In a preferred embodiment the invention relates to a process for producing fermentation products from starch-containing material comprising the steps of:
i) liquefying the starch-containing material at a pH in the range between from above 4.0-6.5 at a temperature in the range from 70–100° C. using:
an alpha-amylase derived from *Bacillus stearothermophilus*;
an endoglucanase having a Melting Point (DSC) above 70° C.;
ii) saccharifying using a glucoamylase enzyme;
iii) fermenting using a fermenting organism.

In a preferred embodiment the process of the invention comprises the steps of:
i) liquefying the starch-containing material at a pH in the range between from above 4.5-6.2 at a temperature above the initial gelatinization temperature using:
an alpha-amylase, preferably derived from *Bacillus stearothermophilus*, having a T½ (min) at pH 4.5, 85° C., 0.12 mM CaCl$_2$ of at least 10;
an endoglucanase having a Melting Point (DSC) above 70° C.;
ii) saccharifying using a glucoamylase enzyme;
iii) fermenting using a fermenting organism.

In a preferred embodiment the process of the invention comprises the steps of:
i) liquefying the starch-containing material at a pH in the range between from above 4.0-6.5 at a temperature between 70-100° C.:
a bacterial alpha-amylase, preferably derived from *Bacillus stearothermophilus*, having a T½ (min) at pH 4.5, 85° C., 0.12 mM CaCl$_2$ of at least 10;
an endoglucanase having a Melting Point (DSC), between 70° C. and 95° C.;
optionally a protease, preferably derived from *Pyrococcus furiosus* or *Thermoascus aurantiacus*, having a thermostability value of more than 20% determined as Relative Activity at 80° C./70° C.;
ii) saccharifying using a glucoamylase enzyme;
iii) fermenting using a fermenting organism.

In a preferred embodiment the process of the invention comprises the steps of:
i) liquefying the starch-containing material at a pH in the range between from above 4.0-6.5 at a temperature above the initial gelatinization temperature using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
E129V+K177L+R179E+K220P+N224L+S242Q+Q254S;
V59A Q89R+E129V+K177L+R179E+Q254S+M284V (using SEQ ID NO: 1 herein for numbering);
an endoglucanase having a Melting Point (DSC), between 70° C. and 95° C.; such as an endoglucanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% to the mature part of the polypeptide of SEQ ID NOs: 3, 4, 5, 6, or 7;
optionally a protease having a thermostability value of more than 20% determined as Relative Activity at 80° C./70° C. derived from *Pyrococcus furiosus* and/or *Thermoascus aurantiacus*;
optionally a *Penicillium oxalicum* glucoamylase in SEQ ID NO: 14 herein having substitutions selected from the group of:
K79V;
K79V+P11F+T65A+Q327F; or
K79V+P2N+P4S+P11F+T65A+Q327F; (using SEQ ID NO: 14 for numbering);
ii) saccharifying using a glucoamylase enzyme;
iii) fermenting using a fermenting organism.

In a preferred embodiment the process of the invention comprises the steps of:
i) liquefying the starch-containing material at a pH in the range between from above 4.0-6.5 at a temperature between 70-100° C. using:
an alpha-amylase derived from *Bacillus stearothermophilus* having a double deletion I181+G182 and optional substitution N193F; and optionally further one of the following set of substitutions:

V59A+Q89R+E129V+K177L+R179E+H208Y+K220P+N224L+Q254S; or

V59A Q89R+E129V+K177L+R179E+Q254S+M284V (using SEQ ID NO: 1 herein (using SEQ ID NO: 1 herein for numbering);

an endoglucanase having a Melting Point (DSC), between 70° C. and 95° C., preferably having at least 90% identity to the mature part of the polypeptide of SEQ ID NO: 3;

a protease having a thermostability value of more than 20% determined as Relative Activity at 80° C./70° C. derived from *Pyrococcus furiosus* and/or *Thermoascus aurantiacus*; and optionally a *Penicillium oxalicum* glucoamylase in SEQ ID NO: 14 herein having substitutions selected from the group of:

K79V; or
K79V+P11F+T65A+Q327F; or
K79V+P2N+P4S+P11F+T65A+Q327F (using SEQ ID NO: 14 herein for numbering);

ii) saccharifying using a glucoamylase enzyme;
iii) fermenting using a fermenting organism.

In a preferred embodiment the process of the invention comprises the steps of:

i) liquefying the starch-containing material at a pH in the range between from above 4.0-6.5 at a temperature between 70-100° C. using:

an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
V59A Q89R+E129V+K177L+R179E+Q254S+M284V;
E129V+K177L+R179E+K220P+N224L+S242Q+Q254S (using SEQ ID NO: 1 herein for numbering).

an endoglucanase having a Melting Point (DSC), between 70° C. and 95° C., preferably having at least 90% identity to the mature part of the polypeptide of SEQ ID NO: 3;

a protease having a thermostability value of more than 20% determined as Relative Activity at 80° C./70° C. derived from *Pyrococcus furiosus;* a *Penicillium oxalicum* glucoamylase in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);

ii) saccharifying using a glucoamylase enzyme;
iii) fermenting using a fermenting organism.

In a preferred embodiment a cellulase or cellulolytic enzyme composition is present and/or added during fermentation or simultaneous saccharification and fermentation.

In a preferred embodiment a cellulase or cellulolytic enzyme composition derived from *Trichoderma reesei* is present and/or added during fermentation or simultaneous saccharification and fermentation (SSF).

In a preferred embodiment a cellulase or cellulolytic enzyme composition and a glucoamylase are present and/or added during fermentation or simultaneous saccharification and fermentation.

In an embodiment the cellulase or cellulolytic enzyme composition is derived from *Trichoderma reesei, Humicola insolens, Chrysosporium lucknowense* or *Penicillium decumbens.*

A Composition of the Invention

A composition of the invention comprises an alpha-amylase, such as a thermostable alpha-amylase, and an endoglucanase having a Melting Point (DSC) above 70° C.; optionally a protease, such as a thermostable protease. The composition may also further comprise a carbohydrate-source generating enzyme, in particular a glucoamylase, optionally a pullulanase and optionally a phytase too.

Therefore, in this aspect the invention relates to composition comprising:

i) an alpha-amylase;
ii) an endoglucanase having a Melting Point (DSC) above 70° C.;
iii) optionally a protease;
iv) optionally a carbohydrate-source generating enzyme.

Alpha-Amylase:

The alpha-amylase may be any alpha-amylase. In a preferred embodiment the alpha-amylase is a bacterial alpha-amylases, such as alpha-amylases derived from the genus *Bacillus*, such as *Bacillus stearomthermphilus*.

The alpha-amylase may be a thermostable alpha-amylase. The thermostable alpha-amylase may have a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the alpha-amylase is selected from the group of *Bacillus* stearomthermphilus alpha-amylase variants, in particular truncated to be 491 amino acids long, such as from 480 to 495 amino acids long, with mutations selected from the group of:
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 herein for numbering).

It should be understood that these alpha-amylases are only specific examples. Any alpha-amylase disclosed above in the "Alpha-Amylase Present and/or Added During Liquefaction"-section above may be used as the alpha-amylase component in a composition of the invention.

Endoglucanase:

According to the invention the endoglucanase component in the composition may be any endoglucanase having a Melting Point (DSC) above 70° C., such as between 70° C. and 95° C., determined using the "Differential Scanning calorimetry (DSC) Assay" described in the "Materials & Methods"—section below.

In an embodiment the endoglucanase has a Melting Point (DSC) above 72° C., such as above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In a preferred embodiment the endogluconase used in a process of the invention comprised in a composition opf the invention is a Glycoside Hydrolase Family 5 endoglucnase or GH5 endoglucanase (see the CAZy database on the "www.cazy.org" webpage. In an embodiment the GH5 endoglocianase is from family EG II, such as the *Talaromyces leycettanus* endoglucanase shown in SEQ ID NO: 3 herein; *Penicillium capsulatum* endoglucnase show in SEQ ID NO: 4 herein, and *Trichophaea saccata* endoglucnase shown in SEQ ID NO: 5 herein.

In an embodiment the endoglucanase is a family GH45 endoglucanase. In an embodiment the GH45 endoglocianase is from family EG V, such as the *Sordaria fimicola* shown in SEQ ID NO: 7 herein or *Thielavia terrestris* endogluncase shown in SEQ ID NO: 6 herein.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3 herein. In an embodiment the endoglucanase is derived from a strain of the genus *Talaromyces*, such as a strain of *Talaromyces leycettanus*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 4 herein, preferably derived from a strain of the genus *Penicillium*, such as a strain of *Penicillium capsulatum*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 5 herein, preferably derived from a strain of the genus *Trichophaea*, such as a strain of *Trichophaea saccata*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 6 herein, preferably derived from a strain of the genus *Thielavia*, such as a strain of *Thielavia terrestris*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 7, preferably derived from a strain of the genus *Sordaria*, such as a strain of *Sordaria fimicola*.

It should be understood that these endoglucanases are only specific examples. Any endoglucanase disclosed above in the "Thermostable Endoglucanase Present and/or Added During Liquefaction"-section above may be used as the endoglucoanase component in a composition of the invention.

In a preferred embodiment the endoglucanase has at least 90% identity to the mature part of the polypeptide of SEQ ID NO: 3 derived from a strain of *Talaromyces leycettanus* having a Melting Point (DSC) above 80° C.

Protease:

A composition of the invention may optionally comprise a protease, such as a thermosyable protease. There is no limitation on the origin of the protease component as long as it fulfills the thermostability properties defined herein.

In an embodiment the protease is of fungal origin. In an embodiment the protease is a metallo protease. In an embodiment the protease is derived from *Thermoascus aurantiacus* shown in SEQ ID NO: 2 herein.

In a preferred embodiment the protease is a variant of the *Thermoascus aurantiacus* protease mentioned above having a thermostability value of more than 20% determined as Relative Activity at 80° C./70° C. determined as described in Example 2.

In a specific preferred embodiment the protease is a variant of the metallo protease derived from *Thermoascus aurantiacus* disclosed as the mature part of SEQ ID NO: 2 disclosed in WO 2003/048353 or the mature part of SEQ ID NO: 1 in WO 2010/008841 or SEQ ID NO: 2 herein with mutations selected from the group of:

D79L+S87P+A112P+D142L;
D79L+S87P+D142L; and
A27K+D79L+Y82F+S87G+D104P+A112P+A126V+ D142L.

In another embodiment the protease is a bacterial protease. In another embodiment the protease is a serine protease. In a preferred embodiment the protease is derived from a strain of *Pyrococcus furiosus*, such as the one shown in SEQ ID NO: 1 in U.S. Pat. No. 6,358,726 or SEQ ID NO: 13 herein.

It should be understood that these proteases are only examples. Any protease disclosed above in the "Protease Present and/or Added During Liquefaction" section above may be used as the protease component in a composition of the invention.

Carbohydrate-Source Generating Enzymes:

A composition of the invention may optionally further comprise a carbohydrate-source generating enzyme, in particular a glucoamylase, such as a thermostable glucoamylase which has a heat stability at 85° C., pH 5.3, of at least 30%, preferably at least 35%.

Said carbohydrate-source generating enzyme may be a thermostable glucoamylase having a Relative Activity heat stability at 85° C. of at least 20%, at least 30%, preferably at least 35% determined as described in Example 4 (Heat stability).

In an embodiment the carbohydrate-source generating enzyme is a glucoamylase having a relative activity pH optimum at pH 5.0 of at least 90%, preferably at least 95%, preferably at least 97%, such as 100% determined as described in Example 4 (pH optimum).

In an embodiment the carbohydrate-source generating enzyme is a glucoamylase having a pH stability at pH 5.0 of at least at least 80%, at least 85%, at least 90% determined as described in Example 4 (pH stability).

In a preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum* disclosed as SEQ ID NO: 2 in WO 2011/127802 (which is hereby incorporated by reference), or a variant thereof, and shown in SEQ ID NO: 9 or 14 herein.

In an embodiment the glucoamylase, or a variant thereof, may have at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature polypeptide shown in SEQ ID NO: 2 in WO 2011/127802 or SEQ ID NO: 14 herein.

In a specific and preferred embodiment the carbohydrate-source generating enzyme is a variant of the *Penicillium oxalicum* glucoamylase disclosed as SEQ ID NO: 2 in WO 2011/127802 and shown in SEQ ID NO: 9 and 14 herein, having a K79V substitution (using the mature sequence shown in SEQ ID NO: 14 for numbering). The K79V glucoamylase variant has reduced sensitivity to protease degradation relative to the parent as disclosed in WO 2013/036526 (which is hereby incorporated by reference).

Examples of suitable thermostable *Penicillium oxalicum* glucoamylase variants are listed above and in Examples 17 and 18 below.

In an embodiment the carbohydrate-source generating enzyme, such as glucoamyase, such as *Penicillium oxalicum* glucoamylase, has pullulanase side-activity.

It should be understood that these carbohydrate-source generating enzymes, in particular glucoamylases, are only examples. Any carbohydrate-source generating enzyme disclosed above in the "Carbohydrate-source generating enzyme Present and/or Added During Liquefaction" section above may be used as component in a composition of the invention.

In a preferred embodiment the carbohydrate-source generating enzyme is the *Penicillium oxalicum* glucoamylase shown in SEQ ID NO: 14 herein or a sequence having at least 90% identity thereto further comprising a K79V substitution.

Pullulanase:

A composition of the invention may optionally further comprise a pullulanase. The pullulanase may be of any origin.

In an embodiment the pullulanase is of bacterial origin. In an embodiment the pullulanase is derived from a strain of *Bacillus* sp.

In an embodiment the pullulanase is a family GH57 pullulanase. In a preferred embodiment the pullulanase includes an X47 domain as disclosed in WO 2011/087836 (which are hereby incorporated by reference).

Specifically the pullulanase may be derived from a strain from the genus *Thermococcus*, including *Thermococcus litoralis* and *Thermococcus hydrothermalis* or a hybrid thereof.

The pullulanase may be *Thermococcus hydrothermalis* pullulanase shown in SEQ ID NO: 11 herein truncated at site X4 or a *Thermococcus hydrothermalis/T. litoralis* hybrid enzyme with truncation site X4 as disclosed in WO 2011/087836.

The another embodiment the pullulanase is one comprising an X46 domain disclosed in WO 2011/076123 (Novozymes).

It should be understood that these pullulanases are only specific examples. Any pullulanase disclosed above in the "Pullulanase Present and/or Added During Liquefaction"-section above may be used as the optional pullulanase component in a composition of the invention.

Phytase:

A composition of the invention may optionally further comprise a phytase. The phytase may be of any origin.

In an embodiment the phytase is of bacterial origin. In an embodiment the phytase is derived from a strain of from *Buttiauxella*, such as *Buttiauxella* gaviniae, such as the one disclosed as SEQ ID NO: 2 (amino acids 1-33 are expected signal peptide) in WO 2008/092901; or *Buttiauxella agrestis*, such as the one shown as SEQ ID NO: 4 (amino acids −9 to −1 are expected to be a part of the signal peptide) in WO 2008/092901; or *Buttiauxella noackies*, such as the one shown as SEQ ID NO: 6 in WO 2008/092901.

In another embodiment the phytase is derived from a strain of *Citrobacter*, such as a strain of *Citrobacter braakii*, such as ones disclosed as SEQ ID NOs: 2 or 4 in WO 2006/037328 (hereby incorporated by reference).

It should be understood that these phytases are only specific examples. Any phytase disclosed above in the "Phytase Present and/or Added During Liquefaction"-section above may be used as the optional pullulanase component in a composition of the invention.

In a preferred embodiment the phytase is derived from a strain of *Buttiauxella*.

Examples of Preferred Embodiments of the Composition of the Invention

In a preferred embodiment the composition of the invention comprises
  an alpha-amylase derived from *Bacillus stearothermophilus*;
  an endoglucanase having a Melting Point (DSC) above 70° C., such as between 70° C. and 95° C.;
  optionally a protease having a thermostability value of more than 20% determined as Relative Activity at 80° C./70° C. derived from *Pyrococcus furiosus* or *Thermoascus auranticus*; and
  optionally a glucoamylase, such as one derived from *Penicillium oxalicum*.

In another embodiment the composition of the invention comprises
  an alpha-amylase, preferably derived from *Bacillus stearothermophilus*, having a T½ (min) at pH 4.5, 85° C., 0.12 mM CaCl$_2$ of at least 10;
  an endoglucanase having a Melting Point (DSC) between 70° C. and 95° C.;
  a protease, preferably derived from *Pyrococcus furiosus* or *Thermoascus auranticus*, having a thermostability value of more than 20% determined as Relative Activity at 80° C./70° C.; and
  optionally a glucoamylase, e.g., derived from *Penicillium oxalicum*.

In another embodiment the composition of the invention comprises
  an alpha-amylase derived from *Bacillus stearothermophilus* having a double deletion I181+G182 and optionally substitution N193F; and optionally further one of the following set of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V; and
E129V+K177L+R179E+K220P+N224L+S242Q+Q254S (using SEQ ID NO: 1 herein for numbering);
an endoglucanase having a Melting Point (DSC) above 70° C.;
optionally a protease, preferably derived from *Pyrococcus furiosus* and/or *Thermoascus aurantiacus*, having a thermostability value of more than 20% determined as Relative Activity at 80° C./70° C.; and
optionally a *Penicillium oxalicum* glucoamylase in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+Y504T; or
K79V+P11F+T65A+Q327W+E501V+Y504T (using SEQ ID NO: 14 for numbering).

In an embodiment the *Bacillus stearothermophilus* alpha-amylase (SEQ ID NO: 1 herein), or a variant thereof, is the mature alpha-amylase or corresponding mature alpha-amylases having at least 80% identity, at least 90% identity, at least 95% identity at least 96% identity at least 97% identity at least 99% identity to the SEQ ID NO: 1 herein.

In an embodiment the endoglucoanase has a Melting Point (DSC) above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3, 4, 5, 6, or 7.

In an embodiment the endoglucanase has at least 80% identity to the mature part of the polypeptide of SEQ ID NO: 3 herein.

In an embodiment the endoglucanase has at least 90% identity to the mature part of the polypeptide of SEQ ID NO: 3 herein having a Melting Point (DSC) above 70° C.

In an embodiment the *Pyrococcus furiosus* protease (SEQ ID NO: 13 herein) and/or *Thermoascus aurantiacus* protease (SEQ ID NO: 2 herein), or a variant thereof, is the mature protease or corresponding mature protease having at least 80% identity, at least 90% identity, at least 95% identity at least 96% identity at least 97% identity at least 99% identity to the SEQ ID NO: 2 herein or SEQ ID NO: 13 herein, respectively.

In an embodiment 1 the *Penicillium oxalicum* glucoamylase (SEQ ID NO: 14 herein), or a variant thereof, is the mature glucoamylase or corresponding mature glucoamylase having at least 80% identity, at least 90% identity, at least 95% identity at least 96% identity at least 97% identity at least 99% identity to the SEQ ID NO: 14 herein.

Further Aspects of the Invention

In a further aspect of the invention it relates to the use of a composition of the invention for liquefying a starch-containing material.

In a final aspect of the invention is relates to methods of producing liquefied starch, comprising liquefying a starch-containing material with a composition of the invention.

Polypeptide with Endoglucoamase Activity from *Penicillium capsulatum* (SEQ ID NO: 4 Herein) and *Trichophaea saccata* (SEQ ID NO: 5 Herein)

In this aspect the invention relates to polypeptides having endoglucanase activity, selected from the group consisting of:

(a) a polypeptide having at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4;

(b) a fragment of the polypeptide of (a) that has endoglucanase activity.

In an embodiment the polypeptide comprises or consists of SEQ ID NO: 4 or the mature polypeptide of SEQ ID NO: 4. In another embodiment the mature polypeptide is amino acids 19 to 334 of SEQ ID NO: 4.

In another embodiment compositions comprising a polypeptide of the invention. In an embodiment the invention relates to polynucleotides encoding the polypeptide of the invention.

In an embodiment the invention relates to nucleic acid constructs or expression vectors comprising a polynucleotide of the invention operably linked to one or more control sequences that direct the production of the polypeptide in an expression host. The invention also relates to recombinant host cells comprising the polynucleotide of the invention 5 operably linked to one or more control sequences that direct the production of the polypeptide. Furthermore the invention relates to methods of producing a polypeptide of the invention, comprising:

(a) cultivating a cell, which in its wild-type form produces the polypeptide, under conditions conducive for production of the polypeptide; and (b) recovering the polypeptide.

The invention also relates to methods of producing a polypeptide having endoglucanase activity, comprising:

(a) cultivating the host cell of claim 7 under conditions conducive for production of the polypeptide; and (b) recovering the polypeptide.

In an embodiment the invention relates to transgenic plants, plant parts or plant cells comprising a polynucleotide encoding the polypeptide of the invention.

In an embodiment the invention relates to methods of producing a polypeptide having endoglucanase activity, comprising:

(a) cultivating the transgenic plant or plant cell of claim 10 under conditions conducive for production of the polypeptide; and (b) recovering the polypeptide.

In an embodiment the invention relates to methods of producing a protein, comprising:

(a) cultivating a recombinant host cell comprising a gene encoding a protein operably linked to the polynucleotide of the invention, wherein the gene is foreign to the polynucleotide encoding the signal peptide, under conditions conducive for production of the protein; and (b) recovering the protein.

The invention also relates to processes for degrading a cellulosic material, comprising: treating the cellulosic material with an enzyme composition in the presence of the polypeptide having endoglucanase activity of the invention.

In an embodiment the invention relates to processes for producing a fermentation product, such as ethanol, comprising:

(a) saccharifying a cellulosic material with an enzyme composition in the presence of the polypeptide having endoglucanase activity of the invention;

(b) fermenting the saccharified cellulosic material with one or more fermenting microorganisms to produce the fermentation product; and (c) recovering the fermentation product from the fermentation.

In an embodiment the invention relates to processes of fermenting a cellulosic material, comprising: fermenting the cellulosic material with one or more fermenting microorganisms, wherein the cellulosic material is saccharified with an enzyme composition in the presence of the polypeptide having endoglucanase activity of the invention. In an embodiment fermenting of the cellulosic material produces a fermentation product, such as ethanol.

In this aspect the invention relates to polypeptides having endoglucanase activity, selected from the group consisting of:

(a) a polypeptide having at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 5;

(b) a fragment of the polypeptide of (a) that has endoglucanase activity.

In an embodiment the polypeptide comprises or consists of SEQ ID NO: 5 or the mature polypeptide of SEQ ID NO: 5. The mature polypeptide is amino acids 21 to 394 of SEQ ID NO: 5.

In an embodiment the invention relates to compositions comprising the polypeptide of the invention.

In an embodiment the invention relates to polynucleotides encoding the polypeptides of the invention. In an embodiment the invention relates to nucleic acid constructs or expression vectors comprising a polynucleotide of the invention operably linked to one or more control sequences that direct the production of the polypeptide in an expression host.

In an embodiment the invention relates to recombinant host cells comprising the polynucleotide of claim 5 operably linked to one or more control sequences that direct the production of the polypeptide.

In an embodiment the invention relates to methods of producing the polypeptide of the invention:

(a) cultivating a cell, which in its wild-type form produces the polypeptide, under conditions conducive for production of the polypeptide; and (b) recovering the polypeptide.

In an embodiment the invention relates to methods of producing a polypeptide having endoglucanase activity, comprising:

(a) cultivating the host cell of the invention under conditions conducive for production of the polypeptide; and (b) recovering the polypeptide.

In an aspect the invention also relates to transgenic plants, plant parts or plant cells comprising a polynucleotide encoding the polypeptide of the invention.

In an embodiment the invention relates to method of producing a polypeptides having endoglucanase activity, comprising:

(a) cultivating the transgenic plant or plant cell of the invention under conditions conducive for production of the polypeptide; and (b) recovering the polypeptide.

The invention also relates to methods of producing a protein, comprising:

(a) cultivating a recombinant host cell comprising a gene encoding a protein operably linked to the polynucleotide of the invention, wherein the gene is foreign to the polynucleotide encoding the signal peptide, under conditions conducive for production of the protein; and (b) recovering the protein.

In an embodiment the invention relates to processes for degrading a cellulosic material, comprising: treating the cellulosic material with an enzyme composition in the presence of the polypeptide having endoglucanase activity of the invention.

In the invention also relates to processes for producing a fermentation product, such as ethanol, comprising:

(a) saccharifying a cellulosic material with an enzyme composition in the presence of the polypeptide having endoglucanase activity of any of claims 1-3;

(b) fermenting the saccharified cellulosic material with one or more fermenting microorganisms to produce the fermentation product; and (c) recovering the fermentation product from the fermentation.

In an embodiment the invention relates to processes of fermenting a cellulosic material, comprising: fermenting the cellulosic material with one or more fermenting microorganisms, wherein the cellulosic material is saccharified with an enzyme composition in the presence of the polypeptide having endoglucanase activity of the invention.

Finally the invention relates to processes wherein fermenting of the cellulosic material produces a fermentation product.

Materials & Methods

Materials: Alpha-Amylase 369 (AA369):

*Bacillus stearothermophilus* alpha-amylase with the mutations: I181*+G182*+N193F+V59A+Q89R+E129V+K177L+R179E+Q254S+M284V truncated to 491 amino acids (SEQ ID NO: 1 herein).

Endoglucanase TL (EG TL):

Endoglucoanase GH5 from *Talaromyces leycettanus* disclosed in WO2013/019780 as SEQ ID NO: 2 and SEQ ID NO: 3 herein. (P23YSQ).

Endoglucanase PC (EG PC):

Endoglucoanase GH5 from *Penicillium capsulatum* disclosed as SEQ ID NO: 4 herein. (P244HZ)

Endoglucanase TS (EG TS):

Endoglucoanase GH5 from *Trichophaea saccata* disclosed as SEQ ID NO: 5 herein. (P2PJ)

Endoglucanase TT (EG TT):

Endoglucoanase GH45 from *Thielavia terrestris* disclosed in SEQ ID NO: 6 herein. (P24PYU)

Endoglucanase SF (EG SF):

Endoglucoanase GH45 from *Sordaria fimicola* disclosed in co-pending application PCT/CN2012/080220 as SEQ ID NO: 2 and SEQ ID NO: 7 herein (P2CF).

Protease 196:

(JTP196) Metallo protease derived from *Thermoascus aurantiacus* CGMCC No. 0670 disclosed as amino acids 1-177 in SEQ ID NO: 2 herein and amino acids 1-177 in SEQ ID NO: 2 in WO 2003/048353 with the following mutations: A27K+D79L+Y82F+S87G+D104P+A112P+A126V+D142L.

Protease Pfu:

Protease derived from *Pyrococcus furiosus* purchased from Takara Bio (Japan) as Pfu Protease S (activity 10.5 mg/mL) and also shown in SEQ ID NO: 13 herein.

Glucoamylase PO:

Mature part of the *Penicillium oxalicum* glucoamylase disclosed as SEQ ID NO: 2 in WO 2011/127802 and shown in SEQ ID NO: 9 herein.

Glucoamylase PE001:

Variant of the *Penicillium oxalicum* glucoamylase having a K79V substitution using the mature sequence shown in SEQ ID NO: 14 for numbering.

Glucoamyase AC:

Blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290 as side activities; and cellulolytic enzyme composition comprising GH61A polypeptide having cellulolytic enhancing activity derived from a strain of *Penicillium emersonii* (SEQ ID NO: 2 in WO 2011/041397), *Aspergillus fumigatus* beta-glucosidase (SEQ ID NO: 2 in WO 2005/047499) variant F100D, S283G, N456E, F512Y disclosed in WO 2012/044915; *Aspergillus fumigatus* Cel7A CBH1 disclosed as SEQ ID NO: 6 in WO2011/057140; and *Aspergillus fumigatus* CBH II disclosed as SEQ ID NO: 18 in WO 2011/057140.

Yeast:

RED STAR ETHANOL RED™ available from Red Star/Lesaffre, USA.

Methods

Determination of Td by Differential Scanning Calorimetry for Endoglucanases.

The thermostability of an enzyme is determined by Differential Scanning calorimetry (DSC) using a VP-Capillary Differential Scanning calorimeter (MicroCal Inc., Piscataway, N.J., USA). The thermal denaturation temperature, Td (° C.), is taken as the top of denaturation peak (major endothermic peak) in thermograms (Cp vs. T) obtained after heating enzyme solutions (approx. 0.5 mg/ml) in buffer (50 mM acetate, pH 5.0) at a constant programmed heating rate of 200 K/hr.

Sample- and reference-solutions (approx. 0.2 ml) are loaded into the calorimeter (reference: buffer without enzyme) from storage conditions at 10° C. and thermally pre-equilibrated for 20 minutes at 20° C. prior to DSC scan from 20° C. to 120° C. Denaturation temperatures are determined at an accuracy of approximately +/−1° C.

Identity:

The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLO-SUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Protease Assays

AZCL-Casein Assay

A solution of 0.2% of the blue substrate AZCL-casein is suspended in Borax/NaH$_2$PO$_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in 0D405 at room temperature is monitored as a measure of the protease activity.

Glucoamylase Activity (AGU) Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |

-continued

| Color reaction: | |
|---|---|
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Alpha-Amylase Activity (KNU-A)

A folder EB-SM-5091.02-D on determining KNU-A activity is available upon request to Novozymes A/S, Denmark, which folder is hereby included by reference.

Alpha-Amylase Activity KNU(S)

BS-amylase in samples and the enzyme alpha-glucosidase in the reagent kit hydrolyze substrate (4,6-ethylidene(G7)-p-nitrophenyl(G1)-alpha-D-maltoheptaoside (ethylidene-G7PNP)) to glucose and the yellow-colored p-nitrophenol.

The rate of formation of p-nitrophenol can be observed by Konelab 30. This is an expression of the reaction rate and thereby the enzyme activity.

Reaction Conditions
Reaction:
pH 7.15
Temperature 37° C.
Reaction Time 180 sec
Detection
Wavelength 405 nm
Measuring Time 120 sec
Unit Definition

*Bacillus stearothermophilus* amylase (BS-amylase) activity is measured in KNU(S), Kilo Novo Units (sterarothermophilus), relative to an enzyme standard of a declared strength.

This analytical method is described in more details in EB-SM-0221.02 (incorporated by reference) available from Novozymes A/S, Denmark, on request.

Determination of FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

| Substrate | Soluble starch |
|---|---|
| Temperature | 37° C. |
| pH | 4.7 |
| Reaction time | 7-20 minutes |

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novozymes A/S, glucoamylase wildtype *Aspergillus niger* G1, also disclosed in Boel et al. (1984), EMBO J. 3 (5), p. 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

| | Alpha-amylase | |
|---|---|---|
| Starch + Iodine | → | Dextrins + Oligosaccharides |
| | 40° C., pH 2.5 | |
| Blue/violet | t = 23 sec. | Decoloration |

Standard Conditions/Reaction Conditions: (Per Minute)

| Substrate: | Starch, approx. 0.17 g/L |
|---|---|
| Buffer: | Citate, approx. 0.03M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | lambda = 590 nm |
| Enzyme concentration: | 0.025 AFAU/mL |
| Enzyme working range: | 0.01-0.04 AFAU/mL |

If further details are preferred these can be found in EB-SM-0259.02/01 available on request from Novozymes A/S, and incorporated by reference.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

EXAMPLES

Example 1

Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 1 herein for numbering)) and alpha-amylase variants thereof was determined by incubating the reference alpha-amylase and variants at pH 4.5 and 5.5 and temperatures of 75° C. and 85° C. with 0.12 mM $CaCl_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM $CaCl_2$, pH 5.0). Twenty microliters enzyme sample was transferred to 48-well PCR MTP and 180 microliters stability buffer (150 mM acetate, 150 mM MES, 0.01% Triton X100, 0.12 mM $CaCl_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM $CaCl_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½ (min)) was calculated using the equation: T½ (min)=T(min)*LN(0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM $CaCl_2$) | T½ (min) (pH 4.5, 85° C., 0.12 mM $CaCl_2$) | T½ (min) (pH 5.5, 85° C., 0.12 mM $CaCl_2$) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A with the substitutions V59A + E129V + K177L + R179E + K220P + N224L + S242Q + Q254S | >180 | 49 | >480 |
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |
| Reference Alpha-Amylase A with the substitution M284T | 35 | 7 | 278 |
| Reference Alpha-Amylase A with the substitutions M284V | 59 | 13 | ND |

ND not determined

The results demonstrate that the alpha-amylase variants have a significantly greater half-life and stability than the reference alpha-amylase.

Example 2

Preparation of Protease Variants and Test of Thermostability

Strains and Plasmids

*E. coli* DH12S (available from Gibco BRL) was used for yeast plasmid rescue. pJTP000 is a *S. cerevisiae* and *E. coli* shuttle vector under the control of TPI promoter, constructed from pJC039 described in WO 01/92502, in which the *Thermoascus aurantiacus* M35 protease gene (WO 03/048353) has been inserted.

*Saccharomyces cerevisiae* YNG318 competent cells: MATa Dpep4[cir+] ura3-52, leu2-D2, his 4-539 was used for protease variants expression. It is described in J. Biol. Chem. 272 (15), pp 9720-9727, 1997.

Media and Substrates

10× Basal Solution:

Yeast nitrogen base w/o amino acids (DIFCO) 66.8 g/l, succinate 100 g/l, NaOH 60 g/l.

Sc-Glucose:

20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar (2%) and H$_2$O (approx. 761 ml) is autoclaved together, and the separately sterilized SC-glucose solution is added to the agar solution.

YPD:

Bacto peptone 20 g/l, yeast extract 10 g/l, 20% glucose 100 ml/l.

YPD+Zn:

YPD+0.25 mM ZnSO$_4$.

Peg/Liac Solution:

40% PEG4000 50 ml, 5 M Lithium Acetate 1 ml.

96 Well Zein Micro Titre Plate:

Each well contains 200 microL of 0.05-0.1% of zein (Sigma), 0.25 mM ZnSO$_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (Eds.).

Yeast Transformation

Yeast transformation was performed using the lithium acetate method. 0.5 microL of vector (digested by restriction endnucleases) and 1 microL of PCR fragments is mixed. The DNA mixture, 100 microL of YNG318 competent cells, and 10 microL of YEAST MAKER carrier DNA (Clontech) is added to a 12 ml polypropylene tube (Falcon 2059). Add 0.6 ml PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The *Themoascus* M35 protease gene was amplified with the primer pair Prot F (SEQ ID NO: 15 herein) and Prot R (SEQ ID NO: 16 herein). The resulting PCR fragments were introduced into *S. cerevisiae* YNG318 together with the pJC039 vector (described in WO2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 17 herein) and AM35 (SEQ ID NO: 18 herein) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL H$_2$O | 1 | 94° C. 2 min |
| 2 beads puRe Taq Ready-To-Go PCR (Amersham Biosciences) | 2 | 94° C. 30 sec |
| 0.5 micro L × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex. 60° C. and 65° C., 70° C. and 75° C., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml of 12.5% azo-casein in ethanol in 96 ml of 20 mM sodium acetate, pH 4.5, containing 0.01% triton-100 and 0.25 mM ZnSO$_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al. (2001), *Appl. Environ. Microbiol.* 67, 4701-4707. For each of the constructs 10-20 strains were isolated, purified and cultivated in shake flasks.

Purification of Expressed Variants

1. Adjust pH of the 0.22 μm filtered fermentation sample to 4.0.
2. Put the sample on an ice bath with magnetic stirring. Add (NH4)2SO4 in small aliquots (corresponding to approx. 2.0-2.2 M (NH4)2SO4 not taking the volume increase into account when adding the compound).
3. After the final addition of (NH4)2SO4, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 ml 50 mM Na-acetate pH 4.0.
6. Filter the sample by vacuum suction using a 0.22 μm PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. # PRAK 11/08).
2. With stirring, 250 microL of substrate solution is transferred to a 1.5 ml Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

Results

TABLE 2

Relative activity of protease variants. Numbering of substitution(s) starts from N-terminal of the mature peptide in amino acids 1 to 177 of SEQ ID NO: 2 herein.

| Variant | Substitution(s) | Relative activity 65° C./60° C. |
|---|---|---|
| WT | none | 31% |
| JTP004 | S87P | 45% |
| JTP005 | A112P | 43% |
| JTP008 | R2P | 71% |
| JTP009 | D79K | 69% |
| JTP010 | D79L | 75% |
| JTP011 | D79M | 73% |
| JTP012 | D79L/S87P | 86% |
| JTP013 | D79L/S87P/A112P | 90% |
| JTP014 | D79L/S87P/A112P | 88% |
| JTP016 | A73C | 52% |
| JTP019 | A126V | 69% |
| JTP021 | M152R | 59% |

TABLE 3

Relative activity of protease variants. Numbering of substitution(s) starts from N-terminal of the mature peptide in amino acids 1 to 177 of SEQ ID NO: 2 herein.

| Variant | Substitution(s) and/or deletion (S) | 70° C./65° C. | 75° C./65° C. | 75° C./70° C. |
|---|---|---|---|---|
| WT | none | 59% | 17% | |
| JTP036 | D79L/S87P/D142L | 73% | 73% | |
| JTP040 | T54R/D79L/S87P | | 71% | |
| JTP042 | Q53K/D79L/S87P/I173V | | 108% | |
| JTP043 | Q53R/D79L/S87P | | 80% | |
| JTP045 | S41R/D79L/S87P | | 82% | |
| JTP046 | D79L/S87P/Q158W | | 96% | |
| JTP047 | D79L/S87P/S157K | | 85% | |
| JTP048 | D79L/S87P/D104R | | 88% | |
| JTP050 | D79L/S87P/A112P/D142L | | 88% | |
| JTP051 | S41R/D79L/S87P/A112P/D142L | | | 102% |
| JTP052 | D79L/S87P/A112P/D142L/S157K | | | 111% |
| JTP053 | S41R/D79L/S87P/A112P/D142L/S157K | | | 113% |
| JTP054 | ΔS5/D79L/S87P | | 92% | |
| JTP055 | ΔG8/D79L/S87P | | 95% | |
| JTP059 | C6R/D79L/S87P | | 92% | |
| JTP061 | T46R/D79L/S87P | | 111% | |
| JTP063 | S49R/D79L/S87P | | 94% | |
| JTP064 | D79L/S87P/N88R | | 92% | |
| JTP068 | D79L/S87P/T114P | | 99% | |
| JTP069 | D79L/S87P/S115R | | 103% | |
| JTP071 | D79L/S87P/T116V | | 105% | |

TABLE 3-continued

Relative activity of protease variants. Numbering of substitution(s) starts from N-terminal of the mature peptide in amino acids 1 to 177 of SEQ ID NO: 2 herein.

| Variant | Substitution(s) and/or deletion (S) | 70° C./65° C. | 75° C./65° C. | 75° C./70° C. |
|---|---|---|---|---|
| JTP072 | N26R/D79L/S87P | | 92% | |
| JTP077 | A27K/D79L/S87P/A112P/D142L | | | 106% |
| JTP078 | A27V/D79L/S87P/A112P/D142L | | | 100% |
| JTP079 | A27G/D79L/S87P/A112P/D142L | | | 104% |

TABLE 4

Relative activity of protease variants. Numbering of substitution(s) starts from N-terminal of the mature peptide in amino acids 1 to 177 of SEQ ID NO: 2 herein.

| Variant | Substitution(s) and/or deletion(s) | Relative activity 75° C./65° C. | Remaining activity 80° C. | Remaining activity 84° C. |
|---|---|---|---|---|
| JTP082 | ΔS5/D79L/S87P/A112P/D142L | 129% | | 53% |
| JTP083 | T46R/D79L/S87P/A112P/D142L | 126% | | |
| JTP088 | Y43F/D79L/S87P/A112P/D142L | 119% | | |
| JTP090 | D79L/S87P/A112P/T124L/D142L | 141% | | |
| JTP091 | D79L/S87P/A112P/T124V/D142L | 154% | 43% | |
| JTP092 | ΔS5/N26R/D79L/S87P/A112P/D142L | | | 60% |
| JTP095 | N26R/T46R/D79L/S87P/A112P/D142L | | | 62% |
| JTP096 | T46R/D79L/S87P/T116V/D142L | | | 67% |
| JTP099 | D79L/P81R/S87P/A112P/D142L | | | 80% |
| JTP101 | A27K/D79L/S87P/A112P/T124V/D142L | | 81% | |
| JTP116 | D79L/Y82F/S87P/A112P/T124V/D142L | | 59% | |
| JTP117 | D79L/Y82F/S87P/A112P/T124V/D142L | | 94% | |
| JTP127 | D79L/S87P/A112P/T124V/A126V/D142L | | 53% | |

TABLE 5

Relative activity of protease variants. Numbering of substitution(s) starts from N-terminal of the mature peptide in amino acids 1 to 177 of SEQ ID NO: 2 herein.

| Variant | Substitutions | 75° C./70° C. | 80° C./70° C. | 85° C./70° C. |
|---|---|---|---|---|
| JTP050 | D79L S87P A112P D142L | 55% | 23% | 9% |
| JTP134 | D79L Y82F S87P A112P D142L | | 40% | |
| JTP135 | S38T D79L S87P A112P A126V D142L | | 62% | |
| JTP136 | D79L Y82F S87P A112P A126V D142L | | 59% | |
| JTP137 | A27K D79L S87P A112P A126V D142L | | 54% | |
| JTP140 | D79L S87P N98C A112P G135C D142L | 81% | | |
| JTP141 | D79L S87P A112P D142L T141C M161C | 68% | | |
| JTP143 | S36P D79L S87P A112P D142L | 69% | | |
| JTP144 | A37P D79L S87P A112P D142L | 57% | | |
| JTP145 | S49P D79L S87P A112P D142L | 82% | 59% | |
| JTP146 | S50P D79L S87P A112P D142L | 83% | 63% | |
| JTP148 | D79L S87P D104P A112P D142L | 76% | 64% | |
| JTP161 | D79L Y82F S87G A112P D142L | | 30% | 12% |

TABLE 5-continued

Relative activity of protease variants. Numbering of substitution(s) starts from N-terminal of the mature peptide in amino acids 1 to 177 of SEQ ID NO: 2 herein.

| Variant | Substitutions | Relative activity 75° C./70° C. | 80° C./70° C. | 85° C./70° C. |
|---|---|---|---|---|
| JTP180 | S70V D79L Y82F S87G Y97W A112P D142L | 52% | | |
| JTP181 | D79L Y82F S87G Y97W D104P A112P D142L | 45% | | |
| JTP187 | S70V D79L Y82F S87G A112P D142L | 45% | | |
| JTP188 | D79L Y82F S87G D104P A112P D142L | 43% | | |
| JTP189 | D79L Y82F S87G A112P A126V D142L | 46% | | |
| JTP193 | Y82F S87G S70V D79L D104P A112P D142L | | | 15% |
| JTP194 | Y82F S87G D79L D104P A112P A126V D142L | | | 22% |
| JTP196 | A27K D79L Y82F S87G D104P A112P A126V D142L | | | 18% |

TABLE 6

Relative activity of protease variants. Numbering of substitution(s) starts from N-terminal of the mature peptide in amino acids 1 to 177 of SEQ ID NO: 2 herein.

| Variant | Substitutions | Relative activity 75° C./70° C. | 80° C./70° C. |
|---|---|---|---|
| JTP196 | A27K D79L Y82F S87G D104P A112P A126V D142L | 102% | 55% |
| JTP210 | A27K Y82F S87G D104P A112P A126V D142L | 107% | 36% |
| JTP211 | A27K D79L Y82F D104P A112P A126V D142L | 94% | 44% |
| JTP213 | A27K Y82F D104P A112P A126V D142L | 103% | 37% |

Example 3

Temperature Profile of Selected Variants Using Purified Enzymes

Selected variants showing good thermo-stability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:

1) Mix 10 microliters of 10 micrograms/ml enzyme solutions and 100u1 of 0.025% zein solution in a micro titer plate (MTP).

2) Incubate at various temperatures for 60 min.

3) Add 10 microliters of 100% trichloroacetic acid (TCA) solution.

4) Centrifuge MTP at 3500 rpm for 5 min.

5) Take out 15 microliters to a new MTP containing 100 microliters of BCA assay solution (Pierce Cat#:23225, BCA Protein Assay Kit).

6) Incubate for 30 min. at 60° C.

7) Measure A562.

The results are shown in Table 7. All of the tested variants showed an improved thermo-stability as compared to the wt protease.

TABLE 7

Zein-BCA assay

Sample incubated 60 min at indicated temperatures (° C.)
(μg/ml Bovine serum albumin equivalent peptide released)

| WT/Variant | 60° C. | 70° C. | 75° C. | 80° C. | 85° C. | 90° C. | 95° C. |
|---|---|---|---|---|---|---|---|
| WT | 94 | 103 | 107 | 93 | 58 | 38 | |
| JTP050 | 86 | 101 | 107 | 107 | 104 | 63 | 36 |
| JTP077 | 82 | 94 | 104 | 105 | 99 | 56 | 31 |
| JTP188 | 71 | 83 | 86 | 93 | 100 | 75 | 53 |
| JTP196 | 87 | 99 | 103 | 106 | 117 | 90 | 38 |

Example 4

Characterization of *Penicillium oxalicum* Glucoamylase

The *Penicillium oxalicum* glucoamylase is disclosed in SEQ ID NOs: 9 and 14 (mature) herein.

Substrate.

Substrate: 1% soluble starch (Sigma S-9765) in deionized water Reaction buffer: 0.1M Acetate buffer at pH 5.3

Glucose concentration determination kit: Wako glucose assay kit (LabAssay glucose, WAKO, Cat#298-65701).

Reaction Condition.

20 microL soluble starch and 50 microL acetate buffer at pH 5.3 were mixed. 30 microL enzyme solution (50 micro g enzyme protein/ml) was added to a final volume of 100 microL followed by incubation at 37° C. for 15 min.

The glucose concentration was determined by Wako kits.

All the work carried out in parallel.

Temperature Optimum.

To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 8.

TABLE 8

| Temperature optimum | | | | | | | | | | |
|---|---|---|---|---|---|---|---|---|---|---|
| Temperature (° C.) | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat Stability.

To assess the heat stability of the *Penicillium oxalicum* glucoamylase the Reaction condition assay was modified in that the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 9.

TABLE 9

| Heat stability | | | | | | | | | | |
|---|---|---|---|---|---|---|---|---|---|---|
| Temperature (° C.) | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH Optimum.

To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 10.

TABLE 10

| pH optimum | | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH Stability.

To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 11.

TABLE 11

| pH stability | | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5

Thermostability of Protease Pfu.

The thermostability of the *Pyrococcus furiosus* protease (Pfu S) purchased from Takara Bio Inc, (Japan) was tested using the same methods as in Example 2. It was found that the thermostability (Relative Activity) was 110% at (80° C./70° C.) and 103% (90° C./70° C.) at pH 4.5.

Example 6

Cloning of *Penicillium oxalicum* Strain Glucoamylase Gene

Preparation of *Penicillium oxalicum* Strain cDNA.

The cDNA was synthesized by following the instruction of 3' Rapid Amplification of cDNA End System (Invitrogen Corp., Carlsbad, Calif., USA).

Cloning of *Penicillium oxalicum* Strain Glucoamylase Gene.

The *Penicillium oxalicum* glucoamylase gene was cloned using the oligonucleotide primer shown below designed to amplify the glucoamylase gene from 5' end.

```
                                     (SEQ ID NO: 19)
Sense primer:  5'-ATGCGTCTCACTCTATTATCAGGTG-3'
```

The full length gene was amplified by PCR with Sense primer and AUAP (supplied by 3' Rapid Amplification of cDNA End System) by using Platinum HIFI Taq DNA polymerase (Invitrogen Corp., Carlsbad, Calif., USA). The amplification reaction was composed of 5 µl of 10× PCR buffer, 2 µl of 25 mM $MgCl_2$, 1 µl of 10 mM dNTP, 1 µl of 10 uM Sense primer, 1 µl of 10 uM AUAP, 2 µl of the first strand cDNA, 0.5 µl of HIFI Taq, and 37.5 µl of deionized water. The PCR program was: 94° C., 3 mins; 10 cycles of 94° C. for 40 secs, 60° C. 40 secs with 1° C. decrease per cycle, 68° C. for 2 min; 25 cycles of 94° C. for 40 secs, 50° C. for 40 secs, 68° C. for 2 min; final extension at 68° C. for 10 mins.

The obtained PCR fragment was cloned into pGEM-T vector (Promega Corporation, Madison, Wis., USA) using a pGEM-T Vector System (Promega Corporation, Madison, Wis., USA) to generate plasmid AMG 1. The glucoamylase gene inserted in the plasmid AMG 1 was sequencing confirmed. *E. coli* strain TOP10 containing plasmid AMG 1 (designated NN059173), was deposited with the Deutsche Sammlung von Mikroorganismen und Zellkulturen GmbH (DSMZ) on Nov. 23, 2009, and assigned accession number as DSM 23123.

Example 7

Expression of Cloned *Penicillium oxalicum* Glucoamylase

The *Penicillium oxalicum* glucoamylase gene was re-cloned from the plasmid AMG 1 into an *Aspergillus* expression vector by PCR using two cloning primer F and primer R shown below, which were designed based on the known sequence and added tags for direct cloning by IN-FUSION™ strategy.

```
Primer F:
                                     (SEQ ID NO: 20)
5' ACACAACTGGGGATCCACCATGCGTCTCACTCTATTATC Primer R:
                                     (SEQ ID NO: 21)
5' AGATCTCGAGAAGCTTAAAACTGCCACACGTCGTTGG
```

A PCR reaction was performed with plasmid AMG 1 in order to amplify the full-length gene. The PCR reaction was composed of 40 µg of the plasmid AMG 1 DNA, 1 µl of each primer (100 µM); 12.5 µl of 2× Extensor Hi-Fidelity master mix (Extensor Hi-Fidelity Master Mix, ABgene, United Kingdom), and 9.5 µl of PCR-grade water. The PCR reaction was performed using a DYAD PCR machine (Bio-Rad Laboratories, Inc., Hercules, Calif., USA) programmed for 2 minutes at 94° C. followed by a 25 cycles of 94° C. for 15 seconds, 50° C. for 30 seconds, and 72° C. for 1 minute; and then 10 minutes at 72° C.

The reaction products were isolated by 1.0% agarose gel electrophoresis using 1×TAE buffer where an approximately 1.9 kb PCR product band was excised from the gel and purified using a GFX® PCR DNA and Gel Band Purification Kit (GE Healthcare, United Kingdom) according to manufacturer's instructions. DNA corresponding to the *Penicillium oxalicum* glucoamylase gene was cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

A 2 µl volume of the ligation mixture was used to transform 25 µl of Fusion Blue *E. coli* cells (included in the IN-FUSION™ Dry-Down PCR Cloning Kit). After a heat shock at 42° C. for 45 sec, and chilling on ice, 250 µl of SOC medium was added, and the cells were incubated at 37° C. at 225 rpm for 90 min before being plated out on LB agar plates containing 50 µg of ampicillin per ml, and cultivated overnight at 37° C. Selected colonies were inoculated in 3 ml of LB medium supplemented with 50 µg of ampicillin per ml and incubated at 37° C. at 225 rpm overnight.

Plasmid DNA from the selected colonies was purified using Mini JETSTAR (Genomed, Germany) according to the manufacturer's instructions. *Penicillium oxalicum* glucoamylase gene sequence was verified by Sanger sequencing before heterologous expression. One of the plasmids was selected for further expression, and was named XYZ XYZ1471-4.

Protoplasts of *Aspergillus niger* MBin118 were prepared as described in WO 95/02043. One hundred μl of protoplast suspension were mixed with 2.5 μg of the XYZ1471-4 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 6% low melting agarose (Biowhittaker Molecular Applications) in COVE sucrose (Cove, 1996, Biochim. Biophys. Acta 133:51-56) (1M) plates supplemented with 10 mM acetamide and 15 mM CsCl and added as a top layer on COVE sucrose (1M) plates supplemented with 10 mM acetamide and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE (Sodium dodecyl sulfate-polyacrylamide gel electrophoresis) gel, Griton XT Precast gel (BioRad, CA, USA) in order to identify the best transformants based on the ability to produce large amount of glucoamylase. A selected transformant was identified on the original transformation plate and was preserved as spores in a 20% glycerol stock and stored frozen (−80° C.).

Cultivation.

The selected transformant was inoculated in 100 ml of MLC media and cultivated at 30° C. for 2 days in 500 ml shake flasks on a rotary shaker. 3 ml of the culture broth was inoculated to 100 ml of M410 medium and cultivated at 30° C. for 3 days. The culture broth was centrifuged and the supernatant was filtrated using 0.2 μm membrane filters.

Alpha-Cyclodextrin Affinity Gel.

Ten grams of Epoxy-activated Sepharose 6B (GE Healthcare, Chalfont St. Giles, U.K) powder was suspended in and washed with distilled water on a sintered glass filter. The gel was suspended in coupling solution (100 ml of 12.5 mg/ml alpha-cyclodextrin, 0.5 M NaOH) and incubated at room temperature for one day with gentle shaking. The gel was washed with distilled water on a sintered glass filter, suspended in 100 ml of 1 M ethanolamine, pH 10, and incubated at 50° C. for 4 hours for blocking. The gel was then washed several times using 50 mM Tris-HCl, pH 8 and 50 mM NaOAc, pH 4.0 alternatively. The gel was finally packed in a 35-40 ml column using equilibration buffer (50 mM NaOAc, 150 mM NaCl, pH 4.5).

Purification of Glucoamylase from Culture Broth.

Culture broth from fermentation of *A. niger* MBin118 harboring the glucoamylase gene was filtrated through a 0.22 μm PES filter, and applied on a alpha-cyclodextrin affinity gel column previously equilibrated in 50 mM NaOAc, 150 mM NaCl, pH 4.5 buffer. Unbound material was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase sample was then dialyzed against 20 mM NaOAc, pH 5.0. The purity was finally checked by SDS-PAGE, and only a single band was found.

Example 8

Construction and Expression of a Site-Directed Variant of *Penicillium oxalicum* Glucoamylase (PE001)

Two PCR reactions were performed with plasmid XYZ1471-4, described in Example 9, using primers K79V F and K79VR shown below, which were designed to substitute lysine K at position 79 from the mature sequence to varin V and primers F-NP003940 and R-NP003940 shown below, which were designed based on the known sequence and added tags for direct cloning by IN-FUSION™ strategy.

```
Primer K79V F 18mer
                                        (SEQ ID NO: 22)
GCAGTCTTTCCAATTGAC Primer K79V R 18mer
                                        (SEQ ID NO: 23)
AATTGGAAAGACTGCCCG Primer F-NP003940:
                                        (SEQ ID NO: 24)
5' ACACAACTGGGGATCCACCATGCGTCTCACTCTATTATC Primer R-NP003940:
                                        (SEQ ID NO: 25)
5' AGATCTCGAGAAGCTTAAAACTGCCACACGTCGTTGG
```

The PCR was performed using a PTC-200 DNA Engine under the conditions described below.

| PCR reaction system: | | Conditions: |
|---|---|---|
| 48.5 micro L H2O | 1 | 94° C. 2 min |
| 2 beads puRe Taq Ready-To-Go PCR | 2 | 94° C. 30 sec |
| Beads (Amersham bioscineces) | 3 | 55° C. 30 sec |
| 0.5 micro L × 2 100 pmole/micro L | 4 | 72° C. 90 sec |
| Primers | 2-4 | 25 cycles |
| (K79V F + Primer R-NP003940, K79V R + Primer F-NP003940) | 5 | 72° C. 10 min |
| 0.5 micro L Template DNA | | |

DNA fragments were recovered from agarose gel by the Qiagen gel extraction Kit according to the manufacturer's instruction. The resulting purified two fragments were cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

The ligation mixture was used to transform *E. coli* DH5α cells (TOYOBO). Selected colonies were inoculated in 3 ml of LB medium supplemented with 50 μg of ampicillin per ml and incubated at 37° C. at 225 rpm overnight. Plasmid DNA from the selected colonies was purified using Qiagen plasmid mini kit (Qiagen) according to the manufacturer's instructions. The sequence of *Penicillium oxalicum* glucoamylase site-directed variant gene sequence was verified before heterologous expression and one of the plasmids was selected for further expression, and was named pPoPE001.

Protoplasts of *Aspergillus niger* MBin118 were prepared as described in WO 95/02043. One hundred microliters of protoplast suspension were mixed with 2.5 μg of the pPoPE001 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 1% agarose L (Nippon Gene) in COVE sucrose (Cove, 1996, Biochim. Biophys. Acta 133:51-56) supplemented with 10 mM acetamide and 15 mM CsCl and added as a top layer on COVE sucrose plates supplemented with 10 mM acetamide and 15 mM CsCl for transformants selection (4 ml topagar per plate). After incubation for 5 days at 37° C. spores of sixteen transformants were picked up and seed on 750 µl YP-2% Maltose medium in 96 deepwell MT plates. After 5 days of stationary cultivation at 30° C., 10 µl of the culture-broth from each well was analyzed on a SDS-PAGE gel in order to identify the best transformants based on the ability to produce large amount of the glucoamylase.

Example 9

Purification of Site-Directed Po AMG Variant PE001

The selected transformant of the variant and the strain expressing the wild type Penicillium oxalicum glucoamylase described in Example 8 was cultivated in 100 ml of YP-2% maltose medium and the culture was filtrated through a 0.22 µm PES filter, and applied on a alpha-cyclodextrin affinity gel column previously equilibrated in 50 mM NaOAc, 150 mM NaCl, pH 4.5 buffer. Unbound materials was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase samples were then dialyzed against 20 mM NaOAc, pH 5.0.

Example 10

Characterization of PE001 Protease Stability

40 µl enzyme solutions (1 mg/ml) in 50 mM sodium acetate buffer, pH 4.5, was mixed with ⅒ volume of 1 mg/ml protease solutions such as aspergillopepsinI described in *Biochem J* 1975 April; 147(1): 45-53 or the commercially available product from Sigma and aorsin described in Biochemical journal [0264-6021] Ichishima, 2003, 371(2): 541 and incubated at 4 or 32° C. overnight. As a control experiment, H$_2$O was added to the sample instead of proteases. The samples were loaded on SDS-PAGE to see if the glucoamylases are cleaved by proteases.

In SDS-PAGE, PE001 only showed one band corresponding to the intact molecule, while the wild type glucoamylase was degraded by proteases and showed a band at lower molecular size at 60 kCa.

Example 11

Less Cleavage During Cultivation

*Aspergillus* transformant of the variant (PE001) and the wild type *Penicillium oxalicum* glucoamylase were cultivated in 6-well MT plates containing 4× diluted YP-2% maltose medium supplemented with 10 mM sodium acetate buffer, pH4.5, at 32° C. for 1 week.

The culture supernatants were loaded on SDS-PAGE.

TABLE 13

The result of SDS-PAGE of the culture supernatants

|  | Wild type glucoamylase | PE001 |
|---|---|---|
| intact glucoamylase(ca. 70 kDa) | 90% | 100% |
| cleaved glucoamylase (ca. 60 kDa) | 10% | N.D. |

N.D.: not detected.

The wild type glucoamylase was cleaved by host proteasaes during fermentation, while the variant yielded only intact molecule.

Example 12

Glucoamylase Activity of Variant PE001 Compared to Parent

The glucoamylase activity measures as AGU as described above was checked for the purified enzymes of the wild type *Penicillium oxalicum* and the variant glucoamylase.

The Glucoamylase Unit (AGU) was defined as the amount of enzyme, which hydrolyzes 1 micromole maltose per minute under the standard conditions (37° C., pH 4.3, substrate: maltose 100 mM, buffer: acetate 0.1 M, reaction time 6 minutes).

TABLE 14

| Relative specific activity | AGU/mg |
|---|---|
| *Penicillium oxalicum* wt | 100% |
| *Penicillium oxalicum* PE001 | 102% |

Example 13

Purification of Glucoamylase Variants Having Increased Thermostability

The variants showing increased thermostability may be constructed and expressed similar to the procedure described

TABLE 12

The result of SDS-PAGE after protease treatment

|  | Wild type glucoamylase | | | | PE001 | | | | |
|---|---|---|---|---|---|---|---|---|---|
| Protease | aspergillopepsin I | | aorsin | | aspergillopepsin I | | aorsin | | control |
| Incubation temperature (° C.) | 4 | 32 | 4 | 32 | 4 | 32 | 4 | 32 | 4 |
| intact glucoamylase (ca. 70 kDa) | 100% | 90% | 40% | 10% | 100% | 100% | 100% | 100% | 100% |
| cleaved glucoamylase (ca. 60 kDa) | N.D. | 10% | 60% | 90% | N.D. | N.D. | N.D. | N.D. | N.D. |

N.D.: not detected.

in Example 8. All variants were derived from the PE001. After expression in YPM medium, variants comprising the T65A or Q327F (SEQ ID NO: 14 numbering) substitution was micro-purified as follows:

Mycelium was removed by filtration through a 0.22 μm filter. 50 μl column material (alpha-cyclodextrin coupled to Mini-Leak divinylsulfone-activated agarose medium according to manufacturers recommendations) was added to the wells of a filter plate (Whatman, Unifilter 800 μl, 25-30 μm MBPP). The column material was equilibrated with binding buffer (200 mM sodium acetate pH 4.5) by two times addition of 200 μl buffer, vigorous shaking for 10 min (Heidolph, Titramax 101, 1000 rpm) and removal of buffer by vacuum (Whatman, UniVac 3). Subsequently, 400 μl culture supernatant and 100 μl binding buffer was added and the plate incubated 30 min with vigorous shaking. Unbound material was removed by vacuum and the binding step was repeated. Normally 4 wells were used per variant. Three washing steps were then performed with 200 μl buffer of decreasing ionic strength added (50/10/5 mM sodium acetate, pH 4.5), shaking for 15 min and removal of buffer by vacuum. Elution of the bound AMG was achieved by two times addition of 100 μl elution buffer (250 mM sodium acetate, 0.1% alpha-cyclodextrin, pH 6.0), shaking for 15 min and collection of eluted material in a microtiter plate by vacuum. Pooled eluates were concentrated and buffer changed to 50 mM sodium acetate pH 4.5 using centrifugal filter units with 10 kDa cut-off (Millipore Microcon Ultracel YM-10). Micropurified samples were stored at −18° C. until testing of thermostability.

Example 14

Protein Thermal Unfolding Analysis (TSA, Thermal Shift Assay)

Protein thermal unfolding of the T65A and Q327F variants, was monitored using Sypro Orange (In-vitrogen, S-6650) and was performed using a real-time PCR instrument (Applied Biosystems; Step-One-Plus).

In a 96-well plate, 25 microliter micropurified sample in 50 mM Acetate pH4.5 at approx. 100 microgram/ml was mixed (5:1) with Sypro Orange (resulting conc.=5×; stock solution from supplier=5000×). The plate was sealed with an optical PCR seal. The PCR instrument was set at a scan-rate of 76° C. pr. hr, starting at 25° C. and finishing at 96° C.

Protein thermal unfolding of the E501V+Y504T variant, was monitored using Sypro Orange (In-vitrogen, S-6650) and was performed using a real-time PCR instrument (Applied Biosystems; Step-One-Plus).

In a 96-well plate, 15 microliter purified sample in 50 mM Acetate pH4.5 at approx. 50 microgram/ml was mixed (1:1) with Sypro Orange (resulting conc.=5×; stock solution from supplier=5000×) with or without 200 ppm Acarbose (Sigma A8980). The plate was sealed with an optical PCR seal. The PCR instrument was set at a scan-rate of 76 degrees C. pr. hr, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dK) (ref: Gregory et al., 2009, *J. Biomol. Screen.* 14: 700).

TABLE 15a

| Sample | Tm (Deg. Celsius) +/−0.4 |
|---|---|
| PO-AMG (PE001) | 80.3 |
| Variant Q327F | 82.3 |
| Variant T65A | 81.9 |

TABLE 15b

| | Tm (Deg. Celsius) +/−0.4 | |
|---|---|---|
| Sample Acarbose: | − | + |
| PO-AMG (PE001) | 79.5 | 86.9 |
| Variant E501V Y504T | 79.5 | 95.2 |

Example 15

Thermostability Analysis by Differential Scanning Calorimitry (DSC)

Additional site specific variants having substitutions and/or deletions at specific positions were constructed basically as described in Example 8 and purified as described in Example 9.

The thermostability of the purified Po-AMG PE001 derived variants were determined at pH 4.0 or 4.8 (50 mM Sodium Acetate) by Differential Scanning calorimetry (DSC) using a VP-Capillary Differential Scanning calorimeter (MicroCal Inc., Piscataway, N.J., USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.0 or 4.8) at a constant programmed heating rate of 200 K/hr.

Sample- and reference-solutions (approximately 0.3 ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

The isolated variants and the DSC data are disclosed in Table 16 below.

TABLE 16

| Po-AMG name | Mutations Mutations relative to PE001 | DSC Td (° C.) @ pH 4.0 | DSC Td (° C.) @ pH 4.8 |
|---|---|---|---|
| PE001 | | 82.1 | 83.4 |
| GA167 | E501V Y504T | 82.1 | |
| GA481 | T65A K161S | 84.1 | 86.0 |
| GA487 | T65A Q405T | 83.2 | |
| GA490 | T65A Q327W | 87.3 | |
| GA491 | T65A Q327F | 87.7 | |
| GA492 | T65A Q327Y | 87.3 | |
| GA493 | P11F T65A Q327F | 87.8 | 88.5 |
| GA497 | R1K D3W K5Q G7V N8S T10K P11S | 87.8 | 88.0 |

TABLE 16-continued

| Po-AMG name | Mutations Mutations relative to PE001 | DSC Td (° C.) @ pH 4.0 | DSC Td (° C.) @ pH 4.8 |
|---|---|---|---|
| | T65A Q327F | | |
| GA498 | P2N P4S P11F T65A Q327F | 88.3 | 88.4 |
| GA003 | P11F D26C K33C T65A Q327F | 83.3 | 84.0 |
| GA009 | P2N P4S P11F T65A Q327W E501V Y504T | 88.8 | |
| GA002 | R1E D3N P4G G6R G7A N8A T10D P11D T65A Q327F | 87.5 | 88.2 |
| GA005 | P11F T65A Q327W | 87.4 | 88.0 |
| GA008 | P2N P4S P11F T65A Q327F E501V Y504T | 89.4 | 90.2 |
| GA010 | P11F T65A Q327W E501V Y504T | | 89.7 |
| GA507 | T65A Q327F E501V Y504T | | 89.3 |
| GA513 | T65A S105P Q327W | | 87.0 |
| GA514 | T65A S105P Q327F | | 87.4 |
| GA515 | T65A Q327W S364P | | 87.8 |
| GA516 | T65A Q327F S364P | | 88.0 |
| GA517 | T65A S103N Q327F | | 88.9 |
| GA022 | P2N P4S P11F K34Y T65A Q327F | | 89.7 |
| GA023 | P2N P4S P11F T65A Q327F D445N V447S | | 89.9 |
| GA032 | P2N P4S P11F T65A I172V Q327F | | 88.7 |
| GA049 | P2N P4S P11F T65A Q327F N502* | | 88.4 |
| GA055 | P2N P4S P11F T65A Q327F N502T P563S K571E | | 88.0 |
| GA057 | P2N P4S P11F R31S K33V T65A Q327F N564D K571S | | 89.5 |
| GA058 | P2N P4S P11F T65A Q327F S377T | | 88.6 |
| GA064 | P2N P4S P11F T65A V325T Q327W | | 88.0 |
| GA068 | P2N P4S P11F T65A Q327F D445N V447S E501V Y504T | | 90.2 |
| GA069 | P2N P4S P11F T65A I172V Q327F E501V Y504T | | 90.2 |
| GA073 | P2N P4S P11F T65A Q327F S377T E501V Y504T | | 90.1 |
| GA074 | P2N P4S P11F D26N K34Y T65A Q327F | | 89.1 |
| GA076 | P2N P4S P11F T65A Q327F I375A E501V Y504T | | 90.2 |
| GA079 | P2N P4S P11F T65A K218A K221D Q327F E501V Y504T | | 90.9 |
| GA085 | P2N P4S P11F T65A S103N Q327F E501V Y504T | | 91.3 |
| GA086 | P2N P4S T10D T65A Q327F E501V Y504T | | 90.4 |
| GA088 | P2N P4S F12Y T65A Q327F E501V Y504T | | 90.4 |
| GA097 | K5A P11F T65A Q327F E501V Y504T | | 90.0 |
| GA101 | P2N P4S P11F T10E E18N T65A Q327F E501V Y504T | | 89.9 |
| GA102 | P2N T10E E18N T65A Q327F E501V Y504T | | 89.8 |
| GA084 | P2N P4S P11F T65A Q327F E501V Y504T T568N | | 90.5 |
| GA108 | P2N P4S P11F T65A Q327F E501V Y504T K524T G526A | | 88.6 |
| GA126 | P2N P4S P11F K34Y T65A Q327F D445N V447S E501V Y504T | | 91.8 |
| GA129 | P2N P4S P11F R31S K33V T65A Q327F D445N V447S E501V Y504T | | 91.7 |
| GA087 | P2N P4S P11F D26N K34Y T65A Q327F E501V Y504T | | 89.8 |
| GA091 | P2N P4S P11F T65A F80* Q327F E501V Y504T | | 89.9 |
| GA100 | P2N P4S P11F T65A K112S Q327F E501V Y504T | | 89.8 |
| GA107 | P2N P4S P11F T65A Q327F E501V Y504T T516P K524T G526A | | 90.3 |
| GA110 | P2N P4S P11F T65A Q327F E501V N502T Y504* | | 90.6 |

Example 16

Thermostability Analysis by Thermo-Stress Test and pNPG Assay

Starting from one of the identified substitution variants from Example 10, identified as PE008, additional variants were tested by a thermo-stress assay in which the supernatant from growth cultures were assayed for glucoamylase (AMG) activity after a heat shock at 83° C. for 5 min.

After the heat-shock the residual activity of the variant was measured as well as in a non-stressed sample.

Description of Po-AMG pNPG Activity Assay:

The *Penicillium oxalicum* glucoamylase pNPG activity assay is a spectrometric endpoint assay where the samples are split in two and measured thermo-stressed and non-thermo-stressed. The data output is therefore a measurement of residual activity in the stressed samples.

Growth:

A sterile micro titer plate (MTP) was added 200 microliters rich growth media (FT X-14 without Dowfax) to each well. The strains of interest were inoculated in triplicates directly from frozen stocks to the MTP. Benchmark was inoculated in 20 wells. Non-inoculated wells with media were used as assay blanks. The MTP was placed in a plastic box containing wet tissue to prevent evaporation from the wells during incubation. The plastic box was placed at 34° C. for 4 days.

Assay:

50 microliters supernatant was transferred to 50 microliters 0.5 M NaAc pH 4.8 to obtain correct sample pH.

50 microliters dilution was transferred to a PCR plate and thermo-stressed at 83° C. for 5 minutes in a PCR machine. The remaining half of the dilution was kept at RT.

20 microliters of both stressed and unstressed samples was transferred to a standard MTP. 20 microliters pNPG-substrate was added to start the reaction. The plate was incubated at RT for 1 h.

The reaction was stopped and the colour developed by adding 50 microliters 0.5 M $Na_2CO_3$. The yellow colour was measured on a plate reader (Molecular Devices) at 405 nm.

Buffers:
0.5 M NaAc pH 4.8
0.25 M NaAc pH 4.8
Substrate, 6 mM pNPG:
15 mg 4-nitrophenyl D-glucopyranoside in 10 mL 0.25 NaAc pH 4.8
Stop/developing solution:
0.5 M $Na_2CO_3$ Data Treatment:

In Excel the raw Abs405 data from both stressed and unstressed samples were blank subtracted with their respective blanks. The residual activity (% res. act.=($Abs_{unstressed}$−($Abs_{unstressed}$−$Abs_{stressed}$))/$Abs_{unstressed}$*100%) was calculated and plotted relative to benchmark, Po-amg0008.

TABLE 17

| Po-AMG name | Mutations | % residual activity |
| --- | --- | --- |
| GA008 | P2N P4S P11F T65A Q327F E501V Y504T | 100 |
| GA085 | P2N P4S P11F T65A S103N Q327F E501V Y504T | 127 |
| GA097 | K5A P11F T65A Q327F E501V Y504T | 106 |
| GA107 | P2N P4S P11F T65A Q327F E501V Y504T T516P K524T G526A | 109 |

TABLE 17-continued

| Po-AMG name | Mutations | % residual activity |
| --- | --- | --- |
| GA130 | P2N P4S P11F T65A V79A Q327F E501V Y504T | 111 |
| GA131 | P2N P4S P11F T65A V79G Q327F E501V Y504T | 112 |
| GA132 | P2N P4S P11F T65A V79I Q327F E501V Y504T | 101 |
| GA133 | P2N P4S P11F T65A V79L Q327F E501V Y504T | 102 |
| GA134 | P2N P4S P11F T65A V79S Q327F E501V Y504T | 104 |
| GA150 | P2N P4S P11F T65A L72V Q327F E501V Y504T | 101 |
| GA155 | S255N Q327F E501V Y504T | 105 |

TABLE 18

| Po-AMG name | Mutations | % residual activity |
| --- | --- | --- |
| GA008 | P2N P4S P11F T65A Q327F E501V Y504T | 100 |
| GA179 | P2N P4S P11F T65A E74N V79K Q327F E501V Y504T | 108 |
| GA180 | P2N P4S P11F T65A G220N Q327F E501V Y504T | 108 |
| GA181 | P2N P4S P11F T65A Y245N Q327F E501V Y504T | 102 |
| GA184 | P2N P4S P11F T65A Q253N Q327F E501V Y504T | 110 |
| GA185 | P2N P4S P11F T65A D279N Q327F E501V Y504T | 108 |
| GA186 | P2N P4S P11F T65A Q327F S359N E501V Y504T | 108 |
| GA187 | P2N P4S P11F T65A Q327F D370N E501V Y504T | 102 |
| GA192 | P2N P4S P11F T65A Q327F V460S E501V Y504T | 102 |
| GA193 | P2N P4S P11F T65A Q327F V460T P468T E501V Y504T | 102 |
| GA195 | P2N P4S P11F T65A Q327F T463N E501V Y504T | 103 |
| GA196 | P2N P4S P11F T65A Q327F S465N E501V Y504T | 106 |
| GA198 | P2N P4S P11F T65A Q327F T477N E501V Y504T | 106 |

Example 17

Test for Glucoamylase Activity of Thermo-Stable Variants According to the Invention All of the above described variants disclosed in tables 16, 17, and 18 have been verified for Glucoamylase activity on culture supernatants using the pNPG assay described in Example 16.

Example 18

Determination of Thermostablity of Endo-Beta-Glucanases (EG) by Differential Scanning Calorimitry (DSC)

The thermostability of EGs were tested as described in the "Materials & Methods" section under "Determination of Td by Differential Scanning calorimetry for Endoglucanases".

| ID | Family | Donor | Melting point ° C. (DSC) |
| --- | --- | --- | --- |
| Endoglucanase TL (SEQ ID NO: 3) | GH5 | *Talaromyces leycettanus* | 89 |
| Endoglucanase PC (SEQ ID NO: 4) | GH5 | *Penicillium capsulatum* | 83 |

-continued

| ID | Family | Donor | Melting point ° C. (DSC) |
|---|---|---|---|
| Endoglucanase TS (SEQ ID NO: 5) | GH5 | *Trichophaea saccata* | 81 |
| Endoglucanase SF (SEQ ID NO: 7) | GH45 | *Sordaria fimicola* | 75 |

Example 19

Adding Thermostable Endo-Beta-Glucanase (EG) in Liquefaction of Corn

All treatments were evaluated via 25 g small-scale liquefaction. Corn flour and thin stillage obtained from industrial corn ethanol plants was used for the experiments. The dry solids (DS) of the corn flour was 85.62% and the DS of the thin stillage was 8.08%, both as determined by Mettler-Toledo HB43 halogen moisture balance. For liquefaction, 7.9 g corn flour, 7.5 g thin stillage, and 9.6 g tap water were added to reach DS of 29.5% and mass of 25 g in a Nalgene 30 mL polycarbonate tube with a threaded cap and rubber seal. The pH of the corn slurry was found to be about 5.1 without adjustment. The tubes containing the corn slurry were then placed in a Boekel hybridization oven with rotating rack set at 60±1° C. to heat prior to enzyme addition; rotation was set to 20 rpm. The alpha-amylase (AA) used was BE369. In addition to the AA-only control, five thermostable EGs were evaluated as shown in Table 19. After preheating for 20-30 minutes, the tubes were removed and dosed with the appropriate amount of diluted enzyme as shown in Table 20 below. Each liquefaction treatment was tested in duplicate. Actual enzyme dosages assumed a constant volume of mash in each tube; final DS of the corn slurry after all additions and prior to liquefaction was 28.2%. After enzyme addition, the tubes were shaken thoroughly and then returned to the Boekel hybridization oven heated to 75±1° C. for two hours and ten minutes; rack rotation was set at 20 rpm. Desired time at 75°±1° C. was two hours, the additional ten minutes were to allow for temperature equilibration of the corn slurry.

TABLE 19

List of EG Source, family and Sequence ID

| Source of EG | Family | Sequence ID |
|---|---|---|
| *Sordaria fimicola* | GH45 | (SEQ ID NO: 7) |
| *Thielavia terrestris* | GH45 | (SEQ ID NO: 6) |
| *Talaromyces leycettanus* | GH5 | (SEQ ID NO: 3) |
| *Penicillium capsulatum* | GH5 | (SEQ ID NO: 4) |
| *Trichophaea saccata* | GH5 | (SEQ ID NO: 5) |

TABLE 20

Enzyme Dosage in Liquefaction

| Liquefaction Treatments | AA dose (KNU-A/g DS) | EG dose (μg EP (Enzyme Protein)/g DS) |
|---|---|---|
| AA | 0.12 | |
| AA + EG | 0.12 | 100 |

After two hours liquefaction, the tubes were removed from the oven and submerged in cool water and shaken periodically for about 15 minutes until the tubes were cool to the touch. Urea and penicillin solutions prepared in-house were added to each tube to reach final concentrations of 1000 ppm and 3 ppm, respectively. For fermentation, 15 mL polypropylene tubes were prepared by drilling a 1/32 inch (1.5 mm) hole in the cap and were then weighed to record the empty weight. Approximately 5 g of slurry from each Nalgene tube (liquefaction) was transferred into each of four 15 mL tubes. The tubes were then reweighed to determine the exact weight of corn mash in each tube. Each tube was dosed with the appropriate amount of diluted Glucoamylase AC. Actual enzyme dosage was 0.6 AGU/g DS based on the exact weight of corn slurry in each tube. All tubes were dosed with 100 μL of yeast propagate and were then placed in a 32° C. water bath for Simultaneous Saccharification and Fermentation (SSF). Final calculated DS was 27.8% at the start of SSF.

Samples were collected for HPLC analysis after 53 hours of fermentation. HPLC sample preparation consisted of stopping the enzyme and yeast reactions by adding 50 μL of 40% $H_2SO_4$, vortexing to distribute the acid, centrifuging at 3000 rpm for 10 minutes, and passing the supernatant through a 0.45 μm filter. Samples were stored at 4° C. until analysis. The system used to determine ethanol and oligosaccharides concentration was an Agilent™ 100 HPLC system coupled with an RI detector. The separation column was a BioRad™ Aminex HPX-87H ion exclusion column (300 mm×7.8 mm).

Results

The results from HPLC analysis are summarized in Table 21 below. Five EGs showed higher final ethanol yield after SSF than corn mash liquefied with BE369 AA alone (Control) when added in liquefaction at 75° C. for 2 hours. A GH5 from *Talaromyces leycettanus* increased final ethanol yield by 1.93% compared to BE369 AA-only control. This EG has Td of 89° C.

TABLE 21

Summarized Ethanol Yield and Percent Change Results

| Liquefaction Treatment | Ethanol (% w/v) | Ethanol Increase |
|---|---|---|
| AA369 (Control) | 10.13 | — |
| AA369 + *S. fimicola* EG V | 10.27 | 1.31% |
| AA369 + *T. terrestris* EG V | 10.25 | 1.16% |
| AA369 + *T. leycettanus* EG II | 10.33 | 1.93% |
| AA369 + *P. capsulatum* EG II | 10.26 | 1.21% |
| AA369 + *T. saccata* EG II | 10.25 | 1.19% |

Example 20

Adding Thermostable Endo-Beta-Glucanase (EG) in Liquefaction of Corn

All treatments were evaluated via 100 or 107 g liquefaction. Two different corn flours, referred to as Corn Flour A and Corn Flour B, were obtained from industrial corn ethanol plants to be used for the experiments; each flour was evaluated in a separate experiment. The dry solids (% DS) of Corn Flour A was 86.1% and Corn Flour B was 86.3% as determined by Mettler-Toledo HB43 halogen moisture balance in duplicate.

For liquefaction of Corn Flour A, 37.2 g corn flour and 62.8 g tap water were added to reach DS of 32% and mass of 100 g in a 200 ml stainless steel Lab-O-Mat canister. The pH of the corn slurry was found to be about 6.0; 80 μl of 40% $H_2SO_4$ was added to reduce the pH to 5.0 for liquefaction. The alpha-amylase (AA) used was BE369. In addition to the AA-only control, three thermostable EGs were evaluated as shown in Table 22. Each canister was dosed with the appropriate amount of diluted enzyme as shown in Table 23 below. Each liquefaction treatment was tested in duplicate. Actual enzyme dosages assumed a constant volume of mash in each canister; final volume of the corn slurry after all additions and prior to liquefaction was 107 g and final DS was 29.9%. After enzyme addition, the canisters were sealed tightly, shaken thoroughly, and then placed in the Lab-O-Mat chamber. The program used for liquefaction began with a temperature ramp of 5° C./min to reach 75° C.; 75° C. was held for two minutes. This was followed immediately by temperature ramp of 1° C./min to reach 80° C.; 80° C. was held for 110 minutes. Alternating rotation of 45 rpm clockwise for 30 seconds followed by 45 rpm counter clockwise for 30 seconds continued throughout the program.

TABLE 22

List of EG Source, family and Sequence ID

| Source of EG | Family | Sequence ID |
| --- | --- | --- |
| *Talaromyces leycettanus* | GH5 | (SEQ ID NO: 3) |
| *Trichophaea saccata* | GH5 | (SEQ ID NO: 5) |
| *Penicillium capsulatum* | GH5 | (SEQ ID NO: 4) |

TABLE 23

Enzyme Dosage in Liquefaction

| Liquefaction Treatments | AA dose (KNU-A/g DS) | EG dose (μg EP (Enzyme Protein)/g DS) |
| --- | --- | --- |
| AA | 0.12 | — |
| AA + EG | 0.12 | 100 |

After the program was complete, the canisters were removed from the Lab-O-Mat and submerged in ice for about 20 minutes until the canisters were cool to the touch. Urea and penicillin solutions prepared in-house were added to each canister to reach final concentrations of 800 ppm and 3 ppm, respectively. For fermentation, 125 mL baffled polycarbonate flasks with screw on caps made by Corning were weighed to record the empty weight. Approximately 50 g of slurry from each canister (liquefaction) was transferred into each of two 125 mL flasks. The flasks were then reweighed to determine the exact weight of corn mash in each flask. Each flask was dosed with the appropriate amount of diluted Glucoamylase AC. Actual enzyme dosage was 0.6 AGU/g DS based on the exact weight of corn slurry in each flask. All flasks were dosed with 1100 of yeast propagate based on the average mash weight in each flask and a yeast dose of 20 μl/g corn mash rounded up to the nearest 100. The flasks were then placed in an Infors humidity controlled shaking incubator for Simultaneous Saccharification and Fermentation (SSF). The temperature was 32° C., humidity was set at 80%, and shaking at 150 rpm. Final calculated DS was 28.6% at the start of SSF.

Samples were collected for HPLC analysis after 62 hours of fermentation. HPLC sample preparation consisted of stopping the enzyme and yeast reactions by adding 550 μL of 40% H2SO4 (10 μl/g corn mash), mixing to distribute the acid, transferring about 5 g to a 15 ml Falcon tube, centrifuging at 3000 rpm for 8 minutes, and passing the supernatant through a 0.45 μm filter. Samples were stored at 4° C. until analysis. The system used to determine ethanol and oligosaccharides concentration was an Agilent™ 100 HPLC system coupled with an RI detector. The separation column was a BioRad™ Aminex HPX-87H ion exclusion column (300 mm×7.8 mm).

For liquefaction of Corn Flour B, 37.7 g corn flour and 55.3 g tap water were added to reach DS of 35% and mass of 93 g in a 200 ml stainless steel Lab-O-Mat canister. The pH of the corn slurry was found to be about 6.0; 75 μl of 40% $H_2SO_4$ was added to reduce the pH to 5.0 for liquefaction. The alpha-amylase (AA) used was BE369. In addition to the AA-only control, three thermostable EGs were evaluated as shown in Table 22. Each canister was dosed with the appropriate amount of diluted enzyme as shown in Table 23; additional tap water was added to bring the final volume of each canister to 100 g. Each liquefaction treatment was tested in duplicate. Actual enzyme dosages assumed a constant volume of mash in each canister; final volume of the corn slurry after all additions and prior to liquefaction was 100 g and final DS was 32.6%. After enzyme addition, the canisters were sealed tightly, shaken thoroughly, and then placed in the Lab-O-Mat chamber. The program used for liquefaction began with a temperature ramp of 5° C./min to reach 75° C.; 75° C. was held for two minutes. This was followed immediately by temperature ramp of 1° C./min to reach 80° C.; 80° C. was held for 110 minutes. Alternating rotation of 45 rpm clockwise for 30 seconds followed by 45 rpm counter clockwise for 30 seconds continued throughout the program.

After the program was complete, the canisters were removed from the Lab-O-Mat and submerged in ice for about 20 minutes until the canisters were cool to the touch. For fermentation, 125 mL baffled polycarbonate flasks with screw on caps made by Corning were weighed to record the empty weight. Approximately 50 g of slurry from each canister (liquefaction) was transferred into each of two 125 mL flasks. The flasks were then reweighed to determine the exact weight of corn mash in each flask. Urea and penicillin solutions prepared in-house were added to each flask to reach final concentrations of 800 ppm and 3 ppm, respectively. Each flask was dosed with the appropriate amount of diluted Glucoamylase AC. Actual enzyme dosage was 0.6 AGU/g DS based on the exact weight of corn slurry in each flask. All flasks were dosed with 1000 μL of yeast propagate based on the average mash weight in each flask and a yeast dose of 20 μl/g corn mash rounded up to the nearest 100. The flasks were then placed in an Infors humidity controlled shaking incubator for Simultaneous Saccharification and Fermentation (SSF). The temperature was 32° C., humidity was set at 80%, and shaking at 150 rpm. Final calculated DS was 30.5% at the start of SSF.

Samples were collected for HPLC analysis after 63 hours of fermentation. HPLC sample preparation consisted of stopping the enzyme and yeast reactions by adding 500 μL of 40% H2SO4 (10 μl/g corn mash), mixing to distribute the acid, transferring about 5 g to a 15 ml Falcon tube, centrifuging at 3000 rpm for 8 minutes, and passing the supernatant through a 0.45 μm filter. Samples were stored at 4° C. until analysis. The system used to determine ethanol and oligosaccharides concentration was an Agilent™ 100 HPLC system coupled with an RI detector. The separation column was a BioRad™ Aminex HPX-87H ion exclusion column (300 mm×7.8 mm).

Results

The results from HPLC analysis are summarized in Table 24 below. All EGs tested in Corn Flour A and Corn Flour B showed higher final ethanol yield after SSF than corn mash liquefied with BE369 AA alone (Control) when added in liquefaction at 80° C. for 2 hours.

TABLE 24

Summarized Ethanol Yield and Percent Change Results

| | Corn Flour A | | Corn Flour B | |
|---|---|---|---|---|
| Liquefaction Treatment | Ethanol (% w/v) | Ethanol Increase | Ethanol (% w/v) | Ethanol Increase |
| AA369 (Control) | 12.42 | — | 13.39 | — |
| AA369 + *T. leycettanus* EG II | 12.49 | 0.53% | 13.46 | 0.51% |
| AAE369 + *T. saccata* EG II | 12.46 | 0.29% | 13.40 | 0.07% |
| AA369 + *P. capsulatum* EG II | 12.50 | 0.60% | 13.42 | 0.24% |

The Present Invention is Further Described in the Following Numbered Paragraphs:

1. A process for producing fermentation products from starch-containing material comprising the steps of:
    i) liquefying the starch-containing material at a temperature above the initial gelatinization temperature using:
    an alpha-amylase;
    an endoglucanase having a Melting Point (DSC) above 70° C.;
    ii) saccharifying using a carbohydrate-source generating enzyme;
    iii) fermenting using a fermenting organism.

2. The process of paragraph 1, wherein the endoglucoanase has a Melting Point (DSC) above 72° C., such as above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

3. The process of paragraphs 1 or 2, wherein the endoglucanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3 herein, preferably derived from a strain of the genus *Talaromyces*, such as a strain of *Talaromyces leycettanus*.

4. The process of paragraphs 1 or 2, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 4 herein, preferably derived from a strain of the genus *Penicillium*, such as a strain of *Penicillium capsulatum*.

5. The process of paragraphs 1 or 2, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 5 herein, preferably derived from a strain of the genus *Trichophaea*, such as a strain of *Trichophaea saccata*.

6. The process of paragraphs 1 or 2, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 6 herein, preferably derived from a strain of the genus *Thielavia*, such as a strain of *Thielavia terrestris*.

7. The process of paragraphs 1 or 2, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 7 herein, preferably derived from a strain of the genus *Sordaria*, such as a strain of *Sordaria fimicola*.

8. The process of any of paragraphs 1-7, further comprises, prior to the liquefaction step i), the steps of:
    a) reducing the particle size of the starch-containing material, preferably by dry milling;
    b) forming a slurry comprising the starch-containing material and water.

9. The process of any of paragraphs 1-8, wherein at least 50%, preferably at least 70%, more preferably at least 80%, especially at least 90% of the starch-containing material fit through a sieve with #6 screen.

10. The process of any of paragraphs 1-9, wherein the pH during liquefaction is between 4.0-6.5, such as 4.5-6.2, such as above 4.8-6.0, such as between 5.0-5.8.

11. The process of any of paragraphs 1-10, wherein the temperature during liquefaction is in the range from 70–100° C., such as between 70-95° C., such as between 75-90° C., preferably between 80-90° C., such as around 85° C.

12. The process of any of paragraphs 1-5, wherein a jet-cooking step is carried out after liquefaction in step i).

13. The process of paragraph 12, wherein the jet-cooking is carried out at a temperature between 95-160° C., such as between 110-145° C., preferably 120-140° C., such as 125-135° C., preferably around 130° C. for about 1-15 minutes, preferably for about 3-10 minutes, especially around about 5 minutes.

14. The process of any of paragraphs 1-7, wherein saccharification and fermentation is carried out sequentially or simultaneously.

15. The process of any of paragraphs 1-14, wherein saccharification is carried out at a temperature from 20-75° C., preferably from 40-70° C., such as around 60° C., and at a pH between 4 and 5.

16. The process of any of paragraphs 1-15, wherein fermentation or simultaneous saccharification and fermentation (SSF) is carried out at a temperature from 25° C. to 40° C., such as from 28° C. to 35° C., such as from 30° C. to 34° C., preferably around about 32° C., such as for 6 to 120 hours, in particular 24 to 96 hours.

17. The process of any of paragraphs 1-16, wherein the fermentation product is recovered after fermentation, such as by distillation.

18. The process of any of paragraphs 1-17, wherein the fermentation product is an alcohol, preferably ethanol, especially fuel ethanol, potable ethanol and/or industrial ethanol.

19. The process of any of paragraphs 1-18, wherein the starch-containing starting material is whole grains.

20. The process of any of paragraphs 1-19, wherein the starch-containing material is derived from corn, wheat, barley, rye, milo, sago, cassava, manioc, tapioca, sorghum, rice or potatoes.

21. The process of any of paragraphs 1-20, wherein the fermenting organism is yeast, preferably a strain of *Saccharomyces*, especially a strain of *Saccharomyces cerevisiae*.

22. The process of any of paragraphs 1-21, wherein the alpha-amylase is a bacterial or fungal alpha-amylase.

23. The process of any of paragraphs 1-22, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

24. The process of paragraph 23, wherein the *Bacillus stearothermophilus* alpha-amylase or variant thereof is truncated, preferably to have around 491 amino acids, such as from 480-495 amino acids.

25. The process of any of paragraphs 23 or 24, wherein the *Bacillus stearothermophilus* alpha-amylase has a double deletion in positions I181+G182, and optionally a N193F substitution, or deletion of R179 and G180 (using SEQ ID NO: 1 herein for numbering).

26. The process of any of paragraphs 23-25 wherein the *Bacillus stearothermophilus* alpha-amylase has a substitution in position S242, preferably S242Q substitution.

27. The process of any of paragraphs 23-26, wherein the *Bacillus stearothermophilus* alpha-amylase has a substitution in position E188, preferably E188P substitution.

28. The process of any of paragraphs 1-27, wherein the alpha-amylase has a T½ (min) at pH 4.5, 85° C., 0.12 mM CaCl$_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

29. The process of any of paragraphs 1-28, wherein the alpha-amylase is selected from the group of *Bacillus stearothermophilus* alpha-amylase variants with the following mutations in addition to I181*+G182* and optionally N193F (using SEQ ID NO: 1 for numbering):

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A + Q89R + E129V + K177L + R179E + Q254S + M284V.

30. The process of any of paragraphs 1-29, wherein the alpha-amylase is selected from the group of *Bacillus stearothermophilus* alpha-amylase variants:
 I181*+G182*+N193F+E129V+K177L+R179E;
 I181*+G182*+N193F+V59A+Q89R+E129V+K177L+R179E+H208Y+K220P+N224L+Q254S;
 I181*+G182*+N193F+V59A Q89R+E129V+K177L+R179E+Q254S+M284V; and
 I181*+G182*+N193F+E129V+K177L+R179E+K220P+N224L+S242Q+Q254S (using SEQ ID NO: 1 for numbering).

31. The process of any of paragraphs 1-30, further wherein a protease is present and/or added in liquefaction, wherein the protease has a thermostability value of more than 25% determined as Relative Activity at 80° C./70° C.

32. The process of any of paragraphs 1-31, wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

33. The process of any of paragraphs 1-26, wherein the protease has a thermostability of between 20 and 50%, such as between 20 and 40%, such as 20 and 30% determined as Relative Activity at 80° C./70° C.

34. The process of any of paragraphs 1-33, wherein the protease has a thermostability between 50 and 115%, such as between 50 and 70%, such as between 50 and 60%, such as between 100 and 120%, such as between 105 and 115% determined as Relative Activity at 80° C./70° C. or wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

35. The process of any of paragraphs 1-34, wherein the protease has thermostability of between 10 and 50%, such as between 10 and 30%, such as between 10 and 25% determined as Relative Activity at 85° C./70° C.

36. The process of any of paragraphs 1-35, wherein the protease has a themostability above 60%, such as above 90%, such as above 100%, such as above 110% at 85° C. as determined using the Zein-BCA assay.

37. The process of any of paragraphs 1-36, wherein the protease has a themostability between 60-120, such as between 70-120%, such as between 80-120%, such as between 90-120%, such as between 100-120%, such as 110-120% at 85° C. as determined using the Zein-BCA assay.

38. The process of any of paragraphs 1-37, wherein the protease is of fungal origin.

39. The process of any of paragraphs 1-38, wherein the protease is a variant of the metallo protease derived from a strain of the genus *Thermoascus*, preferably a strain of *Thermoascus aurantiacus*, especially *Thermoascus aurantiacus* CGMCC No. 0670.

40. The process of any of paragraphs 1-39, wherein the protease is a variant of the metallo protease disclosed as the mature part of SEQ ID NO. 2 disclosed in WO 2003/048353 or the mature part of SEQ ID NO: 1 in WO 2010/008841 or SEQ ID NO: 2 herein mutations selected from the group of:
S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+ D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A 112P+D142L; and
D79L+S87P+D142L.

41. The process of any of paragraphs 1-40, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 2 herein with the following mutations:
D79L+S87P+A112P+D142L:
D79L+S87P+D142L; or
A27K+D79L+Y82F+S87G+D104P+A112P+A126V+ D142L.

42. The process of any of paragraphs 1-41, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 2 herein.

43. The process of any of paragraphs 1-42, wherein the protease variant of the *Thermoascus aurantiacus* protease shown in SEQ ID NO: 2 is one of the following:
D79L S87P D142L
D79L S87P A112P D142L
D79L Y82F S87P A112P D142L
S38T D79L S87P A112P A126V D142L
D79L Y82F S87P A112P A126V D142L
A27K D79L S87P A112P A126V D142L
S49P D79L S87P A112P D142L
S50P D79L S87P A112P D142L
D79L S87P D104P A112P D142L
D79L Y82F S87G A112P D142L
570V D79L Y82F S87G Y97W A112P D142L
D79L Y82F S87G Y97W D104P A112P D142L
570V D79L Y82F S87G A112P D142L
D79L Y82F S87G D104P A112P D142L
D79L Y82F S87G A112P A126V D142L
Y82F S87G 570V D79L D104P A112P D142L
Y82F S87G D79L D104P A112P A126V D142L
A27K D79L Y82F S87G D104P A112P A126V D142L 44. The process of any of paragraphs 1-43, wherein the protease is of bacterial origin.

45. The process of any of paragraphs 1-44, wherein the protease is derived from a strain of *Pyrococcus*, preferably a strain of *Pyrococcus furiosus*.

46. The process of any of paragraphs 1-45, wherein the protease is the one shown in SEQ ID NO: 1 in U.S. Pat. No. 6,358,726 or SEQ ID NO: 13 herein.

47. The process of any of paragraphs 1-46, wherein the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726 or SEQ ID NO: 13 herein.

48. The process of any of paragraphs 1-47, further wherein a carbohydrate-source generating enzyme is present and/or added during liquefaction step i), preferably a glucoamylase.

49. The process of any of paragraphs 1-48, wherein the carbohydrate-source generating enzyme present and/or added during liquefaction step i) is a glucoamylase having a heat stability at 85° C., pH 5.3, of at least 20%, such as at least 30%, preferably at least 35%.

50. The process of any of paragraphs 48-49, wherein the carbohydrate-source generating enzyme is a glucoamylase having a relative activity pH optimum at pH 5.0 of at least 90%, preferably at least 95%, preferably at least 97%.

51. The process of any of paragraphs 48-50, wherein the carbohydrate-source generating enzyme is a glucoamylase having a pH stability at pH 5.0 of at least at least 80%, at least 85%, at least 90%.

52. The process of any of paragraphs 48-51, wherein the carbohydrate-source generating enzyme present and/or added during liquefaction step i) is a glucoamylase, preferably derived from a strain of the genus *Penicillium*, especially a strain of *Penicillium oxalicum* disclosed as SEQ ID NO: 2 in WO 2011/127802 or SEQ ID NOs: 9 or 14 herein.

53. The process of paragraphs 48-52, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 (mature) herein.

54. The process of any of paragraphs 48-53, wherein the carbohydrate-source generating enzyme is a variant of the glucoamylase derived from a strain of *Penicillium oxalicum* disclosed as SEQ ID NO: 2 in WO 2011/127802 having a K79V substitution (using the mature sequence shown in SEQ ID NO: 14 herein for numbering).

55. The process of any of paragraphs 52-54, wherein the *Penicillium oxalicum* glucoamylase has a K79V substitution (using the mature sequence shown as SEQ ID NO: 14 herein for numbering) and further one of the following:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or

P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or

P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

56. The process of any of paragraphs 48-55, further wherein a glucoamylase is present and/or added during saccharification and/or fermentation.

57. The process of any of paragraphs 1-56, wherein the glucoamylase present and/or added during saccharification and/or fermentation is of fungal origin, preferably from a stain of *Aspergillus*, preferably *Aspergillus niger, Aspergillus awamori*, or *Aspergillus oryzae*; or a strain of *Trichoderma*, preferably *T. reesei*; or a strain of *Talaromyces*, preferably *T. emersonii*, or a strain of *Pycnoporus*, or a strain of *Gloephyllum*, or a strain of the *Nigrofomes*.

58. The process of any of paragraphs 1-57, further wherein a pullulanase is present and/or added during liquefaction and/or saccharification.

59. The process of paragraph 58, wherein the pullulanase present or added during liquefaction step i) is a family GH57 pullulanase, wherein the pullulanase preferably includes an X47 domain as disclosed in WO 2011/087836.

60. The process of paragraphs 1-59, wherein a phytase is present and/or added during liquefaction and/or saccharification.

61. The process of any of paragraphs 58-60, wherein the phytase is derived from *Buttiauxella*, such as *Buttiauxella gaviniae, Buttiauxella agrestis*, or *Buttiauxella noackies*, disclosed in WO 2008/092901, or *Citrobacter braakii*, such as one disclosed in WO 2006/037328.

62. The process of any of paragraphs 1-61, comprising the steps of:
i) liquefying the starch-containing material at a pH in the range between from above 4.0-6.5 at a temperature in the range from 70–100° C. using:
an alpha-amylase derived from *Bacillus stearothermophilus*;
an endoglucanase having a Melting Point (DSC) above 70° C.;
ii) saccharifying using a glucoamylase enzyme;
iii) fermenting using a fermenting organism.

63. A process of paragraphs 1-62, comprising the steps of:
i) liquefying the starch-containing material at a pH in the range between from above 4.5-6.2 at a temperature above the initial gelatinization temperature using:
an alpha-amylase, preferably derived from *Bacillus stearothermophilus*, having a T½ (min) at pH 4.5, 85° C., 0.12 mM CaCl$_2$ of at least 10;
an endoglucanase having a Melting Point (DSC) above 70° C.;
ii) saccharifying using a glucoamylase enzyme;
iii) fermenting using a fermenting organism.

64. A process of paragraphs 1-63, comprising the steps of:
i) liquefying the starch-containing material at a pH in the range between from above 4.0-6.5 at a temperature between 70-100° C.:
a bacterial alpha-amylase, preferably derived from *Bacillus stearothermophilus*, having a T½ (min) at pH 4.5, 85° C., 0.12 mM CaCl$_2$ of at least 10;
an endoglucanase having a Melting Point (DSC), between 70° C. and 95° C.;
optionally a protease, preferably derived from *Pyrococcus furiosus* or *Thermoascus aurantiacus*, having a thermostability value of more than 20% determined as Relative Activity at 80° C./70° C.;
ii) saccharifying using a glucoamylase enzyme;
iii) fermenting using a fermenting organism.

65. A process of paragraphs 1-64, comprising the steps of:
i) liquefying the starch-containing material at a pH in the range between from above 4.0-6.5 at a temperature above the initial gelatinization temperature using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
E129V+K177L+R179E+K220P+N224L+S242Q+Q254S;
V59A Q89R+E129V+K177L+R179E+Q254S+M284V (using SEQ ID NO: 1 herein for numbering);
an endoglucanase having a Melting Point (DSC), between 70° C. and 95° C.; such as an endoglucanase having at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% to the mature part of the polypeptide of SEQ ID NOs: 3, 4, 5, 6, or 7 herein;
optionally a protease having a thermostability value of more than 20% determined as Relative Activity at 80° C./70° C. derived from *Pyrococcus furiosus* and/or *Thermoascus aurantiacus*; and optionally
optionally a *Penicillium oxalicum* glucoamylase in SEQ ID NO: 14 herein having substitutions selected from the group of:
K79V;
K79V+P11F+T65A+Q327F; or
K79V+P2N+P4S+P11F+T65A+Q327F; (using SEQ ID NO: 14 hereinfor numbering);
ii) saccharifying using a glucoamylase enzyme;
iii) fermenting using a fermenting organism.

66. A process of paragraphs 1-65, comprising the steps of:
i) liquefying the starch-containing material at a pH in the range between from above 4.0-6.5 at a temperature between 70-100° C. using:
an alpha-amylase derived from *Bacillus stearothermophilus* having a double deletion I181+G182 and optional substitution N193F; and optionally further one of the following set of substitutions:

V59A+Q89R+E129V+K177L+R179E+H208Y+K220P+N224L+Q254S; or

V59A Q89R+E129V+K177L+R179E+Q254S+M284V (using SEQ ID NO: 1 herein (using SEQ ID NO: 1 herein for numbering);

an endoglucanase having a Melting Point (DSC), between 70° C. and 95° C. having at least 90% identity to the mature part of the polypeptide of SEQ ID NO: 3 herein;

a protease having a thermostability value of more than 20% determined as Relative Activity at 80° C./70° C. derived from *Pyrococcus furiosus* and/or *Thermoascus aurantiacus*; and optionally a *Penicillium oxalicum* glucoamylase in SEQ ID NO: 14 herein having substitutions selected from the group of:

K79V; or

K79V+P11F+T65A+Q327F; or

K79V+P2N+P4S+P11F+T65A+Q327F (using SEQ ID NO: 14 for numbering);

ii) saccharifying using a glucoamylase enzyme;

iii) fermenting using a fermenting organism.

67. A process of paragraphs 1-65, comprising the steps of:

i) liquefying the starch-containing material at a pH in the range between from above 4.0-6.5 at a temperature between 70-100° C. using:

an alpha-amylase derived from *Bacillus stearothermophilus* having a double deletion I181+G182 and optional substitution N193F; and optionally further one of the following set of substitutions:

E129V+K177L+R179E;

V59A+Q89R+E129V+K177L+R179E+H208Y+K220P+N224L+Q254S;

V59A Q89R+E129V+K177L+R179E+Q254S+M284V;

E129V+K177L+R179E+K220P+N224L+S242Q+Q254S (using SEQ ID NO: 1 herein for numbering).

a protease having a thermostability value of more than 20% determined as Relative Activity at 80° C./70° C. derived from *Pyrococcus furiosus* a *Penicillium oxalicum* glucoamylase in SEQ ID NO: 14 herein having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

ii) saccharifying using a glucoamylase enzyme;

iii) fermenting using a fermenting organism.

68. The process of any of paragraphs 62-67, wherein the *Bacillus stearothermophilus* alpha-amylase (SEQ ID NO: 1 herein) is the mature alpha-amylase or corresponding mature alpha-amylases having at least 60, such as at least 70%, such as at least 80% identity, such as at least 90% identity, at least 95% identity at least 96% identity at least 97% identity at least 99% identity to the SEQ ID NO: 1.

69. The process of any of paragraphs 64-68, wherein the *Pyrococcus furiosus* protease (SEQ ID NO: 13) or *Thermoascus aurantiacus* protease (SEQ ID NO: 3) is the mature protease or corresponding mature protease having at least 80% identity, at least 90% identity, at least 95% identity at least 96% identity at least 97% identity at least 99% identity to SEQ ID NO: 13 or SEQ ID NO: 3, respectively.

70. The process of any of paragraphs 65-69, wherein the *Penicillium oxalicum* glucoamylase (SEQ ID NO: 14 herein), or a variant thereof, is the mature glucoamylase or corresponding mature glucoamylase having at least 80% identity, at least 90% identity, at least 95% identity at least 96% identity at least 97% identity at least 99% identity to the SEQ ID NO: 14 herein.

71. The process of any of paragraphs 1-70, wherein cellulase or cellulolytic enzyme composition is present or adding during fermentation or simultaneous saccharification and fermentation.

72. The process of any of paragraphs 1-71, wherein a cellulase or cellulolytic enzyme composition and a glucoamylase are present or added during fermentation or simultaneous saccharification and fermentation.

73. The process of any of paragraphs 1-72, wherein cellulase or cellulolytic enzyme composition and glucoamylase present or added during fermentation or simultaneous saccharification and fermentation added.

74. The process of any of paragraphs 71-73 wherein the cellulase or cellulolytic enzyme composition is derived from *Trichoderma reesei, Humicola insolens, Chrysosporium lucknowense* or *Penicillium decumbens*.

75. The process of any of paragraphs 71-74, wherein the cellulase or cellulolytic enzyme composition comprising a beta-glucosidase, a cellobiohydrolase, and an endoglucanase.

76. The process of any of paragraphs 71-75, wherein the cellulase or cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 6 herein or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*.

77. The process of any of paragraphs 71-76, wherein the cellulase or cellulolytic enzyme composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 8 herein.

78. The process of any of paragraphs 71-77, wherein the cellulase or cellulolytic enzyme composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 6 in WO 2011/057140 or SEQ ID NO: 2 herein, or a strain of the genus *Trichoderma*, such as a strain of *Trichoderma reesei*.

79. The process of any of paragraphs 71-78, wherein the cellulase or cellulolytic enzyme composition comprises a cellobiohydrolase II (CBH II, such as one derived from a strain of the genus *Aspergillus*, such as a strain of *Aspergillus fumigatus; such as the one disclosed as SEQ ID NO: 4 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

80. The process of any of paragraphs 71-79, wherein the cellulase or cellulolytic enzyme composition comprises a GH61 polypeptide having cellulolytic enhancing activity and a beta-glucosidase.

81. The process of any of paragraphs 71-80, wherein the cellulase or cellulolytic enzyme composition comprises a GH61 polypeptide having cellulolytic enhancing activity and a beta-glucosidase.

82. The process of any of paragraphs 71-81, wherein the cellulase or cellulolytic enzyme composition comprises a GH61 polypeptide having cellulolytic enhancing activity, a beta-glucosidase, and a CBHI.

83. The process of any of paragraphs 71-82, wherein the cellulase or cellulolytic enzyme composition comprises a GH61 polypeptide having cellulolytic enhancing activity, a beta-glucosidase, a CBHI, and a CBHII.

84. The process of any of paragraphs 71-83, wherein the cellulase or cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

85. The process of any of paragraphs 71-84, wherein the cellulase or cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 6 herein.

86. The process of any of paragraphs 71-85, wherein the cellulase or cellulolytic enzyme composition is a *Trichoderma reesei* cellulolytic enzyme composition further comprising *Penicillium emersonii* GH61A polypeptide having cellulolytic enhancing activity disclosed in WO 2011/041397 (SEQ ID NO: 8 herein) and *Aspergillus fumigatus* beta-glucosidase (SEQ ID NO: 2 of WO 2005/047499) or SEQ ID NO: 6 herein or a variant thereof with the following substitutions: F100D, S283G, N456E, F512Y.

87. The process of any of paragraphs 71-86, wherein the cellulase or cellulolytic enzyme composition comprises one or more of the following components
  (i) an *Aspergillus fumigatus* cellobiohydrolase I;
  (ii) an *Aspergillus fumigatus* cellobiohydrolase II;
  (iii) an *Aspergillus fumigatus* beta-glucosidase or variant thereof; and
  (iv) a *Penicillium* sp. GH61 polypeptide having cellulolytic enhancing activity; or homologs thereof.

88. The process of any of paragraphs 71-87, wherein the cellulase or cellulolytic enzyme composition is SPIRIZYME ACHIEVE™, CELLIC CTEC™, CELLIC CTEC2™, CELLIC CTEC3™, ACCELLERASE 1000™, ACCELLERASE 1500™, ACCELLERASE DUET™, ACCELLERASE TRIO™.

89. The process of any of paragraphs 71-88, wherein the glucoamylase present or added during saccharification or simultaneous saccharification and fermentation is of fungal origin, preferably from a stain of *Aspergillus*, preferably *Aspergillus niger*, *Aspergillus awamori*, or *Aspergillus oryzae*; or a strain of *Trichoderma*, preferably *T. reesei*; or a strain of *Talaromyces*, preferably *T. emersonii*, or a strain of *Pycnoporus*, or a strain of *Gloephyllum*, or a strain of the *Nigrofomes*.

90. The process of any of paragraphs 72-89, wherein the glucoamylase is a blend of glucoamylase derived from *Talaromyces emersonii* disclosed in WO 99/28448 or SEQ ID NO: 28 herein, *Trametes cingulata* glucoamylase disclosed as SEQ ID NO: 2 in WO 06/69289 or SEQ ID NO: 26 herein, and *Rhizomucor pusillus* alpha-amylase with *Aspergillus niger* glucoamylase linker and SBD disclosed as V039 in Table 5 in WO 2006/069290 or SEQ ID NO: 27 herein.

91. The process of any of paragraphs 72-90, wherein the alpha-amylase is the *Rhizomucor pusillus* alpha-amylase having an *Aspergillus niger* glucoamylase linker and starch-binding domain (SBD) (SEQ ID NO: 11 herein) which further comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 11 herein for numbering).

92. A composition comprising:
  i) an alpha-amylase;
  ii) an endoglucanase having a Melting Point (DSC) above 70° C.;
  iii) optionally a protease;
  iv) optionally a carbohydrate-source generating enzyme.

93. The composition of paragraph 92, wherein the alpha-amylase is a bacterial or fungal alpha-amylase.

94. The composition of any of paragraphs 92-93, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

95. The composition of paragraph 94, wherein the *Bacillus stearothermophilus* alpha-amylase or variant thereof is truncated, preferably to have around 491 amino acids, such as from 480-495 amino acids.

96. The composition of any of paragraphs 92-95, wherein the *Bacillus stearothermophilus* alpha-amylase has a double deletion in positions I181+G182 and optionally a N193F substitution, or deletion of R179 and G180 (using SEQ ID NO: 1 herein for numbering).

97. The composition of any of paragraphs 92-96 wherein the *Bacillus stearothermophilus* alpha-amylase has a substitution in position S242, preferably S242Q substitution.

98. The composition of any of paragraphs 92-97, wherein the *Bacillus stearothermophilus* alpha-amylase has a substitution in position E188, preferably E188P substitution.

99. The composition of any of paragraphs 92-98, wherein the alpha-amylase has a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

100. The composition of any of paragraphs 92-99, wherein the alpha-amylase is selected from the group of *Bacillus stearomthermphilus* alpha-amylase variants:

I181*+G182*+N193F+E129V+K177L+R179E;

181*+G182*+N193F+V59A+Q89R+E129V+K177L+R179E+H208Y+K220P+N224L+Q254S;

I181*+G182*+N193F+V59A Q89R+E129V+K177L+R179E+Q254S+M284V; and

I181*+G182*+N193F+E129V+K177L+R179E+K220P+N224L+S242Q+Q254S (using SEQ ID NO: 1 herein for numbering).

101. The composition of any of paragraphs 92-100, wherein the endoglucoanase has a Melting Point (DSC) above 72° C., such as above 74° C., such as above 76° C., such as above 78° C., such as above 80° C., such as above 82° C., such as above 84° C., such as above 86° C., such as above 88° C.

102. The composition paragraphs any of paragraphs 92-101, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 3 herein, preferably derived from a strain of the genus *Talaromyces*, such as a strain of *Talaromyces leycettanus*.

103. The composition of any of paragraphs 92-102, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 4 herein, preferably derived from a strain of the genus *Penicillium*, such as a strain of *Penicillium capsulatum*.

104. The composition of any of paragraphs 92-103, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 5 herein, preferably derived from a strain of the genus *Trichophaea*, such as a strain of *Trichophaea saccata*.

105. The composition of any of paragraphs 92-104, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 6 herein, preferably derived from a strain of the genus *Thielavia*, such as a strain of *Thielavia terrestris*.

106. The composition of any of paragraphs 92-105, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% identity to the mature part of the polypeptide of SEQ ID NO: 7, preferably derived from a strain of the genus *Sordaria*, such as a strain of *Sordaria fimicola*.

107. The composition of any of paragraphs 92-106, wherein the protease with a thermostability value of more than 20%, such as more than 25% determined as Relative Activity at 80° C./70° C.

108. The composition of any of paragraphs 92-107, wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

109. The composition of any of paragraphs 92-108, wherein the protease has a thermostability of between 20 and 50%, such as between 20 and 40%, such as 20 and 30% determined as Relative Activity at 80° C./70° C.

110. The composition of any of paragraphs 92-109, wherein the protease has a thermostability between 50 and 115%, such as between 50 and 70%, such as between 50 and 60%, such as between 100 and 120%, such as between 105 and 115% determined as Relative Activity at 80° C./70° C.

111. The composition of any of paragraphs 92-110, wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

112. The composition of any of paragraphs 92-111, wherein the protease has thermostability of between 10 and 50%, such as between 10 and 30%, such as between 10 and 25% determined as Relative Activity at 85° C./70° C.

113. The composition of any of paragraphs 92-112, wherein the protease has a thermostability above 60%, such as above 90%, such as above 100%, such as above 110% at 85° C. as determined using the Zein-BCA assay.

114. The composition of any of paragraphs 92-113, wherein the protease has a thermostability between 60-120, such as between 70-120%, such as between 80-120%, such as between 90-120%, such as between 100-120%, such as 110-120% at 85° C. as determined using the Zein-BCA assay.

115. The composition of any of paragraphs 92-114, wherein the protease is of fungal origin.

116. The composition of any of paragraphs 92-115, wherein the protease is a variant of the metallo protease derived from a strain of the genus *Thermoascus*, preferably a strain of *Thermoascus aurantiacus*, especially *Thermoascus aurantiacus* CGMCC No. 0670.

117. The composition of any of paragraphs 92-116, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 2 herein with the following mutations:

D79L+S87P+A112P+D142L:

D79L+S87P+D142L; or

A27K+D79L+Y82F+S87G+D104P+A112P+A126V+D142L.

118. The composition of any of paragraphs 92-118, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 2 herein.

119. The composition of any of paragraphs 92-118, wherein the protease variant of the *Thermoascus aurantiacus* protease shown in SEQ ID NO: 2 herein is one of the following:

D79L S87P D142L
D79L S87P A112P D142L
D79L Y82F S87P A112P D142L
S38T D79L S87P A112P A126V D142L
D79L Y82F S87P A112P A126V D142L
A27K D79L S87P A112P A126V D142L
S49P D79L S87P A112P D142L
S50P D79L S87P A112P D142L
D79L S87P D104P A112P D142L
D79L Y82F S87G A112P D142L
570V D79L Y82F S87G Y97W A112P D142L
D79L Y82F S87G Y97W D104P A112P D142L
570V D79L Y82F S87G A112P D142L
D79L Y82F S87G D104P A112P D142L
D79L Y82F S87G A112P A126V D142L
Y82F S87G S70V D79L D104P A112P D142L
Y82F S87G D79L D104P A112P A126V D142L
A27K D79L Y82F S87G D104P A112P A126V D142L.

120. The composition of any of paragraphs 92-119, wherein the protease is of bacterial origin.

121. The composition of any of paragraphs 92-120, wherein the protease is derived from a strain of *Pyrococcus*, preferably a strain of *Pyrococcus furiosus*.

122. The composition of any of paragraphs 92-121, wherein the protease is the one shown in SEQ ID NO: 1 in U.S. Pat. No. 6,358,726 or SEQ ID NO: 13 herein.

123. The composition of any of paragraphs 92-122, wherein the protease is one having at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,358,726 or SEQ ID NO: 13 herein.

124. The composition of any of paragraphs 92-123, wherein a carbohydrate-source generating enzyme is a glucoamylase.

125. The composition of any of paragraphs 92-124, wherein the carbohydrate-source generating enzyme is a glucoamylase having a heat stability at 85° C., pH 5.3, of at least 20%, such as at least 30%, preferably at least 35%.

126. The composition of any of paragraphs 92-125, wherein the carbohydrate-source generating enzyme is a glucoamylase having a relative activity pH optimum at pH 5.0 of at least 90%, preferably at least 95%, preferably at least 97%.

127. The composition of any of paragraphs 92-126, wherein the carbohydrate-source generating enzyme is a glucoamylase having a pH stability at pH 5.0 of at least at least 80%, at least 85%, at least 90%.

128. The composition of any of paragraphs 92-127, wherein the carbohydrate-source generating enzyme is a glucoamylase, preferably derived from a strain of the genus *Penicillium*, especially a strain of *Penicillium oxalicum* disclosed as SEQ ID NO: 2 in WO 2011/127802 or SEQ ID NOs: 9 or 14 herein.

129. The composition of paragraphs 92-128, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

130. The composition of any of paragraphs 92-129, wherein the carbohydrate-source generating enzyme is a variant of the glucoamylase derived from a strain of *Penicillium oxalicum* disclosed as SEQ ID NO: 2 in WO 2011/127802 having a K79V substitution (using the mature sequence shown in SEQ ID NO: 14 for numbering).

131. The composition of any of paragraphs 92-130, further comprising a glucoamylase.

132. The composition of any of paragraphs 92-131, wherein the glucoamylase present and/or added during saccharification and/or fermentation is of fungal origin, preferably from a stain of *Aspergillus*, preferably *Aspergillus niger*, *Aspergillus awamori*, or *Aspergillus oryzae*; or a strain of *Trichoderma*, preferably *T. reesei*; or a strain of *Talaromyces*, preferably *T. emersonii*, or a strain of *Pycnoporus*, or a strain of *Gloephyllum*, or a strain of the *Nigrofomes*.

133. The composition of any of paragraphs 92-132, further comprising a pullulanase.

134. The composition of paragraph 133, wherein the pullulanase is a family GH57 pullulanase, wherein the pullulanase preferably includes an X47 domain as disclosed in WO 2011/087836.

135. The composition of any of paragraphs 92-134, further comprising a phytase.

136. The composition of any of paragraph 135, wherein the phytase is derived from *Buttiauxella*, such as *Buttiauxella gaviniae*, *Buttiauxella agrestis*, or *Buttiauxella noackies* disclosed in WO 2008/092901, or *Citrobacter braakii*, such as one disclosed in WO 2006/037328.

137. The composition of any of paragraphs 92-136 comprising
an alpha-amylase derived from *Bacillus stearothermophilus*;
an endoglucanase having a Melting Point (DSC) above 70° C., such as 70° C. and 95° C.;
optionally a protease having a thermostability value of more than 20% determined as Relative Activity at 80° C./70° C. derived from *Pyrococcus furiosus* or *Thermoascus auranticus*; and
optionally a glucoamylase, such as one derived from *Penicillium oxalicum*.

138. The composition of any of paragraphs 92-137, comprising
an alpha-amylase, preferably derived from *Bacillus stearothermophilus*, having a T½ (min) at pH 4.5, 85° C., 0.12 mM CaCl$_2$ of at least 10;
an endoglucanase having a Melting Point (DSC) between 70° C. and 95° C.;
a protease, preferably derived from *Pyrococcus furiosus* or *Thermoascus aurantiacus*, having a thermostability value of more than 20% determined as Relative Activity at 80° C./70° C.; and
optionally a glucoamylase, e.g., derived from *Penicillium oxalicum*.

139. The composition of any of paragraphs 92-138, comprising
an alpha-amylase derived from *Bacillus stearothermophilus* having a double deletion I181+G182 and optionally substitution N193F; and optionally further one of the following set of substitutions:

E129V+K177L+R179E;
V59A+Q89R+E129V+K177L+R179E+H208Y+K220P+N224L+Q254S;
V59A+Q89R+E129V+K177L+R179E+Q254S+M284V; and
E129V+K177L+R179E+K220P+N224L+S242Q+Q254S (using SEQ ID NO: 1 herein for numbering);
an endoglucanase having a Melting Point (DSC) above 70° C.;
optionally a protease, preferably derived from *Pyrococcus furiosus* and/or *Thermoascus aurantiacus*, having a thermostability value of more than 20% determined as Relative Activity at 80° C./70° C.; and
optionally a *Penicillium oxalicum* glucoamylase in SEQ ID NO: 14 herein having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 herein for numbering).

140. The composition of any of paragraphs 92-139, wherein the *Bacillus stearothermophilus* alpha-amylase (SEQ ID NO: 1 herein), or a variant thereof, is the mature alpha-amylase or corresponding mature alpha-amylases having at least 80% identity, at least 90% identity, at least 95% identity at least 96% identity at least 97% identity at least 99% identity to the SEQ ID NO: 1 herein.

141. The composition of any of paragraphs 92-140, wherein the endoglucoanase has a Melting Point (DSC) above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

142. The composition process of paragraphs 92-141, wherein the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 3, 4, 5, 6, or 7 herein.

143. The composition process of paragraphs 92-142, wherein the endoglucanase has at least 80% identity to the mature part of the polypeptide of SEQ ID NO: 3 herein.

144. The composition process of paragraphs 92-143, wherein the endoglucanase has at least 90% identity to the mature part of the polypeptide of SEQ ID NO: 3 herein having a Melting Point (DSC) above 70° C.

145. The composition of any of paragraphs 92-144, wherein the *Pyrococcus furiosus* protease (SEQ ID NO: 13 herein) and/or *Thermoascus aurantiacus* protease (SEQ ID NO: 2 herein), or a variant thereof, is the mature protease or corresponding mature protease having at least 80% identity, at least 90% identity, at least 95% identity at least 96% identity at least 97% identity at least 99% identity to the SEQ ID NO: 2 or SEQ ID NO: 13, respectively.

146. The composition of any of paragraphs 92-145, wherein the *Penicillium oxalicum* glucoamylase (SEQ ID NO: 14 herein), or a variant thereof, is the mature glucoamylase or corresponding mature glucoamylase having at least 80% identity, at least 90% identity, at least 95% identity at least 96% identity at least 97% identity at least 99% identity to the SEQ ID NO: 14 herein.

147. A polypeptides having endoglucanase activity, selected from the group consisting of:
(a) a polypeptide having at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4;
(b) a fragment of the polypeptide of (a) that has endoglucanase activity.

148. The polypeptide of paragraph 147, comprising or consisting of SEQ ID NO: 4 or the mature polypeptide of SEQ ID NO: 4.

149. The polypeptide of any of paragraphs 147 or 148, wherein the mature polypeptide is amino acids 19 to 334 of SEQ ID NO: 4.

150. A composition comprising the polypeptide of any of paragraphs 147-149.

151. A polynucleotide encoding the polypeptide of any of paragraphs 147-149.

152. A nucleic acid construct or expression vector comprising the polynucleotide of paragraph 151 operably linked to one or more control sequences that direct the production of the polypeptide in an expression host.

153. A recombinant host cell comprising the polynucleotide of paragraph 151 operably linked to one or more control sequences that direct the production of the polypeptide.

154. A method of producing the polypeptide of any of paragraphs 147-149, comprising:
(a) cultivating a cell, which in its wild-type form produces the polypeptide, under conditions conducive for production of the polypeptide; and
(b) recovering the polypeptide.

155. A method of producing a polypeptide having endoglucanase activity, comprising:
(a) cultivating the host cell of paragraph 153 under conditions conducive for production of the polypeptide; and
(b) recovering the polypeptide.

156. A transgenic plant, plant part or plant cell comprising a polynucleotide encoding the polypeptide of any of paragraphs 147-149.

157. A method of producing a polypeptide having endoglucanase activity, comprising:
(a) cultivating the transgenic plant or plant cell of paragraph 156 under conditions conducive for production of the polypeptide; and
(b) recovering the polypeptide.

158. A method of producing a protein, comprising:
(a) cultivating a recombinant host cell comprising a gene encoding a protein operably linked to the polynucleotide of paragraph 5, wherein the gene is foreign to the polynucleotide encoding the signal peptide, under conditions conducive for production of the protein; and
(b) recovering the protein.

159. A process for degrading a cellulosic material, comprising: treating the cellulosic material with an enzyme composition in the presence of the polypeptide having endoglucanase activity of any of paragraphs 1-3.

160. A process for producing a fermentation product, comprising:

(a) saccharifying a cellulosic material with an enzyme composition in the presence of the polypeptide having endoglucanase activity of any of paragraphs 147-149;

(b) fermenting the saccharified cellulosic material with one or more fermenting microorganisms to produce the fermentation product; and (c) recovering the fermentation product from the fermentation.

161. A process of fermenting a cellulosic material, comprising: fermenting the cellulosic material with one or more fermenting microorganisms, wherein the cellulosic material is saccharified with an enzyme composition in the presence of the polypeptide having endoglucanase activity of any of paragraphs 147-149.

162. The process of paragraph 161, wherein the fermenting of the cellulosic material produces a fermentation product.

163. A polypeptides having endoglucanase activity, selected from the group consisting of:

(a) a polypeptide having at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 5;

(b) a fragment of the polypeptide of (a) that has endoglucanase activity.

164. The polypeptide of paragraph 163, comprising or consisting of SEQ ID NO: 5 or the mature polypeptide of SEQ ID NO: 5.

165. The polypeptide of paragraphs 163 or 164, wherein the mature polypeptide is amino acids 21 to 394 of SEQ ID NO: 5.

166. A composition comprising the polypeptide of any of paragraphs 1-3.

167. A polynucleotide encoding the polypeptide of any of paragraphs 163-165.

168. A nucleic acid construct or expression vector comprising the polynucleotide of paragraph 167 operably linked to one or more control sequences that direct the production of the polypeptide in an expression host.

169. A recombinant host cell comprising the polynucleotide of paragraph 167 operably linked to one or more control sequences that direct the production of the polypeptide.

170. A method of producing the polypeptide of any of paragraphs 163-165, comprising:

(a) cultivating a cell, which in its wild-type form produces the polypeptide, under conditions conducive for production of the polypeptide; and (b) recovering the polypeptide.

171. A method of producing a polypeptide having endoglucanase activity, comprising:

(a) cultivating the host cell of paragraph 169 under conditions conducive for production of the polypeptide; and (b) recovering the polypeptide.

172. A transgenic plant, plant part or plant cell comprising a polynucleotide encoding the polypeptide of any of paragraphs 163-165.

173. A method of producing a polypeptide having endoglucanase activity, comprising:

(a) cultivating the transgenic plant or plant cell of paragraph 172 under conditions conducive for production of the polypeptide; and (b) recovering the polypeptide.

174. A method of producing a protein, comprising:

(a) cultivating a recombinant host cell comprising a gene encoding a protein operably linked to the polynucleotide of paragraph 167, wherein the gene is foreign to the polynucleotide encoding the signal peptide, under conditions conducive for production of the protein; and (b) recovering the protein.

175. A process for degrading a cellulosic material, comprising: treating the cellulosic material with an enzyme composition in the presence of the polypeptide having endoglucanase activity of any of paragraphs 163-165.

176. A process for producing a fermentation product, comprising:

(a) saccharifying a cellulosic material with an enzyme composition in the presence of the polypeptide having endoglucanase activity of any of paragraphs 163-165;

(b) fermenting the saccharified cellulosic material with one or more fermenting microorganisms to produce the fermentation product; and (c) recovering the fermentation product from the fermentation.

178. A process of fermenting a cellulosic material, comprising: fermenting the cellulosic material with one or more fermenting microorganisms, wherein the cellulosic material is saccharified with an enzyme composition in the presence of the polypeptide having endoglucanase activity of any of paragraphs 163-165.

179. The process of paragraph 178, wherein the fermenting of the cellulosic material produces a fermentation product.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A process for producing ethanol from starch-containing material comprising the steps of:
   i) liquefying the starch-containing material at a temperature from 75-95° at a pH from 4-6 using:
      an alpha-amylase; and
      a polypeptide having endoglucanase activity and a Melting Point (DSC) above 80° C., wherein the polypeptide is a GH5 family endoglucanase;
   ii) saccharifying using a glucoamylase; and
   iii) fermenting using a fermenting organism.

2. The process of claim 1, wherein the alpha-amylase has at least 90% sequence identity to the polypeptide of SEQ ID NO: 1.

3. The process of claim 2, wherein the alpha-amylase has at least 95% sequence identity to the polypeptide of SEQ ID NO: 1.

4. The process of claim 1, wherein the alpha-amylase has a T½ (min) at pH 4.5, 85° C., 0.12 mM $CaCl_2$) of at least 10.

5. The process of claim 1, further wherein a protease is present or added in liquefaction, wherein the protease has a thermostability value of more than 25% determined as Relative Activity at 80° C./70° C.

6. The process of claim 1, wherein the protease has at least 90%, but less than 100%, sequence identity to the mature polypeptide of SEQ ID NO: 2.

7. The process of claim 6, wherein the protease has at least 90% sequence identity to the polypeptide of SEQ ID NO: 13.

8. The process of claim 6, wherein the protease has at least 95% sequence identity to the polypeptide of SEQ ID NO: 13.

9. The process of claim 1, further glucoamylase having a heat stability at 85° C., pH 5.3, of at least 20% is present or added during liquefaction step i).

10. The process of claim 9, wherein the starch-containing material is corn.

11. The process of claim 9, wherein the glucoamylase has at least 90% sequence identity to the polypeptide of SEQ ID NO: 9 or at least 90% sequence identity to the mature polypeptide of SEQ ID NO: 14.

12. The process of claim 9, wherein the glucoamylase has at least 95% sequence identity to the polypeptide of SEQ ID NO: 9 or SEQ ID NO: 14.

13. A process of producing liquefied starch, comprising liquefying a starch-containing material with a composition comprising:
   i) an alpha-amylase;
   ii) a polypeptide having endoglucanase activity and a Melting Point (DSC) above 80° C., wherein the polypeptide is a GH5 family endoglucanase;

iii) a protease; and
iv) optionally a glucoamylase.

14. The process of claim 13, wherein the alpha-amylase has at least 90% sequence identity to the polypeptide of SEQ ID NO: 1.

15. The process of claim 13, wherein the alpha-amylase has a T½ (min) at pH 4.5, 85° C., 0.12 mM $CaCl_2$) of at least 10.

16. The process of claim 13, wherein the protease has a thermostability value of more than 25% determined as Relative Activity at 80° C./70° C.

17. The process of claim 13, wherein the protease has at least 90%, but less than 100%, sequence identity to the mature polypeptide of SEQ ID NO: 2.

18. The process of claim 13, wherein the protease has at least 90% sequence identity to the polypeptide of SEQ ID NO: 13.

19. The process of claim 13, wherein the carbohydrate-source generating enzyme is present and is a glucoamylase having a heat stability at 85° C., pH 5.3, of at least 20%.

20. The process of claim 19, wherein the glucoamylase has at least 90% sequence identity to the polypeptide of SEQ ID NO: 9 or at least 90% sequence identity to the mature polypeptide of SEQ ID NO: 14.

* * * * *

SEQUENCE LISTING

```
<160> NUMBER OF SEQ ID NOS: 33

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1
```

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
            165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
            245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
        290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415
```

```
Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 2
<211> LENGTH: 177
<212> TYPE: PRT
<213> ORGANISM: Thermoascus aurantiacus

<400> SEQUENCE: 2

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
    50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
    130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 3
<211> LENGTH: 409
<212> TYPE: PRT
<213> ORGANISM: Talaromyces leycettanus
<220> FEATURE:
<221> NAME/KEY: SIGNAL
<222> LOCATION: (1)..(18)
<220> FEATURE:
<221> NAME/KEY: mat_peptide
<222> LOCATION: (19)..(409)

<400> SEQUENCE: 3

Met Lys Phe Ser Asn Val Ile Leu Ala Ala Ser Ala Ser Ser Leu Val
```

```
              -15              -10               -5
Leu Ala Ala Pro Lys Ser Lys Thr Lys Arg Thr Ser Ala Phe Gln Trp
    -1  1           5                   10

Phe Gly Ala Asn Glu Ser Gly Ala Glu Phe Gly Asn Gln Asn Ile Pro
15              20                  25                  30

Gly Thr Leu Gly Thr Asp Tyr Thr Trp Pro Asp Thr Ser Thr Ile Gln
                35                  40                  45

Thr Leu Arg Asn Ala Gly Met Asn Ile Phe Arg Val Pro Phe Leu Met
            50                  55                  60

Glu Arg Leu Val Pro Asn Gln Met Thr Gly Ser Pro Asp Pro Thr Tyr
        65                  70                  75

Leu Ala Asp Leu Lys Ser Thr Val Asn Phe Ile Thr Gly Thr Gly Ala
    80                  85                  90

Tyr Ala Val Val Asp Pro His Asn Tyr Gly Arg Tyr Tyr Asn Asn Ile
95              100                 105                 110

Ile Thr Ser Thr Ser Asp Phe Ala Ala Phe Trp Thr Thr Val Ala Ser
                115                 120                 125

Gln Phe Ala Ser Asn Pro Arg Val Ile Phe Asp Thr Asn Asn Glu Tyr
            130                 135                 140

Asn Asn Met Asp Gln Thr Leu Val Leu Asn Leu Asn Gln Ala Ala Ile
        145                 150                 155

Asn Ala Ile Arg Ala Ala Gly Ala Thr Ser Gln Tyr Ile Phe Ala Glu
    160                 165                 170

Gly Asn Ser Trp Thr Gly Ala Trp Thr Trp Thr Ser Val Asn Asp Asn
175                 180                 185                 190

Met Lys Gln Leu Thr Asp Pro Ser Asn Lys Leu Val Tyr Glu Met His
                195                 200                 205

Gln Tyr Leu Asp Ser Asp Gly Ser Gly Thr Ser Asp Gln Cys Val Asn
            210                 215                 220

Ser Thr Ile Gly Tyr Asp Arg Ile Val Ser Ala Thr Gln Trp Leu Gln
        225                 230                 235

Ala Asn Gly Lys Val Ala Phe Leu Gly Glu Phe Ala Gly Gly Ser Asn
    240                 245                 250

Ser Val Cys Glu Ala Ala Val Thr Gly Met Leu Asp Tyr Met Glu Gln
255                 260                 265                 270

Asn Ser Asp Val Trp Leu Gly Ala Glu Trp Trp Ala Ala Gly Pro Trp
                275                 280                 285

Trp Gly Asn Tyr Ile Tyr Ser Met Glu Pro Pro Ser Gly Ile Ala Tyr
            290                 295                 300

Gln Asn Tyr Leu Ser Ile Leu Glu Pro Tyr Phe Pro Gly Gly Ser Tyr
        305                 310                 315

Ser Gly Gly Thr Gly Ser Gly Ser Gly Ser Thr Thr Thr Ala Thr Thr
    320                 325                 330

Thr Thr Thr Thr Lys Val Pro Pro Thr Ser Thr Thr Ser Ser Ala Ser
335                 340                 345                 350

Ser Thr Gly Thr Gly Val Ala Gln His Trp Gly Gln Cys Gly Gly Gln
                355                 360                 365

Gly Trp Thr Gly Pro Thr Thr Cys Val Ser Pro Tyr Thr Cys Gln Glu
            370                 375                 380

Leu Asn Pro Tyr Tyr Gln Cys Leu
        385                 390

<210> SEQ ID NO 4
```

```
<211> LENGTH: 334
<212> TYPE: PRT
<213> ORGANISM: Penicillium capsulatum
<220> FEATURE:
<221> NAME/KEY: SIGNAL
<222> LOCATION: (1)..(18)
<220> FEATURE:
<221> NAME/KEY: mat_peptide
<222> LOCATION: (19)..(334)

<400> SEQUENCE: 4
```

Met Lys Phe Ser Asn Leu Val Ala Leu Ala Ala Ala Ser Ser Ala
            -15                 -10                 -5

Met Ala Leu Pro Leu Thr Lys Lys His Ala Lys Arg Ala Ser Ser Phe
 -1   1               5                  10

Glu Trp Phe Gly Ser Asn Glu Ser Gly Ala Glu Phe Gly Ser Gly Asn
 15                  20                  25                  30

Ile Pro Gly Val Tyr Gly Thr Asp Tyr Ile Phe Pro Ser Thr Ser Ala
                 35                  40                  45

Ile Gln Thr Leu Ile Asn Asn Gly Met Asn Ile Phe Arg Val Thr Phe
             50                  55                  60

Met Met Glu Arg Leu Val Pro Asn Thr Met Thr Gly Ser Phe Asp Ala
             65                  70                  75

Glu Tyr Leu Ser Asn Leu Thr Ser Val Val Asn Tyr Ile Thr Glu Ala
 80                  85                  90

Gly Ala His Ala Val Ile Asp Pro His Asn Tyr Gly Arg Tyr Tyr Gly
 95                  100                 105                 110

Ser Ile Ile Ser Ser Thr Ser Asp Phe Gln Thr Phe Trp Lys Asn Val
                 115                 120                 125

Ala Gly Gln Phe Lys Ser Asn Ser Leu Val Ile Phe Asp Thr Asn Asn
             130                 135                 140

Glu Tyr His Asp Met Asp Gln Thr Leu Val Leu Asn Leu Asn Gln Ala
             145                 150                 155

Ala Ile Asn Gly Ile Arg Ala Ala Gly Ala Thr Ser Gln Tyr Ile Phe
             160                 165                 170

Val Glu Gly Asn Ser Tyr Thr Gly Ala Trp Thr Trp Ala Asp Val Asn
175                 180                 185                 190

Asp Asn Leu Lys Asn Leu Thr Asp Pro Gln Asn Lys Ile Val Tyr Glu
                 195                 200                 205

Met His Gln Tyr Leu Asp Ser Asp Gly Ser Gly Thr Ser Ala Thr Cys
             210                 215                 220

Val Ser Thr Thr Ile Gly Lys Glu Arg Val Thr Ser Ala Thr Gln Trp
             225                 230                 235

Leu Gln Lys Asn Gly Lys Val Gly Ile Leu Gly Glu Phe Ala Gly Gly
     240                 245                 250

Val Asn Asp Gln Cys Lys Thr Ala Ile Thr Gly Met Leu Ser Tyr Leu
255                 260                 265                 270

Glu Asp Asn Ser Asp Val Trp Arg Gly Ala Met Trp Trp Ala Ala Gly
                 275                 280                 285

Pro Trp Trp Gly Asp Tyr Ile Phe Ser Leu Glu Pro Pro Ser Gly Thr
             290                 295                 300

Ala Tyr Thr Gly Met Trp Ser Thr Leu Lys Ser Tyr Leu Ala
             305                 310                 315

```
<210> SEQ ID NO 5
<211> LENGTH: 394
<212> TYPE: PRT
```

```
<213> ORGANISM: Trichophaea saccata
<220> FEATURE:
<221> NAME/KEY: SIGNAL
<222> LOCATION: (1)..(20)
<220> FEATURE:
<221> NAME/KEY: mat_peptide
<222> LOCATION: (21)..(394)

<400> SEQUENCE: 5
```

Met His Ser Phe Phe Ser Leu Ala Leu Ala Val Ala Gly Leu Pro Ala
-20              -15                  -10                   -5

Leu Ile Asn Ala Gln Gln Ser Ala Trp Gly Gln Cys Gly Gly Val Gly
            -1  1                5                    10

Trp Thr Gly Ala Thr Thr Cys Val Ser Gly Tyr Tyr Cys Ser Lys Leu
            15                  20                  25

Asn Asp Tyr Tyr Ser Gln Cys Ile Pro Gly Thr Ala Ser Thr Thr Thr
            30                  35                  40

Ser Ala Val Ser Thr Thr Thr Ala Thr Ser Pro Thr Gly Ser Val
45                  50                  55                  60

Cys Ser Gly Asn Arg Thr Lys Phe Lys Tyr Phe Gly Val Asn Glu Ser
                65                  70                  75

Gly Ala Glu Phe Gly Asn Asn Val Val Pro Gly Thr Leu Gly Lys Asp
            80                  85                  90

Tyr Thr Trp Pro Thr Thr Asp Ser Val Asp Phe Phe Leu Gly Lys Gly
            95                  100                 105

Met Asn Thr Phe Arg Ile Ala Phe Leu Met Glu Arg Leu Ser Pro Pro
            110                 115                 120

Ala Gly Gly Leu Thr Gly Thr Phe Asp Pro Thr Tyr Leu Ala Ser Leu
125                 130                 135                 140

Lys Asn Ile Ala Ser Tyr Ile Thr Gly Lys Gly Gly Tyr Ala Ile Ile
                145                 150                 155

Asp Pro His Asn Tyr Gly Arg Tyr Asn Gly Asn Ile Ile Thr Asp Tyr
                160                 165                 170

Thr Ser Phe Gly Thr Trp Cys Lys Asn Leu Ala Ser Gln Phe Lys Ser
            175                 180                 185

Asp Ser His Ile Ile Phe Asp Thr Asn Asn Glu Tyr His Asp Met Asp
            190                 195                 200

Glu Thr Leu Val Phe Asn Leu Asn Gln Ala Cys Ile Asn Gly Ile Arg
205                 210                 215                 220

Ala Ala Gly Ala Thr Ser Gln Leu Ile Leu Ile Glu Gly Asn Ser Trp
                225                 230                 235

Thr Gly Ala Trp Thr Trp Ile Ser Ser Gly Asn Ala Ala Ser Leu Ile
            240                 245                 250

Asn Leu Thr Asp Pro Asn Asn Asn Ile Ala Tyr Glu Met His Gln Tyr
            255                 260                 265

Leu Asp Ser Asp Gly Ser Gly Thr Ser Pro Thr Cys Val Ser Ser Thr
270                 275                 280

Ile Gly Ala Glu Arg Leu Ala Ala Thr Ala Trp Leu Gln Ala Asn
285                 290                 295                 300

Asn Lys Lys Gly Phe Leu Gly Glu Ile Gly Ala Gly Ser Asn Asp Asp
            305                 310                 315

Cys Ile Ala Ala Val Lys Gly Ala Leu Cys Ser Met Gln Glu Ala Gly
            320                 325                 330

Gly Val Trp Leu Gly Ala Leu Trp Trp Ala Ala Gly Pro Trp Trp Gly
            335                 340                 345

```
Asp Tyr Tyr Gln Ser Ile Glu Pro Pro Asp Gly Ala Ala Ile Ala Arg
        350                 355                 360

Ile Leu Pro Glu Ala Leu Leu Pro Phe Leu
365                 370

<210> SEQ ID NO 6
<211> LENGTH: 278
<212> TYPE: PRT
<213> ORGANISM: Thielavia terrestris
<220> FEATURE:
<221> NAME/KEY: mat_peptide
<222> LOCATION: (1)..(278)

<400> SEQUENCE: 6

Ala Ser Gly Ser Gly Gln Ser Thr Arg Tyr Trp Asp Cys Cys Lys Pro
1               5                   10                  15

Ser Cys Ala Trp Pro Gly Lys Ala Val Ser Gln Pro Val Tyr Ala
            20                  25                  30

Cys Asp Ala Asn Phe Gln Arg Leu Ser Asp Phe Asn Val Gln Ser Gly
            35                  40                  45

Cys Asn Gly Gly Ser Ala Tyr Ser Cys Ala Asp Gln Thr Pro Trp Ala
50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn His Phe Asp Ile Ala Met Pro Gly Gly
        115                 120                 125

Gly Val Gly Ile Phe Asn Gly Cys Ser Ser Gln Phe Gly Gly Leu Pro
    130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
        195                 200                 205

Pro Val Phe Thr Pro Pro Ser Gly Gly Asn Gly Thr Gly Thr Pro
    210                 215                 220

Thr Ser Thr Ala Pro Gly Ser Gly Gln Thr Ser Pro Gly Gly Ser
225                 230                 235                 240

Gly Cys Thr Ser Gln Lys Trp Ala Gln Cys Gly Gly Ile Gly Phe Ser
                245                 250                 255

Gly Cys Thr Thr Cys Val Ser Gly Thr Thr Cys Gln Lys Leu Asn Asp
            260                 265                 270

Tyr Tyr Ser Gln Cys Leu
        275

<210> SEQ ID NO 7
<211> LENGTH: 294
<212> TYPE: PRT
<213> ORGANISM: Sordaria fimicola
<220> FEATURE:
<221> NAME/KEY: SIGNAL
<222> LOCATION: (1)..(21)
```

<400> SEQUENCE: 7

| Met | Arg | Ser | Ser | Thr | Ile | Leu | Gln | Thr | Gly | Leu | Val | Ala | Val | Leu | Pro |
| 1 | | | | 5 | | | | | 10 | | | | | 15 | |

Phe Ala Val Gln Ala Ala Ser Gly Ser Gly Lys Ser Thr Arg Tyr Trp
              20                  25                  30

Asp Cys Cys Lys Pro Ser Cys Ala Trp Ser Gly Lys Ala Ser Val Asn
        35                  40                  45

Arg Pro Val Leu Ala Cys Asp Ala Asn Asn Pro Leu Asn Asp Ala
    50                  55                  60

Asn Val Lys Ser Gly Cys Asp Gly Gly Ser Ala Tyr Thr Cys Ala Asn
65                  70                  75                  80

Asn Ser Pro Trp Ala Val Asn Asp Asn Leu Ala Tyr Gly Phe Ala Ala
                85                  90                  95

Thr Lys Leu Ser Gly Gly Thr Glu Ser Ser Trp Cys Cys Ala Cys Tyr
                100                 105                 110

Ala Leu Thr Phe Thr Ser Gly Pro Val Ser Gly Lys Thr Leu Val Val
                115                 120                 125

Gln Ser Thr Ser Thr Gly Gly Asp Leu Gly Ser Asn His Phe Asp Leu
130                 135                 140

Asn Met Pro Gly Gly Gly Val Gly Leu Phe Asp Gly Cys Lys Arg Glu
145                 150                 155                 160

Phe Gly Gly Leu Pro Gly Ala Gln Tyr Gly Gly Ile Ser Ser Arg Ser
                165                 170                 175

Glu Cys Asp Ser Phe Pro Ala Ala Leu Lys Pro Gly Cys Gln Trp Arg
                180                 185                 190

Phe Asp Trp Phe Lys Asn Ala Asp Asn Pro Glu Phe Thr Phe Lys Gln
                195                 200                 205

Val Gln Cys Pro Ser Glu Leu Thr Ser Arg Thr Gly Cys Lys Arg Asn
                210                 215                 220

Asp Asp Ser Gln Phe Pro Ala Phe Thr Pro Pro Ser Gly Gly Gly Ser
225                 230                 235                 240

Asn Pro Ser Thr Pro Thr Thr Pro Pro Ser Ser Gly Gly Gly Ser
                245                 250                 255

Gly Cys Ala Ala Ala Met Tyr Ala Gln Cys Gly Gly Ser Gly Phe Ser
                260                 265                 270

Gly Cys Thr Asn Cys Pro Ser Gly Ser Thr Cys Lys Ala Ile Asn Asp
                275                 280                 285

Tyr Tyr His Gln Cys Ala
        290

<210> SEQ ID NO 8
<211> LENGTH: 1851
<212> TYPE: DNA
<213> ORGANISM: Penicillium oxalicum
<220> FEATURE:
<221> NAME/KEY: CDS
<222> LOCATION: (1)..(1851)

<400> SEQUENCE: 8

```
atg cgt ctc act cta tta tca ggt gta gcc ggc gtt ctc tgc gca gga      48
Met Arg Leu Thr Leu Leu Ser Gly Val Ala Gly Val Leu Cys Ala Gly
1               5                   10                  15 cag ctg acg gcg gcg cgt cct gat ccc aag ggt ggg aat ctg acg ccg      96
Gln Leu Thr Ala Ala Arg Pro Asp Pro Lys Gly Gly Asn Leu Thr Pro
            20                  25                  30
```

| | | | | | | | | | | | | | | | | |
|---|---|---|---|---|---|---|---|---|---|---|---|---|---|---|---|---|
| ttc | atc | cac | aaa | gag | ggc | gag | cgg | tcg | ctc | caa | ggc | atc | ttg | gac | aat | 144 |
| Phe | Ile | His | Lys | Glu | Gly | Glu | Arg | Ser | Leu | Gln | Gly | Ile | Leu | Asp | Asn | |
| | | 35 | | | | 40 | | | | 45 | | | | | | |
| ctc | ggt | ggg | cga | ggt | aag | aaa | aca | ccc | ggc | act | gcc | gca | ggg | ttg | ttt | 192 |
| Leu | Gly | Gly | Arg | Gly | Lys | Lys | Thr | Pro | Gly | Thr | Ala | Ala | Gly | Leu | Phe | |
| 50 | | | | | 55 | | | | | 60 | | | | | | |
| att | gcc | agt | cca | aac | aca | gag | aat | cca | aac | tat | tat | tat | aca | tgg | act | 240 |
| Ile | Ala | Ser | Pro | Asn | Thr | Glu | Asn | Pro | Asn | Tyr | Tyr | Tyr | Thr | Trp | Thr | |
| 65 | | | | | 70 | | | | | 75 | | | | | 80 | |
| cgt | gac | tca | gct | ttg | act | gcc | aag | tgc | ttg | atc | gac | ctg | ttc | gaa | gac | 288 |
| Arg | Asp | Ser | Ala | Leu | Thr | Ala | Lys | Cys | Leu | Ile | Asp | Leu | Phe | Glu | Asp | |
| | | | | 85 | | | | | 90 | | | | | 95 | | |
| tct | cgg | gca | aag | ttt | cca | att | gac | cgc | aaa | tac | ttg | gaa | aca | gga | att | 336 |
| Ser | Arg | Ala | Lys | Phe | Pro | Ile | Asp | Arg | Lys | Tyr | Leu | Glu | Thr | Gly | Ile | |
| | | | 100 | | | | | 105 | | | | | 110 | | | |
| cgg | gac | tac | gtg | tcg | tcc | caa | gca | atc | ctc | cag | agt | gtg | tct | aat | cct | 384 |
| Arg | Asp | Tyr | Val | Ser | Ser | Gln | Ala | Ile | Leu | Gln | Ser | Val | Ser | Asn | Pro | |
| | | | 115 | | | | | 120 | | | | | 125 | | | |
| tct | gga | acc | ctg | aag | gat | ggc | tct | ggt | ctg | ggt | gaa | ccc | aag | ttt | gag | 432 |
| Ser | Gly | Thr | Leu | Lys | Asp | Gly | Ser | Gly | Leu | Gly | Glu | Pro | Lys | Phe | Glu | |
| | 130 | | | | | 135 | | | | | 140 | | | | | |
| att | gac | ctg | aat | ccc | ttt | tcg | ggt | gcc | tgg | ggt | cgg | cct | cag | cgg | gat | 480 |
| Ile | Asp | Leu | Asn | Pro | Phe | Ser | Gly | Ala | Trp | Gly | Arg | Pro | Gln | Arg | Asp | |
| 145 | | | | | 150 | | | | | 155 | | | | | 160 | |
| ggc | cca | gcg | ctg | cga | gcg | acc | gct | atg | atc | acc | tac | gcc | aac | tac | ctg | 528 |
| Gly | Pro | Ala | Leu | Arg | Ala | Thr | Ala | Met | Ile | Thr | Tyr | Ala | Asn | Tyr | Leu | |
| | | | | 165 | | | | | 170 | | | | | 175 | | |
| ata | tcc | cat | ggt | cag | aaa | tcg | gat | gtg | tca | cag | gtc | atg | tgg | ccg | att | 576 |
| Ile | Ser | His | Gly | Gln | Lys | Ser | Asp | Val | Ser | Gln | Val | Met | Trp | Pro | Ile | |
| | | | 180 | | | | | 185 | | | | | 190 | | | |
| att | gcc | aat | gat | cta | gca | tat | gtt | ggt | caa | tac | tgg | aat | aat | acc | gga | 624 |
| Ile | Ala | Asn | Asp | Leu | Ala | Tyr | Val | Gly | Gln | Tyr | Trp | Asn | Asn | Thr | Gly | |
| | | | 195 | | | | | 200 | | | | | 205 | | | |
| ttt | gac | ctg | tgg | gaa | gag | gtg | gat | ggg | tca | agc | ttt | ttc | acg | att | gcg | 672 |
| Phe | Asp | Leu | Trp | Glu | Glu | Val | Asp | Gly | Ser | Ser | Phe | Phe | Thr | Ile | Ala | |
| | 210 | | | | | 215 | | | | | 220 | | | | | |
| gtc | cag | cac | cga | gcc | ctt | gtt | gaa | ggc | tcg | caa | ctg | gcg | aaa | aag | ctc | 720 |
| Val | Gln | His | Arg | Ala | Leu | Val | Glu | Gly | Ser | Gln | Leu | Ala | Lys | Lys | Leu | |
| 225 | | | | | 230 | | | | | 235 | | | | | 240 | |
| ggc | aag | tcc | tgc | gat | gcc | tgt | gat | tct | cag | cct | ccc | cag | ata | ttg | tgt | 768 |
| Gly | Lys | Ser | Cys | Asp | Ala | Cys | Asp | Ser | Gln | Pro | Pro | Gln | Ile | Leu | Cys | |
| | | | | 245 | | | | | 250 | | | | | 255 | | |
| ttc | ctg | cag | agt | ttc | tgg | aac | gga | aag | tac | atc | acc | tcc | aac | atc | aac | 816 |
| Phe | Leu | Gln | Ser | Phe | Trp | Asn | Gly | Lys | Tyr | Ile | Thr | Ser | Asn | Ile | Asn | |
| | | | 260 | | | | | 265 | | | | | 270 | | | |
| acg | caa | gca | agc | cgc | tct | ggt | atc | gac | ctg | gac | tct | gtc | ctg | gga | agc | 864 |
| Thr | Gln | Ala | Ser | Arg | Ser | Gly | Ile | Asp | Leu | Asp | Ser | Val | Leu | Gly | Ser | |
| | | 275 | | | | | 280 | | | | | 285 | | | | |
| att | cat | acc | ttt | gat | ccc | gaa | gca | gcc | tgt | gac | gat | gca | act | ttc | cag | 912 |
| Ile | His | Thr | Phe | Asp | Pro | Glu | Ala | Ala | Cys | Asp | Asp | Ala | Thr | Phe | Gln | |
| | 290 | | | | | 295 | | | | | 300 | | | | | |
| cct | tgt | tct | gcc | cgc | gct | ctg | gcg | aac | cac | aag | gtc | tat | gtg | gat | tcc | 960 |
| Pro | Cys | Ser | Ala | Arg | Ala | Leu | Ala | Asn | His | Lys | Val | Tyr | Val | Asp | Ser | |
| 305 | | | | | 310 | | | | | 315 | | | | | 320 | |
| ttc | cgc | tct | atc | tac | aag | att | aat | gcg | ggt | ctt | gca | gag | gga | tcg | gct | 1008 |
| Phe | Arg | Ser | Ile | Tyr | Lys | Ile | Asn | Ala | Gly | Leu | Ala | Glu | Gly | Ser | Ala | |
| | | | | 325 | | | | | 330 | | | | | 335 | | |
| gcc | aac | gtt | ggc | cgc | tac | ccc | gag | gat | gtt | tac | caa | gga | ggc | aat | cca | 1056 |
| Ala | Asn | Val | Gly | Arg | Tyr | Pro | Glu | Asp | Val | Tyr | Gln | Gly | Gly | Asn | Pro | |
| | | | 340 | | | | | 345 | | | | | 350 | | | |

```
tgg tat ctc gcc acc cta ggc gca tct gaa ttg ctt tac gac gcc ttg      1104
Trp Tyr Leu Ala Thr Leu Gly Ala Ser Glu Leu Leu Tyr Asp Ala Leu
            355                 360                 365 tac cag tgg gac aga ctt ggc aaa ctt gaa gtc tcg gag acc tcg ttg      1152
Tyr Gln Trp Asp Arg Leu Gly Lys Leu Glu Val Ser Glu Thr Ser Leu
        370                 375                 380 tca ttc ttc aaa gac ttt gac gcg acc gtg aaa att ggc tcg tac tcg      1200
Ser Phe Phe Lys Asp Phe Asp Ala Thr Val Lys Ile Gly Ser Tyr Ser
385                 390                 395                 400 agg aac agc aag acc tac aag aaa ttg acc cag tcc atc aag tcg tac      1248
Arg Asn Ser Lys Thr Tyr Lys Lys Leu Thr Gln Ser Ile Lys Ser Tyr
                405                 410                 415 gcg gac ggg ttc atc cag tta gtg cag cag tac act cct tct aat gga      1296
Ala Asp Gly Phe Ile Gln Leu Val Gln Gln Tyr Thr Pro Ser Asn Gly
            420                 425                 430 tct ctg gcc gag caa tac gat cgc aat acg gct gct cct ctc tct gca      1344
Ser Leu Ala Glu Gln Tyr Asp Arg Asn Thr Ala Ala Pro Leu Ser Ala
        435                 440                 445 aac gat ctg act tgg tca ttt gcc tct ttc ttg acg gct acg caa cgc      1392
Asn Asp Leu Thr Trp Ser Phe Ala Ser Phe Leu Thr Ala Thr Gln Arg
    450                 455                 460 cgc gat gcc gtg gtt cct ccc tcc tgg ggc gca aag tcg gca aac aaa      1440
Arg Asp Ala Val Val Pro Pro Ser Trp Gly Ala Lys Ser Ala Asn Lys
465                 470                 475                 480 gtc cca acc act tgt tca gcc tcc cct gtt gtg ggt act tat aag gcg      1488
Val Pro Thr Thr Cys Ser Ala Ser Pro Val Val Gly Thr Tyr Lys Ala
                485                 490                 495 ccc acg gca act ttc tca tcc aag act aag tgc gtc ccc gct aaa gat      1536
Pro Thr Ala Thr Phe Ser Ser Lys Thr Lys Cys Val Pro Ala Lys Asp
            500                 505                 510 att gtg cct atc acg ttc tac ctg att gag aac act tac tat gga gag      1584
Ile Val Pro Ile Thr Phe Tyr Leu Ile Glu Asn Thr Tyr Tyr Gly Glu
        515                 520                 525 aac gtc ttc atg agt ggc aac att act gcg ctg ggt aac tgg gac gcc      1632
Asn Val Phe Met Ser Gly Asn Ile Thr Ala Leu Gly Asn Trp Asp Ala
    530                 535                 540 aag aaa ggc ttc cca ctc acc gca aac ctc tac acg caa gat caa aac      1680
Lys Lys Gly Phe Pro Leu Thr Ala Asn Leu Tyr Thr Gln Asp Gln Asn
545                 550                 555                 560 ttg tgg ttc gcc agt gtc gag ttc atc cca gca ggc aca ccc ttt gag      1728
Leu Trp Phe Ala Ser Val Glu Phe Ile Pro Ala Gly Thr Pro Phe Glu
                565                 570                 575 tac aag tac tac aag gtc gag ccc aat ggc gat att act tgg gag aag      1776
Tyr Lys Tyr Tyr Lys Val Glu Pro Asn Gly Asp Ile Thr Trp Glu Lys
            580                 585                 590 ggt ccc aac cgg gtg ttc gtc gct ccc acg gga tgc cca gtt cag cct      1824
Gly Pro Asn Arg Val Phe Val Ala Pro Thr Gly Cys Pro Val Gln Pro
        595                 600                 605 cac tcc aac gac gtg tgg cag ttt tga                                  1851
His Ser Asn Asp Val Trp Gln Phe
    610                 615

<210> SEQ ID NO 9
<211> LENGTH: 616
<212> TYPE: PRT
<213> ORGANISM: Penicillium oxalicum

<400> SEQUENCE: 9

Met Arg Leu Thr Leu Leu Ser Gly Val Ala Gly Val Leu Cys Ala Gly
1               5                   10                  15
```

```
Gln Leu Thr Ala Ala Arg Pro Asp Pro Lys Gly Gly Asn Leu Thr Pro
                20                  25                  30

Phe Ile His Lys Glu Gly Glu Arg Ser Leu Gln Gly Ile Leu Asp Asn
            35                  40                  45

Leu Gly Gly Arg Gly Lys Lys Thr Pro Gly Thr Ala Ala Gly Leu Phe
     50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
                100                 105                 110

Arg Asp Tyr Val Ser Ser Gln Ala Ile Leu Gln Ser Val Ser Asn Pro
            115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Gln Ile Leu Cys
                245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
        275                 280                 285

Ile His Thr Phe Asp Pro Glu Ala Ala Cys Asp Asp Ala Thr Phe Gln
    290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
    355                 360                 365

Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
            420                 425                 430
```

```
Ser Leu Ala Glu Gln Tyr Asp Arg Asn Thr Ala Ala Pro Leu Ser Ala
            435                 440                 445

Asn Asp Leu Thr Trp Ser Phe Ala Ser Phe Leu Thr Ala Thr Gln Arg
450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
                500                 505                 510

Ile Val Pro Ile Thr Phe Tyr Leu Ile Glu Asn Thr Tyr Tyr Gly Glu
            515                 520                 525

Asn Val Phe Met Ser Gly Asn Ile Thr Ala Leu Gly Asn Trp Asp Ala
        530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
                580                 585                 590

Gly Pro Asn Arg Val Phe Val Ala Pro Thr Gly Cys Pro Val Gln Pro
            595                 600                 605

His Ser Asn Asp Val Trp Gln Phe
        610                 615

<210> SEQ ID NO 10
<211> LENGTH: 4014
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: misc_signal
<222> LOCATION: (1)..(81)
<220> FEATURE:
<221> NAME/KEY: mat_peptide
<222> LOCATION: (82)..(4014)

<400> SEQUENCE: 10 atg agg cgg gtg gtt gcc ctc ttc att gca att ttg atg ctt gga agc     48
Met Arg Arg Val Val Ala Leu Phe Ile Ala Ile Leu Met Leu Gly Ser
        -25                 -20                 -15 atc gtt gga gcg aac gtt aag agc gtt ggc gcg gcg gag ccg aag ccg     96
Ile Val Gly Ala Asn Val Lys Ser Val Gly Ala Ala Glu Pro Lys Pro
    -10                  -5                  -1  1               5 ctc aac gtc ata ata gtc tgg cac cag cac cag ccc tac tac tac gac    144
Leu Asn Val Ile Ile Val Trp His Gln His Gln Pro Tyr Tyr Tyr Asp
                10                  15                  20 cct gtc cag gac gtc tac acc agg ccc tgg gtc agg ctc cac gcg gcg    192
Pro Val Gln Asp Val Tyr Thr Arg Pro Trp Val Arg Leu His Ala Ala
            25                  30                  35 aac aac tac tgg aag atg gcc cac tac ctg agc cag tac ccg gag gtt    240
Asn Asn Tyr Trp Lys Met Ala His Tyr Leu Ser Gln Tyr Pro Glu Val
        40                  45                  50 cac gcc acc att gac ctc tcg ggt tcg ctg ata gcc cag ctt gcc gac    288
His Ala Thr Ile Asp Leu Ser Gly Ser Leu Ile Ala Gln Leu Ala Asp
    55                  60                  65 tac atg aac ggc aag aag gac acc tac cag ata atc acc gag aag ata    336
Tyr Met Asn Gly Lys Lys Asp Thr Tyr Gln Ile Ile Thr Glu Lys Ile
```

```
                        70                     75                      80                      85
gcc aac ggg gaa ccc ctc acc gtc gac gag aag tgg ttc atg ctc cag        384
Ala Asn Gly Glu Pro Leu Thr Val Asp Glu Lys Trp Phe Met Leu Gln
                     90                      95                     100 gca ccg gga ggg ttc ttc gac aac acc atc ccc tgg aac ggt gaa ccg        432
Ala Pro Gly Gly Phe Phe Asp Asn Thr Ile Pro Trp Asn Gly Glu Pro
                105                     110                     115 ata acc gac ccc aac ggc aac ccg ata agg gac ttc tgg gac cgc tac        480
Ile Thr Asp Pro Asn Gly Asn Pro Ile Arg Asp Phe Trp Asp Arg Tyr
            120                     125                     130 acg gag ctg aag aac aag atg ctc agc gca aag gcc aag tac gca aac        528
Thr Glu Leu Lys Asn Lys Met Leu Ser Ala Lys Ala Lys Tyr Ala Asn
        135                     140                     145 ttc gtg act gag agc cag aag gtc gct gtg acg aac gag ttc aca gag        576
Phe Val Thr Glu Ser Gln Lys Val Ala Val Thr Asn Glu Phe Thr Glu
150                     155                     160                     165 cag gac tac ata gac cta gcg gtt ctc ttc aat ctc gct tgg att gac        624
Gln Asp Tyr Ile Asp Leu Ala Val Leu Phe Asn Leu Ala Trp Ile Asp
                    170                     175                     180 tac aat tac atc acg agc acg ccg gag ttc aag gcc ctc tac gac aag        672
Tyr Asn Tyr Ile Thr Ser Thr Pro Glu Phe Lys Ala Leu Tyr Asp Lys
                185                     190                     195 gtt gac gag ggc ggc tat aca agg gcg gac gtc aaa acc gtt ctc gac        720
Val Asp Glu Gly Gly Tyr Thr Arg Ala Asp Val Lys Thr Val Leu Asp
            200                     205                     210 gcc cag atc tgg ctt ctc aac cac acc ttc gag gag cac gag aag ata        768
Ala Gln Ile Trp Leu Leu Asn His Thr Phe Glu Glu His Glu Lys Ile
        215                     220                     225 aac ctc ctc ctc gga aac ggc aac gtc gag gtc acg gtc gtt ccc tac        816
Asn Leu Leu Leu Gly Asn Gly Asn Val Glu Val Thr Val Val Pro Tyr
230                     235                     240                     245 gcc cac ccg ata ggc ccg ata ctc aac gac ttc ggc tgg gac agc gac        864
Ala His Pro Ile Gly Pro Ile Leu Asn Asp Phe Gly Trp Asp Ser Asp
                    250                     255                     260 ttc aac gac cag gtc aag aag gcc gac gaa ctg tac aag ccg tac ctc        912
Phe Asn Asp Gln Val Lys Lys Ala Asp Glu Leu Tyr Lys Pro Tyr Leu
                265                     270                     275 ggc ggc ggc acc gcg gtt cca aaa ggc gga tgg gcg gct gag agc gcc        960
Gly Gly Gly Thr Ala Val Pro Lys Gly Gly Trp Ala Ala Glu Ser Ala
            280                     285                     290 ctc aac gac aaa act ctg gag atc ctc gcc gag aac ggc tgg gag tgg       1008
Leu Asn Asp Lys Thr Leu Glu Ile Leu Ala Glu Asn Gly Trp Glu Trp
        295                     300                     305 gtc atg acc gac cag atg gtt ctc gga aag ctc ggc att gag gga acc       1056
Val Met Thr Asp Gln Met Val Leu Gly Lys Leu Gly Ile Glu Gly Thr
310                     315                     320                     325 gtc gag aac tac cac aag ccc tgg gtg gcc gag ttc aac gga aag aag       1104
Val Glu Asn Tyr His Lys Pro Trp Val Ala Glu Phe Asn Gly Lys Lys
                    330                     335                     340 ata tac ctc ttc cca aga aat cac gat cta agt gac aga gtt ggc ttt       1152
Ile Tyr Leu Phe Pro Arg Asn His Asp Leu Ser Asp Arg Val Gly Phe
                345                     350                     355 acc tac agc gga atg aac cag cag cag gcc gtt gag gac ttc gtc aac       1200
Thr Tyr Ser Gly Met Asn Gln Gln Gln Ala Val Glu Asp Phe Val Asn
            360                     365                     370 gag ctc ctc aag ctc cag aag cag aac tac gat ggc tcg ctg gtt tac       1248
Glu Leu Leu Lys Leu Gln Lys Gln Asn Tyr Asp Gly Ser Leu Val Tyr
        375                     380                     385 gtg gtc acg ctc gac ggc gag aac ccc gtg gag aac tac ccc tac gac       1296
Val Val Thr Leu Asp Gly Glu Asn Pro Val Glu Asn Tyr Pro Tyr Asp
```

-continued

| | | |
|---|---|---|
| Val Val Thr Leu Asp Gly Glu Asn Pro Val Glu Asn Tyr Pro Tyr Asp<br>390                        395                    400                      405 | |
| ggg gag ctc ttc ctc acc gaa ctc tac aag aag ctg acc gaa ctc cag<br>Gly Glu Leu Phe Leu Thr Glu Leu Tyr Lys Lys Leu Thr Glu Leu Gln<br>                410                    415                    420 | 1344 |
| gag cag ggt ctc ata aga acc ctc acc ccg agc gag tac atc cag ctc<br>Glu Gln Gly Leu Ile Arg Thr Leu Thr Pro Ser Glu Tyr Ile Gln Leu<br>                425                    430                    435 | 1392 |
| tac ggc gac aag gcc aac aag ctc aca cct cgg atg atg gag cgc ctt<br>Tyr Gly Asp Lys Ala Asn Lys Leu Thr Pro Arg Met Met Glu Arg Leu<br>                440                    445                    450 | 1440 |
| gac ctc acc gga gac aac gtt aac gcc ctc ctc aag gcc cag agc ctc<br>Asp Leu Thr Gly Asp Asn Val Asn Ala Leu Leu Lys Ala Gln Ser Leu<br>455                        460                    465 | 1488 |
| ggc gaa ctc tac gac atg acc ggc gtt aag gag gag atg cag tgg ccc<br>Gly Glu Leu Tyr Asp Met Thr Gly Val Lys Glu Glu Met Gln Trp Pro<br>470                        475                    480                    485 | 1536 |
| gag agc agc tgg ata gac gga acc ctc tcc acg tgg ata ggc gag ccc<br>Glu Ser Ser Trp Ile Asp Gly Thr Leu Ser Thr Trp Ile Gly Glu Pro<br>                490                    495                    500 | 1584 |
| cag gag aac tac ggc tgg tac tgg ctc tac atg gcc agg aag gcc ctt<br>Gln Glu Asn Tyr Gly Trp Tyr Trp Leu Tyr Met Ala Arg Lys Ala Leu<br>                505                    510                    515 | 1632 |
| atg gag aac aag gat aaa atg agc cag gcg gac tgg gag aag gcc tac<br>Met Glu Asn Lys Asp Lys Met Ser Gln Ala Asp Trp Glu Lys Ala Tyr<br>520                        525                    530 | 1680 |
| gag tac ctg ctc cgc gcc gag gca agc gac tgg ttc tgg tgg tac gga<br>Glu Tyr Leu Leu Arg Ala Glu Ala Ser Asp Trp Phe Trp Trp Tyr Gly<br>535                        540                    545 | 1728 |
| agc gac cag gac agc ggc cag gac tac acc ttc gac cgc tac ctg aag<br>Ser Asp Gln Asp Ser Gly Gln Asp Tyr Thr Phe Asp Arg Tyr Leu Lys<br>550                        555                    560                    565 | 1776 |
| acc tac ctc tac gag atg tac aag ctg gca gga gtc gag ccg ccg agc<br>Thr Tyr Leu Tyr Glu Met Tyr Lys Leu Ala Gly Val Glu Pro Pro Ser<br>                570                    575                    580 | 1824 |
| tac ctc ttc ggc aac tac ttc ccg gac gga gag ccc tac acc acg agg<br>Tyr Leu Phe Gly Asn Tyr Phe Pro Asp Gly Glu Pro Tyr Thr Thr Arg<br>                585                    590                    595 | 1872 |
| ggc ctg gtc gga ctc aag gac ggc gag atg aag aac ttc tcc agc atg<br>Gly Leu Val Gly Leu Lys Asp Gly Glu Met Lys Asn Phe Ser Ser Met<br>600                        605                    610 | 1920 |
| tcc ccg ctg gca aag ggc gtg agc gtc tat ttc gac ggc gag ggg ata<br>Ser Pro Leu Ala Lys Gly Val Ser Val Tyr Phe Asp Gly Glu Gly Ile<br>615                        620                    625 | 1968 |
| cac ttc ata gtg aaa ggg aac ctg gac agg ttc gag gtg agc atc tgg<br>His Phe Ile Val Lys Gly Asn Leu Asp Arg Phe Glu Val Ser Ile Trp<br>630                        635                    640                    645 | 2016 |
| gag aag gat gag cgc gtt ggc aac acg ttc acc cgc ctc caa gag aag<br>Glu Lys Asp Glu Arg Val Gly Asn Thr Phe Thr Arg Leu Gln Glu Lys<br>                650                    655                    660 | 2064 |
| ccg gac gag ttg agc tat ttc atg ttc cca ttc tca agg gac agc gtt<br>Pro Asp Glu Leu Ser Tyr Phe Met Phe Pro Phe Ser Arg Asp Ser Val<br>                665                    670                    675 | 2112 |
| ggt ctc ctc ata acc aag cac gtc gtg tac gag aac gga aag gcc gag<br>Gly Leu Leu Ile Thr Lys His Val Val Tyr Glu Asn Gly Lys Ala Glu<br>680                        685                    690 | 2160 |
| ata tac ggc gcc acc gac tac gag aag agc gag aag ctt ggg gaa gcc<br>Ile Tyr Gly Ala Thr Asp Tyr Glu Lys Ser Glu Lys Leu Gly Glu Ala<br>695                        700                    705 | 2208 |

-continued

| | |
|---|---|
| acc gtc aag aac acg agc gaa gga atc gaa gtc gtc ctt ccc ttt gac<br>Thr Val Lys Asn Thr Ser Glu Gly Ile Glu Val Val Leu Pro Phe Asp<br>710                      715                    720                  725 | 2256 |
| tac ata gaa aac ccc tcc gac ttc tac ttc gct gtc tcg acg gtc aaa<br>Tyr Ile Glu Asn Pro Ser Asp Phe Tyr Phe Ala Val Ser Thr Val Lys<br>730                         735                       740 | 2304 |
| gat gga gac ctt gag gtg ata agc act cct gtg gag ctc aag ctc ccg<br>Asp Gly Asp Leu Glu Val Ile Ser Thr Pro Val Glu Leu Lys Leu Pro<br>745                      750                    755 | 2352 |
| acc gag gtc aag gga gtc gtc ata gcc gat ata acc gac cca gaa ggc<br>Thr Glu Val Lys Gly Val Val Ile Ala Asp Ile Thr Asp Pro Glu Gly<br>760                       765                    770 | 2400 |
| gac gac cat ggg ccc gga aac tac act tat ccc acg gac aag gtc ttc<br>Asp Asp His Gly Pro Gly Asn Tyr Thr Tyr Pro Thr Asp Lys Val Phe<br>775                      780                    785 | 2448 |
| aag cca ggt gtt ttc gac ctc ctc cgc ttc agg atg ctc gaa cag acg<br>Lys Pro Gly Val Phe Asp Leu Leu Arg Phe Arg Met Leu Glu Gln Thr<br>790                      795                    800                    805 | 2496 |
| gag agc tac gtc atg gag ttc tac ttc aag gac cta ggt ggt aac ccg<br>Glu Ser Tyr Val Met Glu Phe Tyr Phe Lys Asp Leu Gly Gly Asn Pro<br>                         810                    815                    820 | 2544 |
| tgg aac gga ccc aac ggc ttc agc ctc cag ata atc gag gtc tac ctc<br>Trp Asn Gly Pro Asn Gly Phe Ser Leu Gln Ile Ile Glu Val Tyr Leu<br>825                      830                    835 | 2592 |
| gac ttc aag gac ggt gga aac agt tcg gcc att aag atg ttc ccc gac<br>Asp Phe Lys Asp Gly Gly Asn Ser Ser Ala Ile Lys Met Phe Pro Asp<br>840                       845                    850 | 2640 |
| gga ccg gga gcc aac gtc aac ctc gac ccc gag cat cca tgg gac gtt<br>Gly Pro Gly Ala Asn Val Asn Leu Asp Pro Glu His Pro Trp Asp Val<br>855                      860                    865 | 2688 |
| gcc ttc agg ata gcg ggc tgg gac tac gga aac ctc atc atc ctg ccg<br>Ala Phe Arg Ile Ala Gly Trp Asp Tyr Gly Asn Leu Ile Ile Leu Pro<br>870                      875                    880                    885 | 2736 |
| aac gga acg gcc atc cag ggc gag atg cag att tcc gca gat ccg gtt<br>Asn Gly Thr Ala Ile Gln Gly Glu Met Gln Ile Ser Ala Asp Pro Val<br>                         890                    895                    900 | 2784 |
| aag aac gcc ata ata gtc aag gtt cca aag aag tac atc gcc ata aac<br>Lys Asn Ala Ile Ile Val Lys Val Pro Lys Lys Tyr Ile Ala Ile Asn<br>                         905                    910                    915 | 2832 |
| gag gac tac ggc ctc tgg gga gac gtc ctc gtc ggc tcg cag gac ggc<br>Glu Asp Tyr Gly Leu Trp Gly Asp Val Leu Val Gly Ser Gln Asp Gly<br>                       920                    925                    930 | 2880 |
| tac ggc ccg gac aag tgg aga acg gcg gca gtg gat gcg gag cag tgg<br>Tyr Gly Pro Asp Lys Trp Arg Thr Ala Ala Val Asp Ala Glu Gln Trp<br>935                      940                    945 | 2928 |
| aag ctt gga ggt gcg gac ccg cag gca gtc ata aac ggc gtg gcc ccg<br>Lys Leu Gly Gly Ala Asp Pro Gln Ala Val Ile Asn Gly Val Ala Pro<br>950                      955                    960                    965 | 2976 |
| cgc gtc att gat gag ctg gtt ccg cag ggc ttt gaa ccg acc cag gag<br>Arg Val Ile Asp Glu Leu Val Pro Gln Gly Phe Glu Pro Thr Gln Glu<br>                         970                    975                    980 | 3024 |
| gag cag ctg agc agc tac gat gca aac gac atg aag ctc gcc act gtc<br>Glu Gln Leu Ser Ser Tyr Asp Ala Asn Asp Met Lys Leu Ala Thr Val<br>                         985                    990                    995 | 3072 |
| aag gcg ctg cta ctc ctc aag cag ggc atc gtt gtg acc gac ccg<br>Lys Ala Leu Leu Leu Leu Lys Gln Gly Ile Val Val Thr Asp Pro<br>                1000                    1005                    1010 | 3117 |
| gag gga gac gac cac ggg ccg gga acg tac acc tat ccg acg gac<br>Glu Gly Asp Asp His Gly Pro Gly Thr Tyr Thr Tyr Pro Thr Asp<br>                1015                    1020                    1025 | 3162 |

```
aaa gtt ttc aag ccc ggt gtt ttc gac ctc ctc aag ttc aag gtg      3207
Lys Val Phe Lys Pro Gly Val Phe Asp Leu Leu Lys Phe Lys Val
        1030                1035                1040 acc gag gga agc gac gac tgg acg ctg gag ttc cac ttc aaa gac      3252
Thr Glu Gly Ser Asp Asp Trp Thr Leu Glu Phe His Phe Lys Asp
        1045                1050                1055 ctc ggt gga aac ccg tgg aac ggg ccg aac ggc ttc agc ctg cag      3297
Leu Gly Gly Asn Pro Trp Asn Gly Pro Asn Gly Phe Ser Leu Gln
        1060                1065                1070 ata atc gag gta tac ttc gac ttc aag gag ggc ggg aac gtc tcg      3342
Ile Ile Glu Val Tyr Phe Asp Phe Lys Glu Gly Gly Asn Val Ser
        1075                1080                1085 gcc att aag atg ttc ccg gat ggg ccc gga agc aac gtc cgt ctt      3387
Ala Ile Lys Met Phe Pro Asp Gly Pro Gly Ser Asn Val Arg Leu
        1090                1095                1100 gat cca aat cac cca tgg gac ctg gcg ctt agg ata gcc ggc tgg      3432
Asp Pro Asn His Pro Trp Asp Leu Ala Leu Arg Ile Ala Gly Trp
        1105                1110                1115 gac tac gga aac ctg ata att ctg ccc gac gga acc gcc tac caa      3477
Asp Tyr Gly Asn Leu Ile Ile Leu Pro Asp Gly Thr Ala Tyr Gln
        1120                1125                1130 ggc gag atg cag att tcc gca gat ccg gtt aag aac gcc ata ata      3522
Gly Glu Met Gln Ile Ser Ala Asp Pro Val Lys Asn Ala Ile Ile
        1135                1140                1145 gtc aag gtt cca aag aag tac ctg aac ata tcc gac tac gga ctc      3567
Val Lys Val Pro Lys Lys Tyr Leu Asn Ile Ser Asp Tyr Gly Leu
        1150                1155                1160 tac acc gcc gtc atc gtg ggt tcc caa gac ggg tac ggc ccg gac      3612
Tyr Thr Ala Val Ile Val Gly Ser Gln Asp Gly Tyr Gly Pro Asp
        1165                1170                1175 aag tgg agg ccc gtg gcc gct gag gcc gag cag tgg aag ctc gga      3657
Lys Trp Arg Pro Val Ala Ala Glu Ala Glu Gln Trp Lys Leu Gly
        1180                1185                1190 ggc gca gac ccc cag gcg gtc ata gac aac ctc gta cca agg gtc      3702
Gly Ala Asp Pro Gln Ala Val Ile Asp Asn Leu Val Pro Arg Val
        1195                1200                1205 gtt gat gaa ctc gtg ccg gag ggc ttc aag cca acg cag gag gag      3747
Val Asp Glu Leu Val Pro Glu Gly Phe Lys Pro Thr Gln Glu Glu
        1210                1215                1220 cag ctg agc agc tac gac ctt gag aag aag acc ctg gcg acg gtg      3792
Gln Leu Ser Ser Tyr Asp Leu Glu Lys Lys Thr Leu Ala Thr Val
        1225                1230                1235 ctc atg gta ccg ctc gtc aat ggg act ggc ggc gag gaa cca acg      3837
Leu Met Val Pro Leu Val Asn Gly Thr Gly Gly Glu Glu Pro Thr
        1240                1245                1250 ccg acg gag agc cca acg gaa acg acg aca acc aca ccc agc gaa      3882
Pro Thr Glu Ser Pro Thr Glu Thr Thr Thr Thr Thr Pro Ser Glu
        1255                1260                1265 aca acc acc aca act tca acg acc acc ggc cca agc tca acg acc      3927
Thr Thr Thr Thr Thr Ser Thr Thr Thr Gly Pro Ser Ser Thr Thr
        1270                1275                1280 acc agc aca ccc ggc gga gga atc tgc ggc cca ggc att ata gcg      3972
Thr Ser Thr Pro Gly Gly Gly Ile Cys Gly Pro Gly Ile Ile Ala
        1285                1290                1295 ggc ctg gcc ctg ata ccg ctc ctc ctc aag agg agg aac tga          4014
Gly Leu Ala Leu Ile Pro Leu Leu Leu Lys Arg Arg Asn
        1300                1305                1310
```

<210> SEQ ID NO 11

```
<211> LENGTH: 1337
<212> TYPE: PRT
<213> ORGANISM: Thermococcus hydrothermalis

<400> SEQUENCE: 11
```

| | | | | | | | | | | | | | | |
|---|---|---|---|---|---|---|---|---|---|---|---|---|---|---|
| Met | Arg | Arg | Val | Val | Ala | Leu | Phe | Ile | Ala | Ile | Leu | Met | Leu | Gly | Ser |
| | | -25 | | | | -20 | | | | -15 | | | | |
| Ile | Val | Gly | Ala | Asn | Val | Lys | Ser | Val | Gly | Ala | Ala | Glu | Pro | Lys | Pro |
| -10 | | | | | -5 | | | | -1 | 1 | | | | 5 | |
| Leu | Asn | Val | Ile | Ile | Val | Trp | His | Gln | His | Gln | Pro | Tyr | Tyr | Tyr | Asp |
| | | | 10 | | | | | 15 | | | | | 20 | | |
| Pro | Val | Gln | Asp | Val | Tyr | Thr | Arg | Pro | Trp | Val | Arg | Leu | His | Ala | Ala |
| | | 25 | | | | | 30 | | | | | 35 | | | |
| Asn | Asn | Tyr | Trp | Lys | Met | Ala | His | Tyr | Leu | Ser | Gln | Tyr | Pro | Glu | Val |
| | 40 | | | | | 45 | | | | | 50 | | | | |
| His | Ala | Thr | Ile | Asp | Leu | Ser | Gly | Ser | Leu | Ile | Ala | Gln | Leu | Ala | Asp |
| 55 | | | | | 60 | | | | | 65 | | | | | |
| Tyr | Met | Asn | Gly | Lys | Lys | Asp | Thr | Tyr | Gln | Ile | Ile | Thr | Glu | Lys | Ile |
| 70 | | | | 75 | | | | | 80 | | | | | 85 | |
| Ala | Asn | Gly | Glu | Pro | Leu | Thr | Val | Asp | Glu | Lys | Trp | Phe | Met | Leu | Gln |
| | | | 90 | | | | | 95 | | | | | 100 | | |
| Ala | Pro | Gly | Gly | Phe | Phe | Asp | Asn | Thr | Ile | Pro | Trp | Asn | Gly | Glu | Pro |
| | | | 105 | | | | | 110 | | | | | 115 | | |
| Ile | Thr | Asp | Pro | Asn | Gly | Asn | Pro | Ile | Arg | Asp | Phe | Trp | Asp | Arg | Tyr |
| | | 120 | | | | | 125 | | | | | 130 | | | |
| Thr | Glu | Leu | Lys | Asn | Lys | Met | Leu | Ser | Ala | Lys | Ala | Lys | Tyr | Ala | Asn |
| | 135 | | | | | 140 | | | | | 145 | | | | |
| Phe | Val | Thr | Glu | Ser | Gln | Lys | Val | Ala | Val | Thr | Asn | Glu | Phe | Thr | Glu |
| 150 | | | | | 155 | | | | | 160 | | | | | 165 |
| Gln | Asp | Tyr | Ile | Asp | Leu | Ala | Val | Leu | Phe | Asn | Leu | Ala | Trp | Ile | Asp |
| | | | 170 | | | | | 175 | | | | | 180 | | |
| Tyr | Asn | Tyr | Ile | Thr | Ser | Thr | Pro | Glu | Phe | Lys | Ala | Leu | Tyr | Asp | Lys |
| | | | 185 | | | | | 190 | | | | | 195 | | |
| Val | Asp | Glu | Gly | Gly | Tyr | Thr | Arg | Ala | Asp | Val | Lys | Thr | Val | Leu | Asp |
| | | 200 | | | | | 205 | | | | | 210 | | | |
| Ala | Gln | Ile | Trp | Leu | Leu | Asn | His | Thr | Phe | Glu | Glu | His | Glu | Lys | Ile |
| | 215 | | | | | 220 | | | | | 225 | | | | |
| Asn | Leu | Leu | Leu | Gly | Asn | Gly | Asn | Val | Glu | Val | Thr | Val | Pro | Tyr |
| 230 | | | | | 235 | | | | | 240 | | | | | 245 |
| Ala | His | Pro | Ile | Gly | Pro | Ile | Leu | Asn | Asp | Phe | Gly | Trp | Asp | Ser | Asp |
| | | | 250 | | | | | 255 | | | | | 260 | | |
| Phe | Asn | Asp | Gln | Val | Lys | Lys | Ala | Asp | Glu | Leu | Tyr | Lys | Pro | Tyr | Leu |
| | | | 265 | | | | | 270 | | | | | 275 | | |
| Gly | Gly | Gly | Thr | Ala | Val | Pro | Lys | Gly | Gly | Trp | Ala | Ala | Glu | Ser | Ala |
| | | 280 | | | | | 285 | | | | | 290 | | | |
| Leu | Asn | Asp | Lys | Thr | Leu | Glu | Ile | Leu | Ala | Glu | Asn | Gly | Trp | Glu | Trp |
| | 295 | | | | | 300 | | | | | 305 | | | | |
| Val | Met | Thr | Asp | Gln | Met | Val | Leu | Gly | Lys | Leu | Gly | Ile | Glu | Gly | Thr |
| 310 | | | | | 315 | | | | | 320 | | | | | 325 |
| Val | Glu | Asn | Tyr | His | Lys | Pro | Trp | Val | Ala | Glu | Phe | Asn | Gly | Lys | Lys |
| | | | 330 | | | | | 335 | | | | | 340 | | |
| Ile | Tyr | Leu | Phe | Pro | Arg | Asn | His | Asp | Leu | Ser | Asp | Arg | Val | Gly | Phe |
| | | | 345 | | | | | 350 | | | | | 355 | | |
| Thr | Tyr | Ser | Gly | Met | Asn | Gln | Gln | Gln | Ala | Val | Glu | Asp | Phe | Val | Asn |

```
              360                 365                 370
Glu Leu Leu Lys Leu Gln Lys Gln Asn Tyr Asp Gly Ser Leu Val Tyr
375                 380                 385

Val Val Thr Leu Asp Gly Glu Asn Pro Val Glu Asn Tyr Pro Tyr Asp
390                 395                 400                 405

Gly Glu Leu Phe Leu Thr Glu Leu Tyr Lys Lys Leu Thr Glu Leu Gln
                    410                 415                 420

Glu Gln Gly Leu Ile Arg Thr Leu Thr Pro Ser Glu Tyr Ile Gln Leu
                425                 430                 435

Tyr Gly Asp Lys Ala Asn Lys Leu Thr Pro Arg Met Met Glu Arg Leu
            440                 445                 450

Asp Leu Thr Gly Asp Asn Val Asn Ala Leu Leu Lys Ala Gln Ser Leu
455                 460                 465

Gly Glu Leu Tyr Asp Met Thr Gly Val Lys Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
                505                 510                 515

Met Glu Asn Lys Asp Lys Met Ser Gln Ala Asp Trp Glu Lys Ala Tyr
                520                 525                 530

Glu Tyr Leu Leu Arg Ala Glu Ala Ser Asp Trp Phe Trp Trp Tyr Gly
535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                    570                 575                 580

Tyr Leu Phe Gly Asn Tyr Phe Pro Asp Gly Glu Pro Tyr Thr Thr Arg
                585                 590                 595

Gly Leu Val Gly Leu Lys Asp Gly Glu Met Lys Asn Phe Ser Ser Met
                600                 605                 610

Ser Pro Leu Ala Lys Gly Val Ser Val Tyr Phe Asp Gly Glu Gly Ile
615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                    650                 655                 660

Pro Asp Glu Leu Ser Tyr Phe Met Phe Pro Phe Ser Arg Asp Ser Val
                665                 670                 675

Gly Leu Leu Ile Thr Lys His Val Val Tyr Glu Asn Gly Lys Ala Glu
                680                 685                 690

Ile Tyr Gly Ala Thr Asp Tyr Glu Lys Ser Glu Lys Leu Gly Glu Ala
            695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                    730                 735                 740

Asp Gly Asp Leu Glu Val Ile Ser Thr Pro Val Glu Leu Lys Leu Pro
                745                 750                 755

Thr Glu Val Lys Gly Val Val Ile Ala Asp Ile Thr Asp Pro Glu Gly
                760                 765                 770

Asp Asp His Gly Pro Gly Asn Tyr Thr Tyr Pro Thr Asp Lys Val Phe
                775                 780                 785
```

```
Lys Pro Gly Val Phe Asp Leu Leu Arg Phe Arg Met Leu Glu Gln Thr
790                 795                 800                 805

Glu Ser Tyr Val Met Glu Phe Tyr Phe Lys Asp Leu Gly Gly Asn Pro
                810                 815                 820

Trp Asn Gly Pro Asn Gly Phe Ser Leu Gln Ile Ile Glu Val Tyr Leu
            825                 830                 835

Asp Phe Lys Asp Gly Gly Asn Ser Ser Ala Ile Lys Met Phe Pro Asp
        840                 845                 850

Gly Pro Gly Ala Asn Val Asn Leu Asp Pro Glu His Pro Trp Asp Val
    855                 860                 865

Ala Phe Arg Ile Ala Gly Trp Asp Tyr Gly Asn Leu Ile Ile Leu Pro
870                 875                 880                 885

Asn Gly Thr Ala Ile Gln Gly Glu Met Gln Ile Ser Ala Asp Pro Val
                890                 895                 900

Lys Asn Ala Ile Ile Val Lys Val Pro Lys Lys Tyr Ile Ala Ile Asn
            905                 910                 915

Glu Asp Tyr Gly Leu Trp Gly Asp Val Leu Val Gly Ser Gln Asp Gly
        920                 925                 930

Tyr Gly Pro Asp Lys Trp Arg Thr Ala Ala Val Asp Ala Glu Gln Trp
    935                 940                 945

Lys Leu Gly Gly Ala Asp Pro Gln Ala Val Ile Asn Gly Val Ala Pro
950                 955                 960                 965

Arg Val Ile Asp Glu Leu Val Pro Gln Gly Phe Glu Pro Thr Gln Glu
                970                 975                 980

Glu Gln Leu Ser Ser Tyr Asp Ala Asn Asp Met Lys Leu Ala Thr Val
            985                 990                 995

Lys Ala Leu Leu Leu Leu Lys Gln Gly Ile Val Val Thr Asp Pro
        1000                1005                1010

Glu Gly Asp Asp His Gly Pro Gly Thr Tyr Thr Tyr Pro Thr Asp
        1015                1020                1025

Lys Val Phe Lys Pro Gly Val Phe Asp Leu Leu Lys Phe Lys Val
        1030                1035                1040

Thr Glu Gly Ser Asp Asp Trp Thr Leu Glu Phe His Phe Lys Asp
        1045                1050                1055

Leu Gly Gly Asn Pro Trp Asn Gly Pro Asn Gly Phe Ser Leu Gln
        1060                1065                1070

Ile Ile Glu Val Tyr Phe Asp Phe Lys Glu Gly Gly Asn Val Ser
        1075                1080                1085

Ala Ile Lys Met Phe Pro Asp Gly Pro Gly Ser Asn Val Arg Leu
        1090                1095                1100

Asp Pro Asn His Pro Trp Asp Leu Ala Leu Arg Ile Ala Gly Trp
        1105                1110                1115

Asp Tyr Gly Asn Leu Ile Ile Leu Pro Asp Gly Thr Ala Tyr Gln
        1120                1125                1130

Gly Glu Met Gln Ile Ser Ala Asp Pro Val Lys Asn Ala Ile Ile
        1135                1140                1145

Val Lys Val Pro Lys Lys Tyr Leu Asn Ile Ser Asp Tyr Gly Leu
        1150                1155                1160

Tyr Thr Ala Val Ile Val Gly Ser Gln Asp Gly Tyr Gly Pro Asp
        1165                1170                1175

Lys Trp Arg Pro Val Ala Ala Glu Ala Glu Gln Trp Lys Leu Gly
        1180                1185                1190
```

```
Gly Ala Asp Pro Gln Ala Val Ile Asp Asn Leu Val Pro Arg Val
        1195                1200                1205

Val Asp Glu Leu Val Pro Glu Gly Phe Lys Pro Thr Gln Glu Glu
        1210                1215                1220

Gln Leu Ser Ser Tyr Asp Leu Glu Lys Lys Thr Leu Ala Thr Val
        1225                1230                1235

Leu Met Val Pro Leu Val Asn Gly Thr Gly Gly Glu Glu Pro Thr
        1240                1245                1250

Pro Thr Glu Ser Pro Thr Glu Thr Thr Thr Thr Thr Pro Ser Glu
        1255                1260                1265

Thr Thr Thr Thr Thr Ser Thr Thr Thr Gly Pro Ser Ser Thr Thr
        1270                1275                1280

Thr Ser Thr Pro Gly Gly Gly Ile Cys Gly Pro Gly Ile Ile Ala
        1285                1290                1295

Gly Leu Ala Leu Ile Pro Leu Leu Leu Lys Arg Arg Asn
        1300                1305                1310
```

<210> SEQ ID NO 12
<211> LENGTH: 809
<212> TYPE: PRT
<213> ORGANISM: Artificial Sequence
<220> FEATURE:
<223> OTHER INFORMATION: Hybrid pullulanase of Thermoccus hydrothermalis
      and Thermococcus litoralis
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)

<400> SEQUENCE: 12

```
Met Lys Lys Pro Leu Gly Lys Ile Val Ala Ser Thr Ala Leu Leu Ile
         -25                 -20                 -15

Ser Val Ala Phe Ser Ser Ser Ile Ala Ser Ala Glu Glu Pro Lys Pro
    -10                  -5                  -1  1                   5

Leu Asn Val Ile Ile Val Trp His Gln His Gln Pro Tyr Tyr Tyr Asp
                    10                  15                  20

Pro Ile Gln Asp Ile Tyr Thr Arg Pro Trp Val Arg Leu His Ala Ala
                25                  30                  35

Asn Asn Tyr Trp Lys Met Ala Asn Tyr Leu Ser Lys Tyr Pro Asp Val
            40                  45                  50

His Val Ala Ile Asp Leu Ser Gly Ser Leu Ile Ala Gln Leu Ala Asp
    55                  60                  65

Tyr Met Asn Gly Lys Lys Asp Thr Tyr Gln Ile Val Thr Glu Lys Ile
70                  75                  80                  85

Ala Asn Gly Glu Pro Leu Thr Leu Glu Asp Lys Trp Phe Met Leu Gln
                90                  95                  100

Ala Pro Gly Gly Phe Phe Asp His Thr Ile Pro Trp Asn Gly Glu Pro
                105                 110                 115

Val Ala Asp Glu Asn Gly Asn Pro Tyr Arg Glu Gln Trp Asp Arg Tyr
            120                 125                 130

Ala Glu Leu Lys Asp Lys Arg Asn Asn Ala Phe Lys Lys Tyr Ala Asn
    135                 140                 145

Leu Pro Leu Asn Glu Gln Lys Val Lys Ile Thr Ala Glu Phe Thr Glu
150                 155                 160                 165

Gln Asp Tyr Ile Asp Leu Ala Val Leu Phe Asn Leu Ala Trp Ile Asp
                170                 175                 180
```

```
Tyr Asn Tyr Ile Ile Asn Thr Pro Glu Leu Lys Ala Leu Tyr Asp Lys
            185                 190                 195

Val Asp Val Gly Gly Tyr Thr Lys Glu Asp Val Ala Thr Val Leu Lys
            200                 205                 210

His Gln Met Trp Leu Leu Asn His Thr Phe Glu Glu His Glu Lys Ile
            215                 220                 225

Asn Tyr Leu Leu Gly Asn Gly Asn Val Glu Val Thr Val Val Pro Tyr
230                 235                 240                 245

Ala His Pro Ile Gly Pro Leu Leu Asn Asp Phe Gly Trp Tyr Glu Asp
                250                 255                 260

Phe Asp Ala His Val Lys Lys Ala His Glu Leu Tyr Lys Lys Tyr Leu
                265                 270                 275

Gly Asp Asn Arg Val Glu Pro Gln Gly Gly Trp Ala Ala Glu Ser Ala
            280                 285                 290

Leu Asn Asp Lys Thr Leu Glu Ile Leu Thr Asn Asn Gly Trp Lys Trp
            295                 300                 305

Val Met Thr Asp Gln Met Val Leu Asp Ile Leu Gly Ile Pro Asn Thr
310                 315                 320                 325

Val Glu Asn Tyr Tyr Lys Pro Trp Val Ala Glu Phe Asn Gly Lys Lys
                330                 335                 340

Ile Tyr Leu Phe Pro Arg Asn His Asp Leu Ser Asp Arg Val Gly Phe
            345                 350                 355

Arg Tyr Ser Gly Met Asn Gln Tyr Gln Ala Val Glu Asp Phe Val Asn
            360                 365                 370

Glu Leu Leu Lys Val Gln Lys Glu Asn Tyr Asp Gly Ser Leu Val Tyr
            375                 380                 385

Val Val Thr Leu Asp Gly Glu Asn Pro Trp Glu His Tyr Pro Phe Asp
390                 395                 400                 405

Gly Lys Ile Phe Leu Glu Glu Leu Tyr Lys Lys Leu Thr Glu Leu Gln
                410                 415                 420

Lys Gln Gly Leu Ile Arg Thr Val Thr Pro Ser Glu Tyr Ile Gln Met
            425                 430                 435

Tyr Gly Asp Lys Ala Asn Lys Leu Thr Pro Arg Met Met Glu Arg Leu
            440                 445                 450

Asp Leu Thr Gly Asp Asn Val Asn Ala Leu Leu Lys Ala Gln Ser Leu
            455                 460                 465

Gly Glu Leu Tyr Asp Met Thr Gly Val Lys Glu Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
            520                 525                 530

Glu Tyr Leu Leu Arg Ala Glu Ala Ser Asp Trp Phe Trp Trp Tyr Gly
            535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
            585                 590                 595
```

```
Gly Leu Val Gly Leu Lys Asp Gly Glu Met Lys Asn Phe Ser Ser Met
            600                 605                 610
Ser Pro Leu Ala Lys Gly Val Ser Val Tyr Phe Asp Gly Glu Gly Ile
        615                 620                 625
His Phe Ile Val Lys Gly Asn Leu Asp Arg Phe Glu Val Ser Ile Trp
630                 635                 640                 645
Glu Lys Asp Glu Arg Val Gly Asn Thr Phe Thr Arg Leu Gln Glu Lys
                650                 655                 660
Pro Asp Glu Leu Ser Tyr Phe Met Phe Pro Phe Ser Arg Asp Ser Val
            665                 670                 675
Gly Leu Leu Ile Thr Lys His Val Val Tyr Glu Asn Gly Lys Ala Glu
        680                 685                 690
Ile Tyr Gly Ala Thr Asp Tyr Glu Lys Ser Glu Lys Leu Gly Glu Ala
695                 700                 705
Thr Val Lys Asn Thr Ser Glu Gly Ile Glu Val Val Leu Pro Phe Asp
710                 715                 720                 725
Tyr Ile Glu Asn Pro Ser Asp Phe Tyr Phe Ala Val Ser Thr Val Lys
                730                 735                 740
Asp Gly Asp Leu Glu Val Ile Ser Thr Pro Val Glu Leu Lys Leu Pro
            745                 750                 755
Thr Glu Val Lys Gly Val Val Ile Ala Asp Ile Thr Asp Pro Glu Gly
        760                 765                 770
Asp Asp His Gly Pro Gly Asn Tyr Thr
    775                 780

<210> SEQ ID NO 13
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 13

Ala Glu Leu Glu Gly Leu Asp Glu Ser Ala Ala Gln Val Met Ala Thr
1               5                   10                  15
Tyr Val Trp Asn Leu Gly Tyr Asp Gly Ser Gly Ile Thr Ile Gly Ile
            20                  25                  30
Ile Asp Thr Gly Ile Asp Ala Ser His Pro Asp Leu Gln Gly Lys Val
        35                  40                  45
Ile Gly Trp Val Asp Phe Val Asn Gly Arg Ser Tyr Pro Tyr Asp Asp
    50                  55                  60
His Gly His Gly Thr His Val Ala Ser Ile Ala Ala Gly Thr Gly Ala
65                  70                  75                  80
Ala Ser Asn Gly Lys Tyr Lys Gly Met Ala Pro Gly Ala Lys Leu Ala
                85                  90                  95
Gly Ile Lys Val Leu Gly Ala Asp Gly Ser Gly Ser Ile Ser Thr Ile
            100                 105                 110
Ile Lys Gly Val Glu Trp Ala Val Asp Asn Lys Asp Lys Tyr Gly Ile
        115                 120                 125
Lys Val Ile Asn Leu Ser Leu Gly Ser Ser Gln Ser Ser Asp Gly Thr
    130                 135                 140
Asp Ala Leu Ser Gln Ala Val Asn Ala Ala Trp Asp Ala Gly Leu Val
145                 150                 155                 160
Val Val Val Ala Ala Gly Asn Ser Gly Pro Asn Lys Tyr Thr Ile Gly
```

```
                165                 170                 175
Ser Pro Ala Ala Ala Ser Lys Val Ile Thr Val Gly Ala Val Asp Lys
            180                 185                 190

Tyr Asp Val Ile Thr Ser Phe Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Gly Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 14
<211> LENGTH: 595
<212> TYPE: PRT
<213> ORGANISM: Penicillium oxalicum
<220> FEATURE:
<221> NAME/KEY: mat_peptide
<222> LOCATION: (1)..(595)
<223> OTHER INFORMATION: mature Penicillium oxalicum glucoamylase
      sequence

<400> SEQUENCE: 14

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
```

```
                100             105             110
Asp Gly Ser Gly Leu Gly Glu Pro Lys Phe Glu Ile Asp Leu Asn Pro
            115                 120                 125

Phe Ser Gly Ala Trp Gly Arg Pro Gln Arg Asp Gly Pro Ala Leu Arg
            130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
            195                 200                 205

Leu Val Glu Gly Ser Gln Leu Ala Lys Lys Leu Gly Lys Ser Cys Asp
            210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
                260                 265                 270

Pro Glu Ala Ala Cys Asp Asp Ala Thr Phe Gln Pro Cys Ser Ala Arg
            275                 280                 285

Ala Leu Ala Asn His Lys Val Tyr Val Asp Ser Phe Arg Ser Ile Tyr
            290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
                340                 345                 350

Leu Gly Lys Leu Glu Val Ser Glu Thr Ser Leu Ser Phe Phe Lys Asp
            355                 360                 365

Phe Asp Ala Thr Val Lys Ile Gly Ser Tyr Ser Arg Asn Ser Lys Thr
            370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
                420                 425                 430

Ser Phe Ala Ser Phe Leu Thr Ala Thr Gln Arg Arg Asp Ala Val Val
            435                 440                 445

Pro Pro Ser Trp Gly Ala Lys Ser Ala Asn Lys Val Pro Thr Thr Cys
            450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
                500                 505                 510

Gly Asn Ile Thr Ala Leu Gly Asn Trp Asp Ala Lys Lys Gly Phe Pro
            515                 520                 525
```

Leu Thr Ala Asn Leu Tyr Thr Gln Asp Gln Asn Leu Trp Phe Ala Ser
        530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595

<210> SEQ ID NO 15
<211> LENGTH: 49
<212> TYPE: DNA
<213> ORGANISM: artificial sequence
<220> FEATURE:
<223> OTHER INFORMATION: Prot F primer

<400> SEQUENCE: 15
aacgacggta cccggggatc ggatccatgc ggctcgttgc ttccctaac          49

<210> SEQ ID NO 16
<211> LENGTH: 48
<212> TYPE: DNA
<213> ORGANISM: artificial sequence
<220> FEATURE:
<223> OTHER INFORMATION: Prot R primer

<400> SEQUENCE: 16
ctaattacat gatgcggccc ttaattaatt agcaaccaag gtatatgg           48

<210> SEQ ID NO 17
<211> LENGTH: 20
<212> TYPE: DNA
<213> ORGANISM: Artificial sequence
<220> FEATURE:
<223> OTHER INFORMATION: AM34 Primer

<400> SEQUENCE: 17
taggagttta gtgaacttgc                                          20

<210> SEQ ID NO 18
<211> LENGTH: 18
<212> TYPE: DNA
<213> ORGANISM: Artificial sequence
<220> FEATURE:
<223> OTHER INFORMATION: AM35 Primer

<400> SEQUENCE: 18
ttcgagcgtc ccaaaacc                                            18

<210> SEQ ID NO 19
<211> LENGTH: 25
<212> TYPE: DNA
<213> ORGANISM: Artificial sequence
<220> FEATURE:
<223> OTHER INFORMATION: Sense Primer

<400> SEQUENCE: 19
atgcgtctca ctctattatc aggtg                                    25

<210> SEQ ID NO 20
<211> LENGTH: 39

<210> SEQ ID NO 20
<211> LENGTH: 39
<212> TYPE: DNA
<213> ORGANISM: Artificial sequence
<220> FEATURE:
<223> OTHER INFORMATION: Primer F

<400> SEQUENCE: 20
acacaactgg ggatccacca tgcgtctcac tctattatc                                39

<210> SEQ ID NO 21
<211> LENGTH: 37
<212> TYPE: DNA
<213> ORGANISM: Artificial sequence
<220> FEATURE:
<223> OTHER INFORMATION: Primer R

<400> SEQUENCE: 21
agatctcgag aagcttaaaa ctgccacacg tcgttgg                                  37

<210> SEQ ID NO 22
<211> LENGTH: 18
<212> TYPE: DNA
<213> ORGANISM: Artificial sequence
<220> FEATURE:
<223> OTHER INFORMATION: Primer

<400> SEQUENCE: 22
gcagtctttc caattgac                                                       18

<210> SEQ ID NO 23
<211> LENGTH: 18
<212> TYPE: DNA
<213> ORGANISM: Artificial sequence
<220> FEATURE:
<223> OTHER INFORMATION: Primer

<400> SEQUENCE: 23
aattggaaag actgcccg                                                       18

<210> SEQ ID NO 24
<211> LENGTH: 39
<212> TYPE: DNA
<213> ORGANISM: Artificial sequence
<220> FEATURE:
<223> OTHER INFORMATION: Primer

<400> SEQUENCE: 24
acacaactgg ggatccacca tgcgtctcac tctattatc                                39

<210> SEQ ID NO 25
<211> LENGTH: 37
<212> TYPE: DNA
<213> ORGANISM: Artificial sequence
<220> FEATURE:
<223> OTHER INFORMATION: Primer

<400> SEQUENCE: 25
agatctcgag aagcttaaaa ctgccacacg tcgttgg                                  37

<210> SEQ ID NO 26
<211> LENGTH: 574
<212> TYPE: PRT
<213> ORGANISM: Trametes cingulata

<400> SEQUENCE: 26

Met Arg Phe Thr Leu Leu Thr Ser Leu Leu Gly Leu Ala Leu Gly Ala
1               5                   10                  15

-continued

```
Phe Ala Gln Ser Ser Ala Ala Asp Ala Tyr Val Ala Ser Glu Ser Pro
                 20                  25                  30
Ile Ala Lys Ala Gly Val Leu Ala Asn Ile Gly Pro Ser Gly Ser Lys
             35                  40                  45
Ser Asn Gly Ala Lys Ala Gly Ile Val Ile Ala Ser Pro Ser Thr Ser
 50                  55                  60
Asn Pro Asn Tyr Leu Tyr Thr Trp Thr Arg Asp Ser Ser Leu Val Phe
 65                  70                  75                  80
Lys Ala Leu Ile Asp Gln Phe Thr Thr Gly Glu Asp Thr Ser Leu Arg
                 85                  90                  95
Thr Leu Ile Asp Glu Phe Thr Ser Ala Glu Ala Ile Leu Gln Gln Val
            100                 105                 110
Pro Asn Pro Ser Gly Thr Val Ser Thr Gly Gly Leu Gly Glu Pro Lys
            115                 120                 125
Phe Asn Ile Asp Glu Thr Ala Phe Thr Asp Ala Trp Gly Arg Pro Gln
130                 135                 140
Arg Asp Gly Pro Ala Leu Arg Ala Thr Ala Ile Ile Thr Tyr Ala Asn
145                 150                 155                 160
Trp Leu Leu Asp Asn Lys Asn Thr Thr Tyr Val Thr Asn Thr Leu Trp
                165                 170                 175
Pro Ile Ile Lys Leu Asp Leu Asp Tyr Val Ala Ser Asn Trp Asn Gln
            180                 185                 190
Ser Thr Phe Asp Leu Trp Glu Glu Ile Asn Ser Ser Phe Phe Thr
            195                 200                 205
Thr Ala Val Gln His Arg Ala Leu Arg Glu Gly Ala Thr Phe Ala Asn
            210                 215                 220
Arg Ile Gly Gln Thr Ser Val Val Ser Gly Tyr Thr Thr Gln Ala Asn
225                 230                 235                 240
Asn Leu Leu Cys Phe Leu Gln Ser Tyr Trp Asn Pro Thr Gly Gly Tyr
                245                 250                 255
Ile Thr Ala Asn Thr Gly Gly Gly Arg Ser Gly Lys Asp Ala Asn Thr
            260                 265                 270
Val Leu Thr Ser Ile His Thr Phe Asp Pro Ala Ala Gly Cys Asp Ala
            275                 280                 285
Val Thr Phe Gln Pro Cys Ser Asp Lys Ala Leu Ser Asn Leu Lys Val
            290                 295                 300
Tyr Val Asp Ala Phe Arg Ser Ile Tyr Ser Ile Asn Ser Gly Ile Ala
305                 310                 315                 320
Ser Asn Ala Ala Val Ala Thr Gly Arg Tyr Pro Glu Asp Ser Tyr Met
                325                 330                 335
Gly Gly Asn Pro Trp Tyr Leu Thr Thr Ser Ala Val Ala Glu Gln Leu
            340                 345                 350
Tyr Asp Ala Leu Ile Val Trp Asn Lys Leu Gly Ala Leu Asn Val Thr
            355                 360                 365
Ser Thr Ser Leu Pro Phe Phe Gln Gln Phe Ser Ser Gly Val Thr Val
            370                 375                 380
Gly Thr Tyr Ala Ser Ser Ser Thr Phe Lys Thr Leu Thr Ser Ala
385                 390                 395                 400
Ile Lys Thr Phe Ala Asp Gly Phe Leu Ala Val Asn Ala Lys Tyr Thr
                405                 410                 415
Pro Ser Asn Gly Gly Leu Ala Glu Gln Tyr Ser Arg Ser Asn Gly Ser
            420                 425                 430
```

Pro Val Ser Ala Val Asp Leu Thr Trp Ser Tyr Ala Ala Leu Thr
            435                 440                 445

Ser Phe Ala Ala Arg Ser Gly Lys Thr Tyr Ala Ser Trp Gly Ala Ala
450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Thr Val Phe Gly Glu Asn
                485                 490                 495

Ile Tyr Ile Thr Gly Ser Val Pro Ala Leu Gln Asn Trp Ser Pro Asp
                500                 505                 510

Asn Ala Leu Ile Leu Ser Ala Ala Asn Tyr Pro Thr Trp Ser Ile Thr
            515                 520                 525

Val Asn Leu Pro Ala Ser Thr Thr Ile Glu Tyr Lys Tyr Ile Arg Lys
530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
                565                 570

<210> SEQ ID NO 27
<211> LENGTH: 583
<212> TYPE: PRT
<213> ORGANISM: Rhizomucor pusillus

<400> SEQUENCE: 27

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
            35                  40                  45

Tyr Ile Ser Gly Met Gly Phe Asp Ala Ile Trp Ile Ser Pro Ile Pro
        50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
                100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Thr Ser Lys Thr Thr Ala Thr Ala
    450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 28
<211> LENGTH: 618
<212> TYPE: PRT
<213> ORGANISM: Talaromyces emersonii

<400> SEQUENCE: 28

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu

-continued

```
                20                  25                  30
Asp Ser Phe Leu Ala Thr Glu Thr Pro Ile Ala Leu Gln Gly Val Leu
             35                  40                  45
Asn Asn Ile Gly Pro Asn Gly Ala Asp Val Ala Gly Ala Ser Ala Gly
 50                  55                  60
Ile Val Val Ala Ser Pro Ser Arg Ser Asp Pro Asn Tyr Phe Tyr Ser
 65                  70                  75                  80
Trp Thr Arg Asp Ala Ala Leu Thr Ala Lys Tyr Leu Val Asp Ala Phe
                 85                  90                  95
Ile Ala Gly Asn Lys Asp Leu Glu Gln Thr Ile Gln Gln Tyr Ile Ser
                100                 105                 110
Ala Gln Ala Lys Val Gln Thr Ile Ser Asn Pro Ser Gly Asp Leu Ser
            115                 120                 125
Thr Gly Gly Leu Gly Glu Pro Lys Phe Asn Val Asn Glu Thr Ala Phe
            130                 135                 140
Thr Gly Pro Trp Gly Arg Pro Gln Arg Asp Gly Pro Ala Leu Arg Ala
145                 150                 155                 160
Thr Ala Leu Ile Ala Tyr Ala Asn Tyr Leu Ile Asp Asn Gly Glu Ala
                165                 170                 175
Ser Thr Ala Asp Glu Ile Ile Trp Pro Ile Val Gln Asn Asp Leu Ser
            180                 185                 190
Tyr Ile Thr Gln Tyr Trp Asn Ser Ser Thr Phe Asp Leu Trp Glu Glu
            195                 200                 205
Val Glu Gly Ser Ser Phe Phe Thr Thr Ala Val Gln His Arg Ala Leu
            210                 215                 220
Val Glu Gly Asn Ala Leu Ala Thr Arg Leu Asn His Thr Cys Ser Asn
225                 230                 235                 240
Cys Val Ser Gln Ala Pro Gln Val Leu Cys Phe Leu Gln Ser Tyr Trp
                245                 250                 255
Thr Gly Ser Tyr Val Leu Ala Asn Phe Gly Gly Ser Gly Arg Ser Gly
            260                 265                 270
Lys Asp Val Asn Ser Ile Leu Gly Ser Ile His Thr Phe Asp Pro Ala
            275                 280                 285
Gly Gly Cys Asp Asp Ser Thr Phe Gln Pro Cys Ser Ala Arg Ala Leu
            290                 295                 300
Ala Asn His Lys Val Val Thr Asp Ser Phe Arg Ser Ile Tyr Ala Ile
305                 310                 315                 320
Asn Ser Gly Ile Ala Glu Gly Ser Ala Val Ala Val Gly Arg Tyr Pro
                325                 330                 335
Glu Asp Val Tyr Gln Gly Gly Asn Pro Trp Tyr Leu Ala Thr Ala Ala
            340                 345                 350
Ala Ala Glu Gln Leu Tyr Asp Ala Ile Tyr Gln Trp Lys Lys Ile Gly
            355                 360                 365
Ser Ile Ser Ile Thr Asp Val Ser Leu Pro Phe Phe Gln Asp Ile Tyr
            370                 375                 380
Pro Ser Ala Ala Val Gly Thr Tyr Asn Ser Gly Ser Thr Thr Phe Asn
385                 390                 395                 400
Asp Ile Ile Ser Ala Val Gln Thr Tyr Gly Asp Gly Tyr Leu Ser Ile
                405                 410                 415
Val Glu Lys Tyr Thr Pro Ser Asp Gly Ser Leu Thr Glu Gln Phe Ser
            420                 425                 430
Arg Thr Asp Gly Thr Pro Leu Ser Ala Ser Ala Leu Thr Trp Ser Tyr
            435                 440                 445
```

Ala Ser Leu Leu Thr Ala Ser Ala Arg Arg Gln Ser Val Val Pro Ala
    450                 455                 460

Ser Trp Gly Glu Ser Ser Ala Ser Ser Val Pro Ala Val Cys Ser Ala
465                 470                 475                 480

Thr Ser Ala Thr Gly Pro Tyr Ser Thr Ala Thr Asn Thr Val Trp Pro
                485                 490                 495

Ser Ser Gly Ser Gly Ser Ser Thr Thr Thr Ser Ser Ala Pro Cys Thr
                500                 505                 510

Thr Pro Thr Ser Val Ala Val Thr Phe Asp Glu Ile Val Ser Thr Ser
            515                 520                 525

Tyr Gly Glu Thr Ile Tyr Leu Ala Gly Ser Ile Pro Glu Leu Gly Asn
530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Phe Lys Asn Gln Thr Asp Gly Thr Ile Val Trp
                580                 585                 590

Glu Asp Asp Pro Asn Arg Ser Tyr Thr Val Pro Ala Tyr Cys Gly Gln
            595                 600                 605

Thr Thr Ala Ile Leu Asp Asp Ser Trp Gln
    610                 615

<210> SEQ ID NO 29
<211> LENGTH: 863
<212> TYPE: PRT
<213> ORGANISM: Aspergillus fumigatus

<400> SEQUENCE: 29

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly

```
                195                 200                 205
Tyr Gly Tyr Asn Ile Thr Glu Thr Ile Ser Ser Asn Val Asp Asp Lys
210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                    245                 250                 255

Gly Cys Gln Asn Ser Gln Thr Leu Asn Lys Leu Leu Lys Ala Glu Leu
                260                 265                 270

Gly Phe Gln Gly Phe Val Met Ser Asp Trp Ser Ala His His Ser Gly
            275                 280                 285

Val Gly Ala Ala Leu Ala Gly Leu Asp Met Ser Met Pro Gly Asp Ile
        290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                    325                 330                 335

Arg Ile Met Thr Ala Tyr Tyr Lys Val Gly Arg Asp Arg Leu Arg Ile
                340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
        370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                    405                 410                 415

Val Lys Val Gly Val Leu Gly Glu Asp Ala Gly Ser Asn Pro Trp Gly
                420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
        450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                    485                 490                 495

Ser Ser Val Ser Leu Val Phe Val Asn Ala Asp Ser Gly Glu Gly Phe
                500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
        530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                    565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
        610                 615                 620
```

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
            645                 650                 655

Thr Phe Gly Tyr Ser His Leu Arg Val Gln Ala Leu Asn Ser Ser Ser
        660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
            725                 730                 735

Pro Glu Gly Ala Arg Asp Gly Ser Pro Gln Pro Leu Leu Lys Ala Gly
        740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
            805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 30
<211> LENGTH: 250
<212> TYPE: PRT
<213> ORGANISM: Thermoascus aurantiacus

<400> SEQUENCE: 30

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
            85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp

```
                130             135             140
Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 31
<211> LENGTH: 253
<212> TYPE: PRT
<213> ORGANISM: Penicillium emersonii

<400> SEQUENCE: 31

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
                20                  25                  30

Val Ile Gly Asp Gln Phe Tyr Ser Gly Tyr Ile Val Asn Ser Phe Pro
            35                  40                  45

Tyr Glu Ser Asn Pro Pro Val Ile Gly Trp Ala Thr Thr Ala Thr
50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 32
<211> LENGTH: 532
<212> TYPE: PRT
<213> ORGANISM: Aspergillus fumigatus

<400> SEQUENCE: 32

| | | | | | | | | | | | | | | | |
|---|---|---|---|---|---|---|---|---|---|---|---|---|---|---|---|
| Met | Leu | Ala | Ser | Thr | Phe | Ser | Tyr | Arg | Met | Tyr | Lys | Thr | Ala | Leu | Ile |
| 1 | | | | 5 | | | | | 10 | | | | | 15 | |
| Leu | Ala | Ala | Leu | Leu | Gly | Ser | Gly | Gln | Ala | Gln | Gln | Val | Gly | Thr | Ser |
| | | | 20 | | | | | 25 | | | | | 30 | | |
| Gln | Ala | Glu | Val | His | Pro | Ser | Met | Thr | Trp | Gln | Ser | Cys | Thr | Ala | Gly |
| | | 35 | | | | | 40 | | | | | 45 | | | |
| Gly | Ser | Cys | Thr | Thr | Asn | Asn | Gly | Lys | Val | Val | Ile | Asp | Ala | Asn | Trp |
| | 50 | | | | | 55 | | | | | 60 | | | | |
| Arg | Trp | Val | His | Lys | Val | Gly | Asp | Tyr | Thr | Asn | Cys | Tyr | Thr | Gly | Asn |
| 65 | | | | 70 | | | | | 75 | | | | | 80 | |
| Thr | Trp | Asp | Thr | Thr | Ile | Cys | Pro | Asp | Ala | Thr | Cys | Ala | Ser | Asn |
| | | | 85 | | | | | 90 | | | | | 95 | |
| Cys | Ala | Leu | Glu | Gly | Ala | Asn | Tyr | Glu | Ser | Thr | Tyr | Gly | Val | Thr | Ala |
| | | | 100 | | | | | 105 | | | | | 110 | | |
| Ser | Gly | Asn | Ser | Leu | Arg | Leu | Asn | Phe | Val | Thr | Thr | Ser | Gln | Gln | Lys |
| | | | 115 | | | | | 120 | | | | | 125 | | |
| Asn | Ile | Gly | Ser | Arg | Leu | Tyr | Met | Met | Lys | Asp | Asp | Ser | Thr | Tyr | Glu |
| | 130 | | | | | 135 | | | | | 140 | | | | |
| Met | Phe | Lys | Leu | Leu | Asn | Gln | Glu | Phe | Thr | Phe | Asp | Val | Asp | Val | Ser |
| 145 | | | | | 150 | | | | | 155 | | | | | 160 |
| Asn | Leu | Pro | Cys | Gly | Leu | Asn | Gly | Ala | Leu | Tyr | Phe | Val | Ala | Met | Asp |
| | | | | 165 | | | | | 170 | | | | | 175 | |
| Ala | Asp | Gly | Gly | Met | Ser | Lys | Tyr | Pro | Thr | Asn | Lys | Ala | Gly | Ala | Lys |
| | | | 180 | | | | | 185 | | | | | 190 | | |
| Tyr | Gly | Thr | Gly | Tyr | Cys | Asp | Ser | Gln | Cys | Pro | Arg | Asp | Leu | Lys | Phe |
| | | 195 | | | | | 200 | | | | | 205 | | | |
| Ile | Asn | Gly | Gln | Ala | Asn | Val | Glu | Gly | Trp | Gln | Pro | Ser | Ser | Asn | Asp |
| | 210 | | | | | 215 | | | | | 220 | | | | |
| Ala | Asn | Ala | Gly | Thr | Gly | Asn | His | Gly | Ser | Cys | Cys | Ala | Glu | Met | Asp |
| 225 | | | | | 230 | | | | | 235 | | | | | 240 |
| Ile | Trp | Glu | Ala | Asn | Ser | Ile | Ser | Thr | Ala | Phe | Thr | Pro | His | Pro | Cys |
| | | | | 245 | | | | | 250 | | | | | 255 | |
| Asp | Thr | Pro | Gly | Gln | Val | Met | Cys | Thr | Gly | Asp | Ala | Cys | Gly | Gly | Thr |
| | | | 260 | | | | | 265 | | | | | 270 | | |
| Tyr | Ser | Ser | Asp | Arg | Tyr | Gly | Gly | Thr | Cys | Asp | Pro | Asp | Gly | Cys | Asp |
| | | 275 | | | | | 280 | | | | | 285 | | | |
| Phe | Asn | Ser | Phe | Arg | Gln | Gly | Asn | Lys | Thr | Phe | Tyr | Gly | Pro | Gly | Met |
| | 290 | | | | | 295 | | | | | 300 | | | | |
| Thr | Val | Asp | Thr | Lys | Ser | Lys | Phe | Thr | Val | Thr | Gln | Phe | Ile | Thr |
| 305 | | | | | 310 | | | | | 315 | | | | | 320 |
| Asp | Asp | Gly | Thr | Ser | Ser | Gly | Thr | Leu | Lys | Glu | Ile | Lys | Arg | Phe | Tyr |
| | | | | 325 | | | | | 330 | | | | | 335 | |
| Val | Gln | Asn | Gly | Lys | Val | Ile | Pro | Asn | Ser | Glu | Ser | Thr | Trp | Thr | Gly |
| | | | 340 | | | | | 345 | | | | | 350 | | |
| Val | Ser | Gly | Asn | Ser | Ile | Thr | Thr | Glu | Tyr | Cys | Thr | Ala | Gln | Lys | Ser |
| | | 355 | | | | | 360 | | | | | 365 | | | |
| Leu | Phe | Gln | Asp | Gln | Asn | Val | Phe | Glu | Lys | His | Gly | Gly | Leu | Glu | Gly |
| | 370 | | | | | 375 | | | | | 380 | | | | |

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
            405                 410                 415

Thr Ala Ser Ser Thr Thr Pro Gly Val Ala Arg Gly Thr Cys Asp Ile
        420                 425                 430

Ser Ser Gly Val Pro Ala Asp Val Glu Ala Asn His Pro Asp Ala Tyr
    435                 440                 445

Val Val Tyr Ser Asn Ile Lys Val Gly Pro Ile Gly Ser Thr Phe Asn
450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Ala Gly Asn Pro Gly Gly Thr Gly
            485                 490                 495

Val Ala Gln His Tyr Gly Gln Cys Gly Gly Ile Gly Trp Thr Gly Pro
        500                 505                 510

Thr Thr Cys Ala Ser Pro Tyr Thr Cys Gln Lys Leu Asn Asp Tyr Tyr
        515                 520                 525

Ser Gln Cys Leu
    530

<210> SEQ ID NO 33
<211> LENGTH: 454
<212> TYPE: PRT
<213> ORGANISM: Aspergillus fumigatus

<400> SEQUENCE: 33

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile

-continued

```
            210                 215                 220
Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
                260                 265                 270

Ala Gly His Ala Gly Trp Leu Gly Trp Pro Ala Asn Leu Gly Pro Ala
                275                 280                 285

Ala Thr Leu Phe Ala Lys Val Tyr Thr Asp Ala Gly Ser Pro Ala Ala
                290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
                340                 345                 350

Ala His Phe Ile Met Asp Thr Ser Arg Asn Gly Val Gln Pro Thr Lys
                355                 360                 365

Gln Asn Ala Trp Gly Asp Trp Cys Asn Val Ile Gly Thr Gly Phe Gly
                370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
                420                 425                 430

Pro Glu Ala Gly Thr Trp Phe Gln Ala Tyr Phe Glu Gln Leu Leu Thr
                435                 440                 445

Asn Ala Asn Pro Ser Phe
                450
```